US011180481B2

(12) United States Patent
Arora et al.

(10) Patent No.: US 11,180,481 B2
(45) Date of Patent: Nov. 23, 2021

(54) OXOPIPERAZINE HELIX MIMETICS AS INHIBITORS OF THE P53-MDM2 INTERACTION

(71) Applicant: NEW YORK UNIVERSITY, New York, NY (US)

(72) Inventors: Paramjit S. Arora, Cold Spring Harbor, NY (US); Brooke Bullock Lao, Leesville, SC (US); Danielle Guarracino, Princeton, NJ (US); Richard Bonneau, New York, NY (US); Kevin Drew, Austin, TX (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 15/304,490

(22) PCT Filed: Apr. 15, 2015

(86) PCT No.: PCT/US2015/025914
§ 371 (c)(1),
(2) Date: Oct. 14, 2016

(87) PCT Pub. No.: WO2015/160914
PCT Pub. Date: Oct. 22, 2015

(65) Prior Publication Data
US 2017/0037033 A1 Feb. 9, 2017

Related U.S. Application Data

(60) Provisional application No. 61/979,784, filed on Apr. 15, 2014.

(51) Int. Cl.
*C07D 403/14* (2006.01)
*C07D 403/06* (2006.01)
*C07D 241/08* (2006.01)

(52) U.S. Cl.
CPC ......... *C07D 403/06* (2013.01); *C07D 241/08* (2013.01); *C07D 403/14* (2013.01)

(58) Field of Classification Search
CPC .................................................. C07D 403/14
See application file for complete search history.

(56) References Cited

U.S. PATENT DOCUMENTS

| | | |
|---|---|---|
| 4,758,652 A | 7/1988 | Heitz et al. |
| 5,369,103 A | 11/1994 | Cliffe et al. |
| 6,841,675 B1 | 1/2005 | Schmidt et al. |

(Continued)

FOREIGN PATENT DOCUMENTS

| | | |
|---|---|---|
| JP | 2003-519629 | 6/2003 |
| WO | 03/0692212 A1 | 7/2003 |

(Continued)

OTHER PUBLICATIONS

Arora, "Non-Peptidic α-Helix and β-Strand Mimetics," Award Abstract No. 0848410 (National Science Foundation, Feb. 1, 2009).
Arora, Presentation, "Synthetic Strategies for Targeting Protein Interfaces" (Nov. 2, 2009).
Chène, "Inhibiting the p53-Mdm2 Interaction: An Important Target for Cancer Therapy," Nat. Rev. Cancer 3:102-09 (2003).
Extended European Search Report for European Patent Application No. 14181686.8 (dated Apr. 14, 2015).
(Continued)

*Primary Examiner* — Brian E McDowell
(74) *Attorney, Agent, or Firm* — Troutman Pepper Hamilton Sanders LLP (Rochester)

(57) ABSTRACT

The present invention relates to oligooxopiperazines for modulating the p53-Mdm2 interaction. Exemplary oligooxopiperazines include those of Formula IA, Formula IB, and Formula IC below (wherein the various substituents are as defined herein). Methods of using the oligooxopiperazines are also disclosed.

10 Claims, 17 Drawing Sheets

(56) References Cited

U.S. PATENT DOCUMENTS

| | | |
|---|---|---|
| 8,791,121 B2 | 7/2014 | Arora et al. |
| 9,309,230 B2 | 4/2016 | Arora et al. |
| 2003/0191049 A1 | 10/2003 | Amblard et al. |
| 2012/0040992 A1 | 2/2012 | Arora et al. |
| 2015/0072991 A1 | 3/2015 | Arora et al. |
| 2016/0214965 A1 | 7/2016 | Arora et al. |

FOREIGN PATENT DOCUMENTS

| | | |
|---|---|---|
| WO | 2009/097486 A1 | 8/2009 |
| WO | 2012/021144 A1 | 2/2012 |
| WO | 2013/123511 A1 | 8/2013 |

OTHER PUBLICATIONS

International Preliminary Report on Patentability for International Application No. PCT US2010/054983 (dated Feb. 12, 2013).

International Search Report for International Application No. PCT US2010/054983 (dated Oct. 20, 2011).

International Search Report and Written Opinion for corresponding International Application No. PCT/US2015/025914 (dated Jul. 6, 2015).

Kussie et al., "Structure of the MDM2 Oncoprotein Bound to the p53 Tumor Suppressor Transactivation Domain," Science 274(5289):948-53 (1996).

Lau et al., "Rational Design of Topographical Helix Mimics as Potent Inhibitors of Protein-Protein Interactions," J. Am. Chem. Soc. 136:7877-88 (2014).

Supplementary European Search Report for European Patent Application No. 10855990.7 (dated Jan. 15, 2014).

Tošovská & Arora "Oligooxopiperazines as Nonpeptidic Alpha-Helix Mimetics," Org. Lett. 12:1588-91 (2010).

Vassilev et al., "In Vivo Activation of the p53 Pathway by Small-Molecule Antagonists of MDM2," Science 303 (5659):844-48 (2004).

Written Opinion for International Application No. PCT US2010/054983 (dated Oct. 20, 2011).

Yu et al., "Potent and Orally Active Small-Molecule Inhibitors of the MDM2-p53 Interaction," J. Med. Chem. 52 (24)7970-73 (2009).

International Preliminary Report on Patentability for corresponding International Application No. PCT/US2015/025914 (dated Oct. 27, 2016).

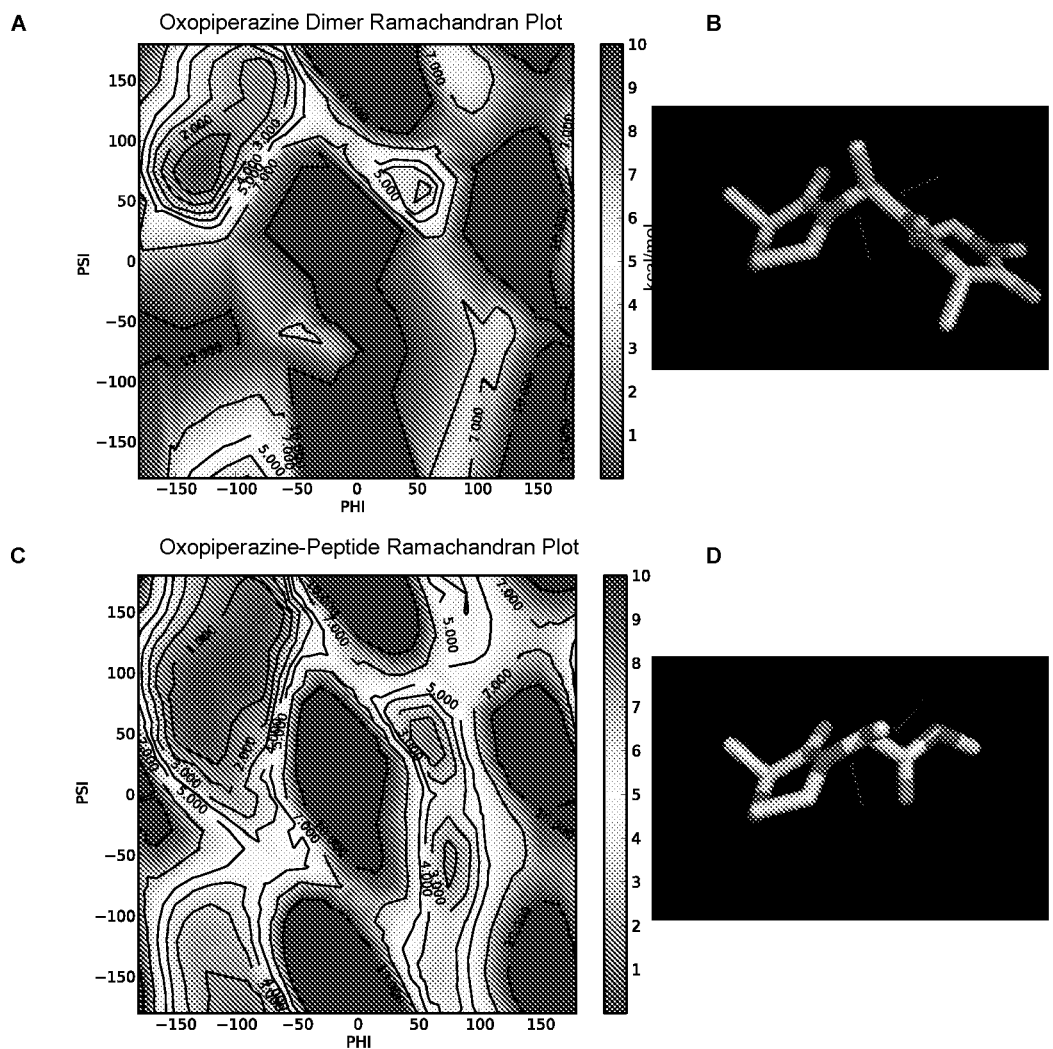
Figures 9A–D
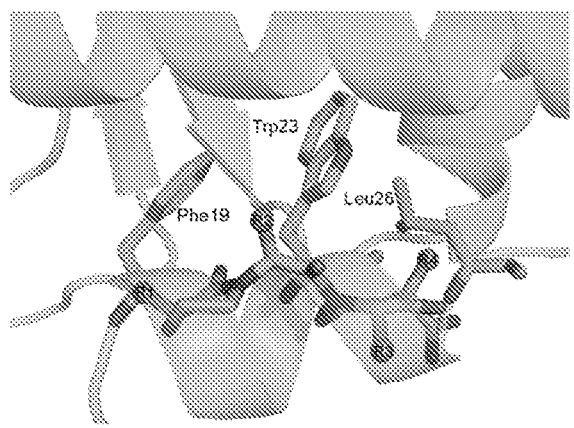
Figure 10

Figures 11A–D

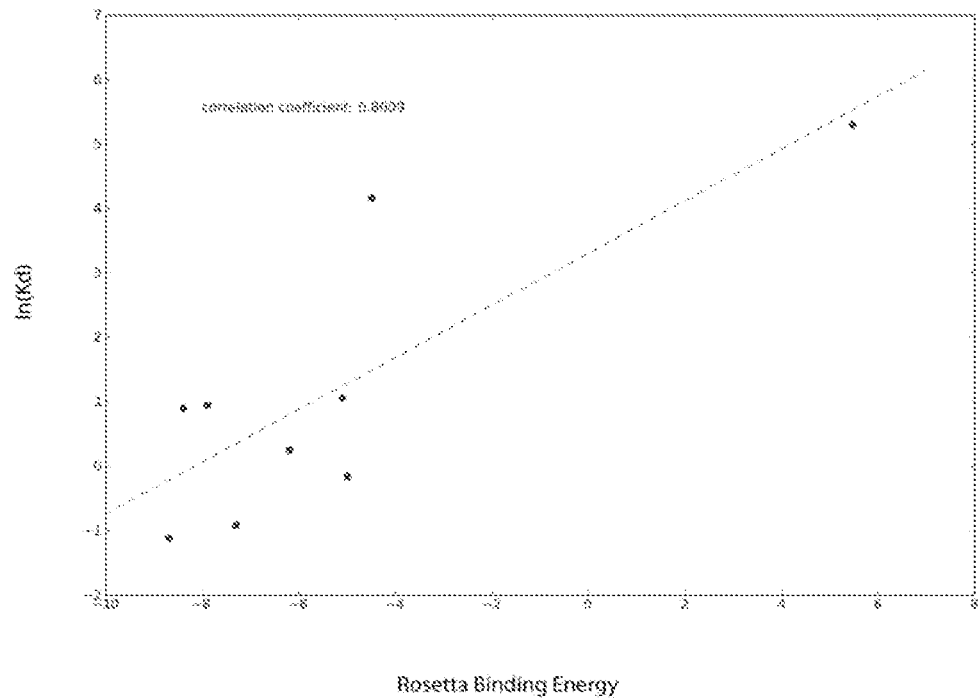
Figure 12
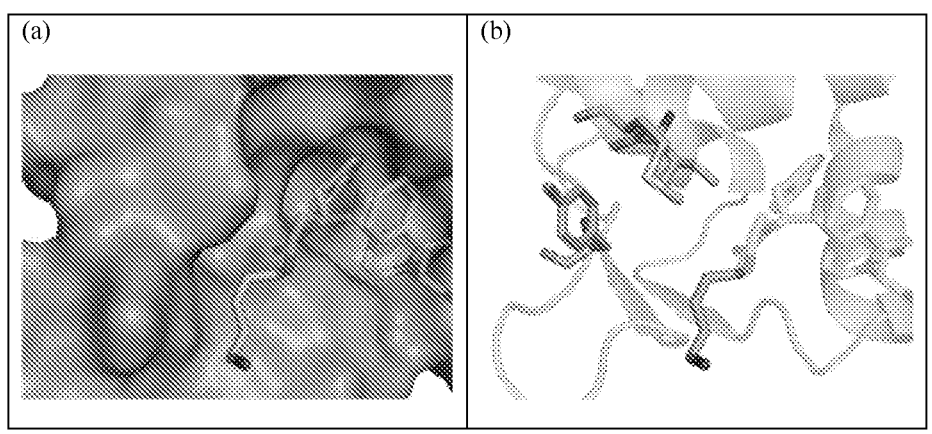
Figures 13A–B

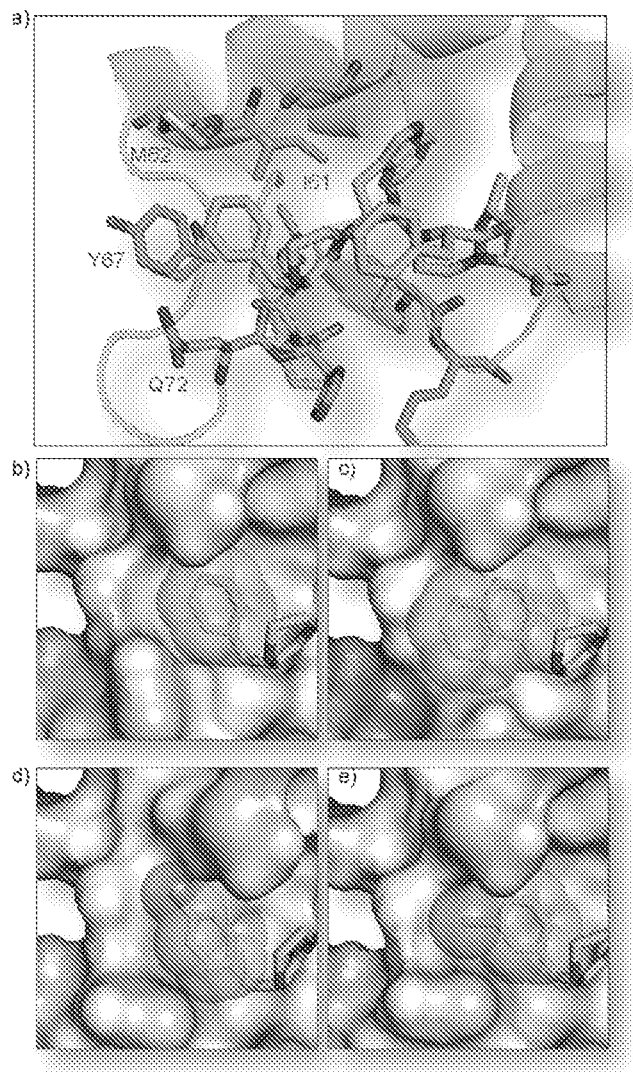
Figures 14A–E

OXOPIPERAZINE HELIX MIMETICS AS INHIBITORS OF THE P53-MDM2 INTERACTION

This application is a national stage application under 35 U.S.C. § 371 of PCT Application No. PCT/US2015/025914, filed Apr. 15, 2015, which claims the benefit of U.S. Provisional Patent Application Ser. No. 61/979,784, filed Apr. 15, 2014, each of which is hereby incorporated by reference in its entirety.

This invention was made with government support under grant number CHE-1151554 awarded by the National Science Foundation and grant numbers RC4-AI092765, PN2-EY016586, 1U54CA143907-01, and EY016586-06 awarded by the National Institutes for Health. The government has certain rights in the invention.

FIELD OF THE INVENTION

This invention is directed generally to oligooxopiperazine helix mimetics that inhibit the interaction between Mdm2 and p53.

BACKGROUND OF THE INVENTION

The p53 tumor suppressor plays a pivotal role in regulating cellular processes (Pei et al., Oncotarget 3(3):228-35 (2012)). p53 is inactive under normal physiological conditions and activated in response to various types of stresses such as DNA damage, hypoxia, and ribosomal stress (Miliani de Marval & Zhang, Oncotarget 2:234-238 (2011)). As illustrated in FIG. 1, activated p53 plays an essential role in guarding cells against stress (e.g., oncogene activation, telomere erosion, hypoxia) by inducing cell cycle arrest and inhibiting cell growth, inducing cell repair, or promoting cell apoptosis, depending on the type of stress and the cellular context (Pei et al., Oncotarget 3(3):228-35 (2012); Khoury & Dömling, Curr. Pharm. Des. 18(30):4668-78 (2012)).

Mdm2 (murine double minute 2) was discovered on double minute chromosomes in a derivative cell line of NIH-3T3 cells (Fakharzadeh et al., EMBO J. 10:1565-69 (1991); Momand et al., Cell 69:1237-45 (1992)). Mdm2 belongs to the family of E3 ubiquitin ligases that contain a RING [really interesting new gene] domain (Joazeiro & Weissman, Cell 102:549-52 (2000)) and serves as the major E3 ubiquitin ligase for p53 degradation. Several studies have illustrated the importance of Mdm2 in the control of p53 activity (Pei et al., Oncotarget 3(3):228-35 (2012)). The mechanism by which Mdm2 suppresses p53 has classically been thought to occur by two distinct ways: by binding to the N-terminal domain of p53 and masking p53's access to transcriptional machinery, and by ubiquitinating p53 and targeting it for proteasomal degradation (Haupt et al., Nature 387:296-99 (1997); Honda & Yasuda, Oncogene 19:1473-76 (2000); Kubbutat et al., Nature 387:299-303 (1997); Oliner et al., Nature 362:857-60 (1993)). Mdm2 also transports p53 into the cytoplasm, away from nuclear DNA, making p53 unable to affect transcription (Khoury & Dömling, Curr. Pharm. Des. 18(30):4668-78 (2012)).

p53 is the most frequently inactivated tumor suppressor gene in human cancer (Pei et al., Oncotarget 3(3):228-35 (2012)). Around 22 million people in 2012 were living with a tumor affected by p53 (Khoury & Dömling, Curr. Pharm. Des. 18(30):4668-78 (2012)). Clinical studies have shown that p53 is mutated in approximately 50% of human cancers (Pei et al., Oncotarget 3(3):228-35 (2012)). The other 50% contain wild-type p53, yet are unaffected by its tumor suppression activity (id.). This is often accomplished through the overexpression of Mdm2 by gene amplification or mutation (id.). The amplification and/or aberrant expression of Mdm2 occurs in a number of tumors of diverse origin, especially in tumors that retain wild-type p53 (id.). The mechanism by which Mdm2 amplification promotes tumorigenesis is at least in part related to its interaction with p53. In cells over-expressing Mdm2 the protective function of p53 is blocked and thus cells are unable to respond to DNA damage or cellular stress by increasing p53 levels, leading to cell growth arrest and/or apoptosis. Thus after DNA damage and/or cellular stress, cells over-expressing Mdm2 are free to continue to proliferate and assume a tumorigenic phenotype. Under these conditions disruption of the interaction of p53 and Mdm2 would release the p53 and thus allow normal signals of growth arrest and/or apoptosis to function.

It has been accepted, at least theoretically, that reactivation or restoration of p53 activity in tumors is a promising cancer therapeutic strategy (Pei et al., Oncotarget 3(3):228-35 (2012)). Some proposed strategies include repressing the expression of Mdm2, blocking the p53-Mdm2 interaction, and inhibiting the ubiquitin ligase activity of Mdm2 (Li et al., Cell Cycle 9:1411-20 (2010); Azmi et al., Oncotarget 2:378-92 (2011)). There has been extensive validation of Mdm2 as a target showing that even a small reduction in Mdm2 is significant enough to increase p53 activity (Khoury & Dömling, Curr. Pharm. Des. 18(30):4668-78 (2012)). Targeting small molecules to specifically inhibit Mdm2 could aid in more specific treatments (Brown et al., Nat. Rev. Cancer 9(12):862-73 (2009); Wu et al., Genes Dev. 7(7A): 1126-32 (1993); Momand et al., Cell 69:1237-45 (1992); Danovi et al., Mol. Cell. Biol. 24(13):5835-43 (2004)). For example, Nutlin, a small molecule that inhibits Mdm2, can trigger cell-cycle arrest and apoptosis and exhibits antitumor efficacy in a murine xenograft model (Vassilev et al., Science 303:844-48 (2004)). Several studies also revealed that rational combination of Nutlin-3a and other drugs could potentiate chemotherapy with mitotic inhibitors against cancer and protect normal cells from cytostatic agents (Apontes et al., Oncotarget 2:222-33 (2011); Rao et al., Oncotarget 1:639-50 (2010)). However, several issues have been raised from studies of Nutlin (Pei et al., Oncotarget 3(3):228-35 (2012)). One of them is the high toxicity of inhibiting Mdm2 by Nutlin (id.). Studies in mice indicate that Mdm2 loss leads to induction of p53 activation and p53-dependent pathologies in both proliferating and quiescent cells, such as erythroid progenitor cells, neurons, and smooth muscle cells (Marine & Lozano, Cell Death Differ. 17:93-102 (2010)).

The therapeutic effectiveness of DNA damaging agents currently used in treatment (chemotherapy and radiotherapy) may also be limited through the negative regulation of p53 by Mdm2 Thus if the Mdm2 feed-back inhibition of p53 is interrupted, an increase in functional p53 levels will increase the therapeutic effectiveness of such agents by restoring the wild-type p53 function that leads to apoptosis and/or reversing of p53-associated drug resistance. Combining Mdm2 inhibition and DNA-damaging treatments in vivo has been shown to lead to synergistic anti-tumor effects (Vousden, *Cell* 103:691-94 (2000)).

Protein-protein interactions are often mediated by amino acid residues organized on secondary structures (Jones & Thornton, *Prog. Biophys. Mol. Bio.* 63:31(1995)). Designed oligomeric ligands that can mimic the array of protein-like functionality at interfaces offer an attractive approach to target therapeutically important interactions (Ko et al., *Chem. Soc. Rev.* 40:4411 (2011)). Efforts to mimic interfacial α-helices have resulted in three overarching synthetic strategies: helix stabilization, helical foldamers, and helical surface mimetics (Azzarito et al., *Nat. Chem.* 5:161 (2013); Henchey et al., *Curr. Opin. Chem. Biol.* 12:692 (2008)). Helix stabilization employs side chain crosslinks (Schafmeister et al., *J. Am. Chem. Soc.* 122:5891 (2000); Harrison et al., *Proc. Nat'l Acad. Sci. U.S.A.* 107:11686 (2010)) or hydrogen-bond surrogates (Patgiri et al., *Acc. Chem. Res.* 41:1289 (2008)) to preorganize amino acid residues and initiate helix formation. Helical foldamers are nonnatural oligomers that adopt defined helical conformations (Gellman, *Acc. Chem. Res.* 31:173 (1998); Goodman et al., *Nat. Chem. Biol.* 3:252 (2007)). Prominent examples include β-peptide (Cheng et al., *Chem. Rev.* 101:3219 (2001); Horne & Gellman, *Acc. Chem. Res.* 41:1399 (2008); Seebach & Gardiner, *Acc. Chem. Res.* 41:1366 (2008)) and peptoid helices (Yoo & Kirshenbaum, *Curr. Opin. Chem. Biol.* 12:714 (2008)). Helical surface mimetics utilize conformationally restricted scaffolds with attached functional groups that resemble the i, i+3, i+4, and i+7 pattern of side chain positioning on an α-helix. Surface mimetics typically impart functionality from one face of the helix (Marimganti et al., *Org. Lett.* 11:4418 (2009)), while stabilized peptide helices and foldamers are able to reproduce functionality present on multiple faces of the target helix. A key advantage of helix surface mimicry is that it affords low molecular weight compounds as modulators of protein interactions (Plante et al., *Chem. Commun.* 5091 (2009); Shaginian et al., *J. Am. Chem. Soc.* 131:5564 (2009); Restorp & Rebek, *Bioorg. Med. Chem. Lett.* 18:5909 (2008); Tošovská & Arora, *Org. Lett.* 12:1588 (2010); Buhrlage et al., *ACS Chem. Biol.* 4:335 (2009); Lee et al., *J. Am. Chem. Soc.* 133:676 (2011)).

Mdm2 has a deep and structured binding pocket for p53 (Khoury & Dömling, *Curr. Pharm. Des.* 18(30):4668-78 (2012)). The binding pocket measures only 18 A along the long edge, the size of a typical small molecule (id.). The p53-Mdm2 complex has a "hot spot triad" made up of p53's Trp23, Leu26, and Phe19 (id.). The three hydrophobic amino acids fit into three shape and electrostatic complementary hydrophobic pockets, and the indole nitrogen of p53's Trp23 forms a hydrogen bond with Leu54 of Mdm2 (id.). In fact much of the binding energy resides in these three amino acids (id.). Alanine scan studies show that mutation of any of the three hot-spot amino acids destroys the affinity between p53 and Mdm2 (id.). High affinity Mdm2 antagonists, therefore, should mimic the three amino acids of p53's hot spot triad Trp23, Leu26, and Phe19 (id.).

The present invention is directed to overcoming these and other deficiencies in the art.

SUMMARY OF THE INVENTION

One aspect of the present invention relates to an oligooxopiperazine having a formula selected from the group consisting of:
(i) Formula IA:

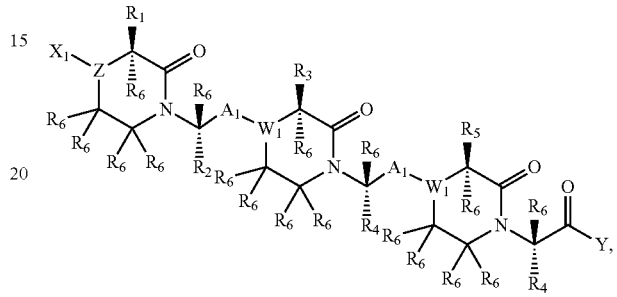

IA wherein:

$R_1$ and $R_2$ are each independently an aromatic amino acid side chain;

$R_3$ is an alkyl or aryl;

$R_4$ and $R_7$ are each independently a solubilizing group, a hydrophobic amino acid side chain, H, $N(R)_2$, OR, halogen, an alkyl, or an aryl; wherein each R is independently H, an alkyl, or an aryl;

$R_5$ is an alkyl;

each $R_6$ is independently H, halogen, an alkyl, or an aryl;

$X_1$ is H, $N(R)_2$, OR, COR', $CO_2R'$, CONR', an alkyl, an aryl, an arylalkyl, a cycloalkyl, a heteroaryl, an amino acid, a peptide of 1 to 10 amino acid residues, a protecting group for protection of an amine, a solubilizing group, a targeting moiety, or a tag; wherein each R is independently H, an alkyl, or an aryl; and wherein R' is H, an alkyl, an aryl, an arylalkyl, a cycloalkyl, a heteroaryl, a targeting moiety, or a tag; with the proviso that $X_1$ is absent when Z is O or S;

Z is N, O, or S;

each $A_1$-$W_1$ is independently:

$$\text{structure}$$

and

Y is OR', COR', $N(R''')_2$, an alkyl, an aryl, an arylalkyl, a cycloalkyl, a heteroaryl, an amino acid, a peptide of 1 to 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, $CO_2R'$, CONR', an alkyl, an aryl, an arylalkyl, a cycloalkyl, a heteroaryl, a targeting moiety, or a tag;

(ii) Formula IB:

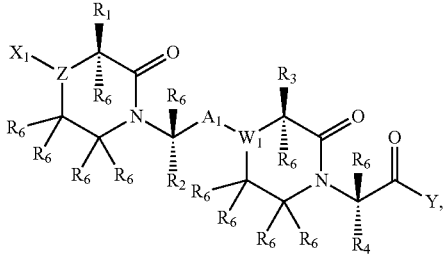

wherein:
$R_1$ and $R_2$ are each independently an aromatic amino acid side chain;
$R_3$ is an alkyl or aryl;
$R_4$ is an alkyl;
each $R_6$ is independently H, halogen, an alkyl, or an aryl;
$X_1$ is H, $N(R)_2$, OR, COR', $CO_2R'$, CONR', an alkyl, an aryl, an arylalkyl, a cycloalkyl, a heteroaryl, an amino acid, a peptide of 1 to 10 amino acid residues, a protecting group for protection of an amine, a solubilizing group, a targeting moiety, or a tag; wherein each R is independently H, an alkyl, or an aryl; and wherein R' is H, an alkyl, an aryl, an arylalkyl, a cycloalkyl, a heteroaryl, a targeting moiety, or a tag; with the proviso that $X_1$ is absent when Z is O or S;
Z is N, O, or S;
$A_1$-$W_1$ is:

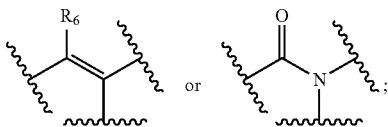

and
Y is OR', COR', $N(R''')_2$, an alkyl, an aryl, an arylalkyl, a cycloalkyl, a heteroaryl, an amino acid, a peptide of 1 to 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, $CO_2R'$, CONR', an alkyl, an aryl, an arylalkyl, a cycloalkyl, a heteroaryl, a targeting moiety, or a tag; and
(iii) Formula IC:

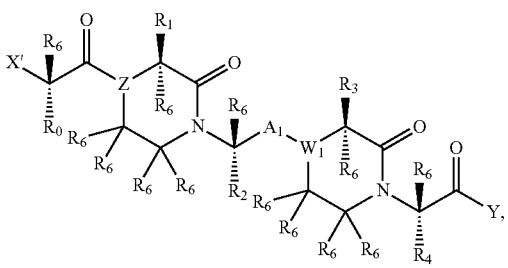

wherein:
$R_0$ and $R_3$ are each independently an aromatic amino acid side chain;
$R_1$ and $R_2$ are each independently a solubilizing group, a hydrophobic amino acid side chain, H, $N(R)_2$, OR, halogen, an alkyl, or an aryl; wherein each R is independently H, an alkyl, or an aryl;
$R_4$ is an alkyl;
each $R_6$ is independently H, halogen, an alkyl, or an aryl;
X' is H, COR', $CO_2R'$, CONR', OR', $N(R'')_2$, an alkyl, an aryl, an arylalkyl, a cycloalkyl, a heteroaryl, a solubilizing group, a targeting moiety, or a tag; wherein R' is H, an alkyl, an aryl, an arylalkyl, a cycloalkyl, a heteroaryl, an amino acid, a peptide of 1 to 10 amino acid residues, a targeting moiety, or a tag; and wherein each R'' is independently H, $CO_2R'$, CONR', an alkyl, an aryl, an arylalkyl, a cycloalkyl, a heteroaryl, a targeting moiety, or a tag;
$A_1$-$W_1$ is:

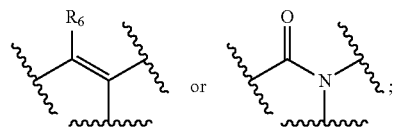

and
Y is OR', COR', $N(R''')_2$, an alkyl, an aryl, an arylalkyl, a cycloalkyl, a heteroaryl, an amino acid, a peptide of 1 to 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, $CO_2R'$, CONR', an alkyl, an aryl, an arylalkyl, a cycloalkyl, a heteroaryl, a targeting moiety, or a tag.

A second aspect of the present invention relates to a method of inhibiting the interaction between p53 and Mdm2 in a cell. This method involves contacting the cell with an oligooxopiperazine of the present invention under conditions effective to inhibit the interaction between p53 and Mdm2.

A third aspect of the present invention relates to a method of treating or preventing in a subject a disorder mediated by interaction of Mdm2 with p53. This method involves administering to the subject an oligooxopiperazine of the present invention under conditions effective to treat or prevent the disorder.

A fourth aspect of the present invention relates to a method of inducing apoptosis of a cell. This method involves contacting the cell with an oligooxopiperazine of the present invention under conditions effective to induce apoptosis of the cell.

A fifth aspect of the present invention relates to a method of decreasing survival and/or proliferation of a cell. This method involves contacting the cell with an oligooxopiperazine of the present invention under conditions effective to decrease survival and/or proliferation of the cell.

A sixth aspect of the present invention relates to a method of increasing activation of p53 in a cell. This method involves contacting the cell with an oligooxopiperazine of the present invention under conditions effective to increase activation of p53 in the cell.

Several examples of nonpeptidic helix mimetics based on aromatic scaffolds have been previously described in the literature along with their potential to target protein-protein interactions. A possible limitation of these classic designs is that they largely consist of achiral aromatic backbones and may not effectively discriminate between chiral protein pockets. Described herein is an approach—based on oligooxopiperazine scaffolds—that features chiral peptide-like backbone and side-chain geometries. The ability of oxopiperazine ligands to target the p53-Mdm2 interaction is described. As part of these efforts the principles of computational protein design were applied to peptidomimetic structure optimization, and computational tools that can design helix mimetics from canonical and noncanonical residue libraries were developed. This provides a streamlined approach for discovering small molecules inhibitors of protein-protein interactions.

BRIEF DESCRIPTION OF THE DRAWINGS

FIGS. 9A-D are QM Ramachandran plots of oxopiperazine dimer and oxopiperazine-amino acid. The oxopiperazine dimer Ramachandran plot of FIG. 9A shows a constrained molecule with a single low energy well near φ and ψ values of −135° and 75°, respectively. FIG. 9B shows the low energy conformation of the oxopiperazine dimer model used in the QM calculations. The oxopiperazine-amino acid Ramachandran plot of FIG. 9C shows a more flexible molecule than the oxopiperazine dimer, with a very broad low energy well. FIG. 9D shows the low energy conformation of the oxopiperazine-amino acid model with φ and ψ values of −75° and 150°, respectively. A comparison between the plots in FIG. 9A and FIG. 9C provides additional support for the hypothesis that the oxopiperazine dimer is a conformationally stable scaffold.

FIG. 10 illustrates the docking of an oxopiperazine scaffold in the p53 binding pocket of Mdm2 The relative positioning of the oxopiperazine dimer side chains $R_1$-$R_4$ and p53 hotspot residues Phe19, Trp23, and Leu26 are shown within the protein pocket.

FIG. 11A shows mimetic 5 in its entirety. The binding modes of Phe, Trp, and Leu residues ($R_1$, $R_2$, and $R_4$ positions) of 5 are shown in FIGS. 11B-D, respectively.

FIG. 12 is a graph of Rosetta binding energy correlated with experimental $K_d$. Data points are taken from Table 5, infra, and the correlation coefficient was calculated using Python's scipy.stats.stats.pearsonr function. To provide a realistic comparison of Rosetta's binding energy to experimental $K_d$ values, two data points were removed, KWFL and FWAL. The KWFL data point was removed because manual inspection suggested the design would be a poor inhibitor (see FIGS. 13A-B). FWAL was removed because the residue at the $3^{rd}$ position, although important in terms of its affect on $K_d$, has no contacts with the Mdm2 pocket in the structural model and therefore Rosetta cannot discriminate substitutions at this position.

FIGS. 13A-B relate to the predicted conformation of oxopiperazine 7 (KWFL) in complex with Mdm2 Upon manual inspection of the KWFL design, the lysine in the $1^{st}$ position of the oxopiperazine does not occupy the same pocket as the p53 Phe19. This suggests that oxopiperazine 7 is a poor competitor with p53 and provides a clear explanation of the discrepancy between the predicted Rosetta binding energy and the experimental $K_d$. FIG. 13A is a surface representation. FIG. 13B is a ribbon representation.

FIGS. 14A-E relate to the examination of the N-terminal residue-binding pocket in Mdm2 FIG. 14A shows that the phenylalanine residue at the $R_1$ position of mimetic 5 resides in a flexible pocket consisting of Ile61, Met62, Tyr67, and Gln72 of Mdm2 FIGS. 14B-E show the predicted orientations of phenylalanine (FIG. 14B) and analogs naphthylalanine (FIG. 14C), tyrosine (FIG. 14D), and 3-chlorophenylalanine (FIG. 14E). The electrostatic surface of Mdm2 is modeled by Pymol.

FIG. 16A shows the overlaid spectra of Mdm2 (blue), Mdm2-F(3-Cl)WFL 18 (1:0.2, red), and Mdm2-F(3-Cl) WFL 18 (1:0.5, green). Mdm2 assignments are as described in Uhrinova et al., *J. Mol. Biol.* 350:587 (2005), and Stoll et al., *J. Biomolec. NMR* 17:91 (2000). FIG. 16B is a mean chemical shift difference (ΔδNH) plot depicting changes in residues (Williamson, *Prog. Nucl. Magnetic Res. Spectr.* 73:1 (2013)).

DETAILED DESCRIPTION OF THE INVENTION

Figure 1:
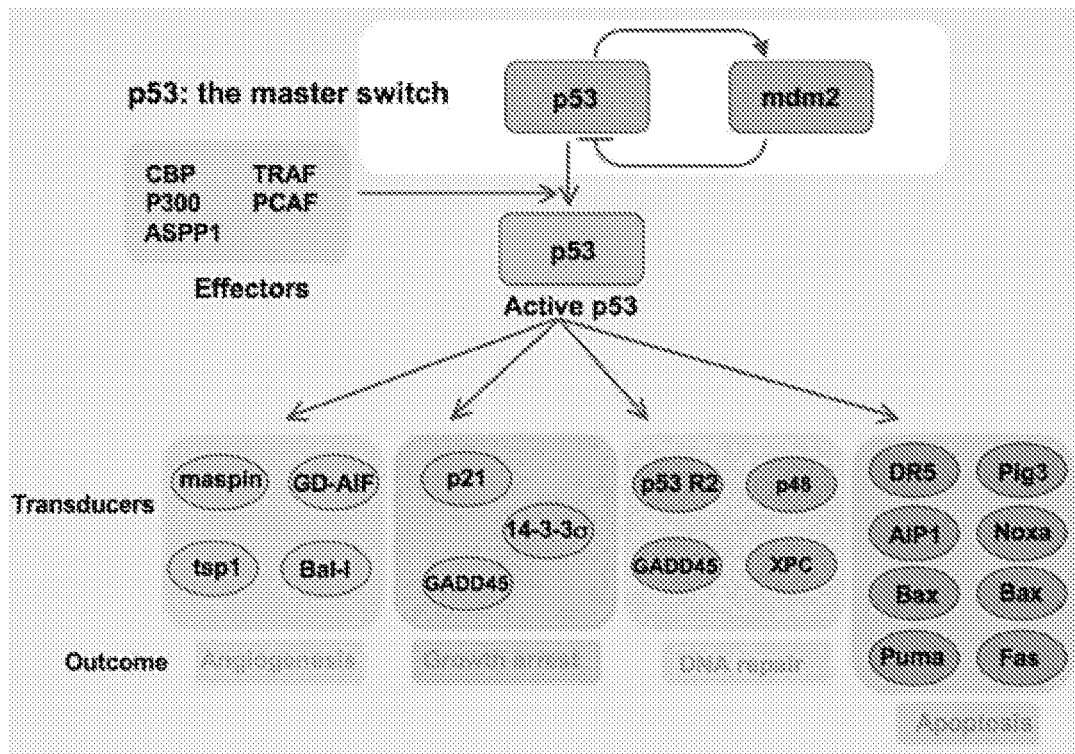
FIG. 1 is a schematic diagram of p53 regulation by Mdm2 showing the stress signals that activate the pathway, mediators that detect the signals, and downstream transcriptional activators affected by the pathway and their outcomes (Thierry Soussi, *p53 Information*, THE TP53 WEB SITE, http://p53.free.fr/p53_info/p53_Pathways.html (last visited Jul. 31, 2013)).

Described herein are computational design, solid phase synthesis, and detailed experimental characterization of multiple oxopiperazine-based ligands for a model protein receptor, Mdm2 This computational approach for designing ligands to target a specific interface includes canonical and noncanonical amino acid residues. The advantage of oxopiperazine-based scaffolds is that they offer chiral backbones and can be easily assembled from α-amino acids, allowing rapid diversification of the scaffold. Using the combined rational design and computational optimization protocol illustrated in FIG. 2, high affinity ligands for Mdm2 were developed. The protein binding affinity for each compound was analyzed using a fluorescence competition assay, suggesting that the ligands bind the targeted region on the surface of Mdm2 The Mdm2 binding site of the optimized mimetic was further confirmed by $^1$H-$^{15}$N HSQC NMR spectroscopy experiments. It is expected that these mimetics can be used to modify the p53-Mdm2 interaction.

One aspect of the present invention relates to an oligooxopiperazine having a formula selected from the group consisting of:

(i) Formula IA:

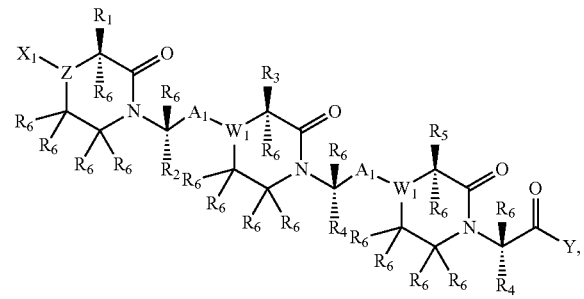

wherein:
$R_1$ and $R_2$ are each independently an aromatic amino acid side chain;
$R_3$ is an alkyl or aryl;
$R_4$ and $R_7$ are each independently a solubilizing group, a hydrophobic amino acid side chain, H, N(R)$_2$, OR, halogen, an alkyl, or an aryl; wherein each R is independently H, an alkyl, or an aryl;
$R_5$ is an alkyl;
each $R_6$ is independently H, halogen, an alkyl, or an aryl;
$X_1$ is H, N(R)$_2$, OR, COR', CO$_2$R', CONR', an alkyl, an aryl, an arylalkyl, a cycloalkyl, a heteroaryl, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of an amine, a solubilizing group, a targeting moiety, or a tag; wherein each R is independently H, an alkyl, or an aryl; and wherein R' is H, an alkyl, an aryl, an arylalkyl, a cycloalkyl, a heteroaryl, a targeting moiety, or a tag; with the proviso that $X_1$ is absent when Z is O or S;
Z is N, O, or S;
each $A_1$-$W_1$ is independently:

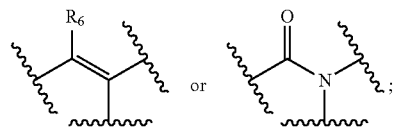

and
Y is OR', COR', N(R''')$_2$, an alkyl, an aryl, an arylalkyl, a cycloalkyl, a heteroaryl, an amino acid, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, CO$_2$R', CONR', an alkyl, an aryl, an arylalkyl, a cycloalkyl, a heteroaryl, a targeting moiety, or a tag;

(ii) Formula IB:

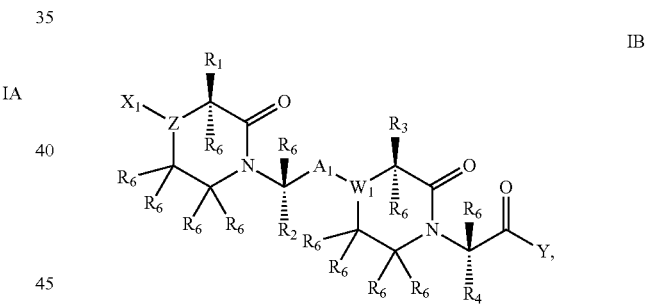

wherein:
$R_1$ and $R_2$ are each independently an aromatic amino acid side chain;
$R_3$ is an alkyl or aryl;
$R_4$ is an alkyl;
each $R_6$ is independently H, halogen, an alkyl, or an aryl;
$X_1$ is H, N(R)$_2$, OR, COR', CO$_2$R', CONR', an alkyl, an aryl, an arylalkyl, a cycloalkyl, a heteroaryl, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of an amine, a solubilizing group, a targeting moiety, or a tag; wherein each R is independently H, an alkyl, or an aryl; and wherein R' is H, an alkyl, an aryl, an arylalkyl, a cycloalkyl, a heteroaryl, a targeting moiety, or a tag; with the proviso that $X_1$ is absent when Z is O or S;
Z is N, O, or S;

$A_1-W_1$ is:

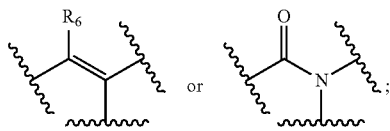

and

Y is OR', COR', N(R''')$_2$, an alkyl, an aryl, an arylalkyl, a cycloalkyl, a heteroaryl, an amino acid, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, CO$_2$R', CONR', an alkyl, an aryl, an arylalkyl, a cycloalkyl, a heteroaryl, a targeting moiety, or a tag; and (iii) Formula IC:

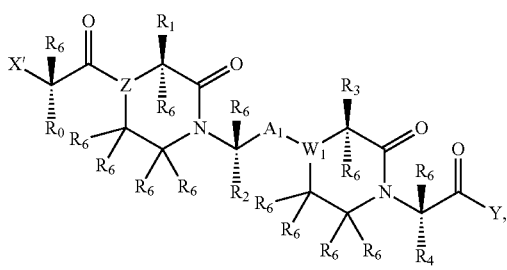

IC wherein:

R$_0$ and R$_3$ are each independently an aromatic amino acid side chain;

R$_1$ and R$_2$ are each independently a solubilizing group, a hydrophobic amino acid side chain, H, N(R)$_2$, OR, halogen, an alkyl, or an aryl; wherein each R is independently H, an alkyl, or an aryl;

R$_4$ is an alkyl;

each R$_6$ is independently H, halogen, an alkyl, or an aryl;

X' is H, COR', CO$_2$R', CONR', OR', N(R'')$_2$, an alkyl, an aryl, an arylalkyl, a cycloalkyl, a heteroaryl, a solubilizing group, a targeting moiety, or a tag; wherein R' is H, an alkyl, an aryl, an arylalkyl, a cycloalkyl, a heteroaryl, an amino acid residue, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a targeting moiety, or a tag; and wherein each R'' is independently H, CO$_2$R', CONR', an alkyl, an aryl, an arylalkyl, a cycloalkyl, a heteroaryl, a targeting moiety, or a tag;

$A_1-W_1$ is:

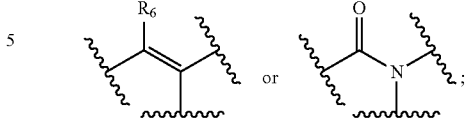

and

Y is OR', COR', N(R''')$_2$, an alkyl, an aryl, an arylalkyl, a cycloalkyl, a heteroaryl, an amino acid, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, CO$_2$R', CONR', an alkyl, an aryl, an arylalkyl, a cycloalkyl, a heteroaryl, a targeting moiety, or a tag.

Amino acids according to this and all aspects of the present invention can be any natural or nonnatural amino acid, including alpha amino acids, beta amino acids, gamma amino acids, L-amino acids, D-amino acids, and halogenated amino acids.

Amino acid side chains according to this and all aspects of the present invention can be any amino acid side chain from natural or nonnatural amino acids, including from alpha amino acids, beta amino acids, gamma amino acids, L-amino acids, D-amino acids, and halogenated amino acids. Aromatic amino acid side chains are well known in the art and include, for example, phenylalanine, tryptophan, tyrosine, 3-chloro-phenylalanine, naphthaline, 3-methyl-phenylalanine, 4-chloro-phenylalanine, and (O—R)-tyrosine. Hydrophobic amino acid side chains are well known in the art and include, for example, phenylalanine, tryptophan, leucine, alanine, isoleuceine, valine, tyrosine, norleucine, 3-chloro-phenylalanine, naphthaline, 3-methyl-phenylalanine, 4-chloro-phenylalanine, and (O—R)-tyrosine.

Solubilizing groups according to this and all aspects of the present invention include, without limitation, lysine, arginine, and poly(ethylene glycol).

As used herein, the term "alkyl" means an aliphatic hydrocarbon group which may be straight or branched having about 1 to about 6 carbon atoms in the chain. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

As used herein, the term "cycloalkyl" refers to a non-aromatic saturated or unsaturated mono- or polycyclic ring system which may contain 3 to 6 carbon atoms, and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

As used herein, the term "aryl" refers to an aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylalkyl" refers to a radical of the formula —$R^aR^b$ where $R^a$ is an alkyl radical as defined above and $R^b$ is an aryl radical as defined above. The alkyl radical and the cycloalkyl radical may be optionally substituted as defined above.

As used herein, "heteroaryl" refers to an aromatic ring radical which consists of carbon atoms and from one to five heteroatoms selected from the group consisting of nitrogen, oxygen, and sulfur. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl. Additional heteroaryls are described in COMPREHENSIVE HETEROCYCLIC CHEMISTRY: THE STRUCTURE, REACTIONS, SYNTHESIS AND USE OF HETEROCYCLIC COMPOUNDS (Katritzky et al. eds., 1984), which is hereby incorporated by reference in its entirety.

The oligooxopiperazines of Formula IA, Formula IB, and Formula IC may comprise a protecting group that is suitable for the protection of an amine or a carboxylic acid. Such protecting groups function primarily to protect or mask the reactivity of functional groups. Protecting groups that are suitable for the protection of an amine group are well known in the art, including without limitation, carbamates, amides, N-alkyl and N-aryl amines, imine derivatives, enamine derivatives, and N-hetero atom derivatives as described by THEODORA W. GREENE & PETER G. M. WUTS, PROTECTIVE GROUPS IN ORGANIC SYNTHESIS 494-615 (1999), which is hereby incorporated by reference in its entirety. Protecting groups that are suitable for the protection of a carboxylic acid are also well known in the art. Suitable carboxylic acid protecting groups include, without limitation, esters (e.g., substituted methyl esters, 2-substituted ethyl esters, 2,6-dialkylphenyl esters, substituted benzyl esters, silyl esters, and stannyl esters), amides, and hydrazides, as described by THEODORA W. GREENE & PETER G. M. WUTS, PROTECTIVE GROUPS IN ORGANIC SYNTHESIS 372-450 (1999), which is hereby incorporated by reference in its entirety. Methods of protecting and deprotecting amine and carboxylic acids vary depending on the chosen protecting group; however, these methods are well known in the art and described in THEODORA W. GREENE & PETER G. M. WUTS, PROTECTIVE GROUPS IN ORGANIC SYNTHESIS 372-450, 494-615 (1999), which is hereby incorporated by reference in its entirety.

A "tag" as used herein includes any labeling moiety that facilitates the detection, quantitation, separation, and/or purification of the compounds of the present invention. Suitable tags include purification tags, radioactive or fluorescent labels, and enzymatic tags.

Purification tags, such as poly-histidine ($His_6$-), a glutathione-S-transferase (GST), or maltose-binding protein (MBP-), can assist in compound purification or separation but can later be removed, i.e., cleaved from the compound following recovery. Protease-specific cleavage sites can be used to facilitate the removal of the purification tag. The desired product can be purified further to remove the cleaved purification tags.

Other suitable tags include radioactive labels, such as, $^{125}I$, $^{131}I$, $^{111}In$, or $^{99}TC$. Methods of radiolabeling compounds are known in the art and described in U.S. Pat. No. 5,830,431 to Srinivasan et al., which is hereby incorporated by reference in its entirety. Radioactivity is detected and quantified using a scintillation counter or autoradiography. Alternatively, the compound can be conjugated to a fluorescent tag. Suitable fluorescent tags include, without limitation, chelates (europium chelates), fluorescein and its derivatives, rhodamine and its derivatives, dansyl, Lissamine, phycoerythrin, and Texas Red. The fluorescent labels can be conjugated to the compounds using techniques disclosed in CURRENT PROTOCOLS IN IMMUNOLOGY (Coligen et al. eds., 1991), which is hereby incorporated by reference in its entirety. Fluorescence can be detected and quantified using a fluorometer.

Enzymatic tags generally catalyze a chemical alteration of a chromogenic substrate, which can be measured using various techniques. For example, the enzyme may catalyze a color change in a substrate, which can be measured spectrophotometrically. Alternatively, the enzyme may alter the fluorescence or chemiluminescence of the substrate. Examples of suitable enzymatic tags include luciferases (e.g., firefly luciferase and bacterial luciferase; see e.g., U.S. Pat. No. 4,737,456 to Weng et al., which is hereby incorporated by reference in its entirety), luciferin, 2,3-dihydrophthalazinediones, malate dehydrogenase, urease, peroxidases (e.g., horseradish peroxidase), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase, microperoxidase, and the like. Techniques for conjugating enzymes to proteins and peptides are described in O'Sullivan et al., *Methods for the Preparation of Enzyme—Antibody Conjugates for Use in Enzyme Immunoassay, in* METHODS IN ENZYMOLOGY 147-66 (Langone et al. eds., 1981), which is hereby incorporated by reference in its entirety.

A targeting moiety according to the present invention functions to (i) promote the cellular uptake of the compound, (ii) target the compound to a particular cell or tissue type (e.g., signaling peptide sequence), or (iii) target the compound to a specific sub-cellular localization after cellular uptake (e.g., transport peptide sequence).

To promote the cellular uptake of a compound of the present invention, the targeting moiety may be a cell penetrating peptide (CPP). CPPs translocate across the plasma membrane of eukaryotic cells by a seemingly energy-independent pathway and have been used successfully for intracellular delivery of macromolecules, including antibodies, peptides, proteins, and nucleic acids, with molecular weights several times greater than their own. Several commonly used CPPs, including polyarginines, transportant, protamine, maurocalcine, and M918, are suitable targeting moieties for use in the present invention and are well known in the art (see Stewart et al., *Organic Biomolecular Chem.* 6:2242-2255 (2008), which is hereby incorporated by reference in its entirety). Additionally, methods of making CPP are described in U.S. Patent Application Publication No. 20080234183 to Hallbrink et al., which is hereby incorporated by reference in its entirety.

Another suitable targeting moiety useful for enhancing the cellular uptake of a compound is an "importation competent" signal peptide as disclosed by U.S. Pat. No. 6,043, 339 to Lin et al., which is hereby incorporated by reference in its entirety. An importation competent signal peptide is generally about 10 to about 50 amino acid residues in length—typically hydrophobic residues—that render the compound capable of penetrating through the cell membrane from outside the cell to the interior of the cell. An exemplary importation competent signal peptide includes the signal peptide from Kaposi fibroblast growth factor (see U.S. Pat. No. 6,043,339 to Lin et al., which is hereby incorporated by reference in its entirety). Other suitable peptide sequences can be selected from the SIGPEP database (see von Heijne G., *Protein Seq. Data Anal.* 1(1):41-42 (1987), which is hereby incorporated by reference in its entirety).

Another suitable targeting moiety is a signal peptide sequence capable of targeting the compounds of the present invention to a particular tissue or cell type. The signaling peptide can include at least a portion of a ligand binding protein. Suitable ligand binding proteins include high-affinity antibody fragments (e.g., Fab, Fab' and F(ab')$_2$, single-chain Fv antibody fragments), nanobodies or nanobody fragments, fluorobodies, or aptamers. Other ligand binding proteins include biotin-binding proteins, lipid-binding proteins, periplasmic binding proteins, lectins, serum albumins, enzymes, phosphate and sulfate binding proteins, immunophilins, metallothionein, or various other receptor proteins. For cell specific targeting, the signaling peptide is preferably a ligand binding domain of a cell specific membrane receptor. Thus, when the modified compound is delivered intravenously or otherwise introduced into blood or lymph, the compound will adsorb to the targeted cell, and the targeted cell will internalize the compound. For example, if the target cell is a cancer cell, the compound may be conjugated to an anti-C3B(I) antibody as disclosed by U.S. Pat. No. 6,572,856 to Taylor et al., which is hereby incorporated by reference in its entirety. Alternatively, the compound may be conjugated to an alphafeto protein receptor as disclosed by U.S. Pat. No. 6,514,685 to Moro, which is hereby incorporated by reference in its entirety, or to a monoclonal GAH antibody as disclosed by U.S. Pat. No. 5,837,845 to Hosokawa, which is hereby incorporated by reference in its entirety. For targeting a compound to a cardiac cell, the compound may be conjugated to an antibody recognizing elastin microfibril interfacer (EMILIN2) (Van Hoof et al., *J Proteom Res* 9:1610-18 (2010), which is hereby incorporated by reference in its entirety), cardiac troponin I, connexin-43, or any cardiac cell-surface membrane receptor that is known in the art. For targeting a compound to a hepatic cell, the signaling peptide may include a ligand domain specific to the hepatocyte-specific asialoglycoprotein receptor. Methods of preparing such chimeric proteins and peptides are described in U.S. Pat. No. 5,817,789 to Heartlein et al., which is hereby incorporated by reference in its entirety.

Another suitable targeting moiety is a transport peptide that directs intracellular compartmentalization of the compound once it is internalized by a target cell or tissue. For transport to the endoplasmic reticulum (ER), for example, the compound can be conjugated to an ER transport peptide sequence. A number of such signal peptides are known in the art, including the signal peptide MMSFVSLLLVGIL-FYATEAEQLTKCEVFQ (SEQ ID NO: 1). Other suitable ER signal peptides include the N-terminus endoplasmic reticulum targeting sequence of the enzyme 17β-hydroxysteroid dehydrogenase type 11 (Horiguchi et al., *Arch. Biochem. Biophys.* 479(2):121-30 (2008), which is hereby incorporated by reference in its entirety), or any of the ER signaling peptides (including the nucleic acid sequences encoding the ER signal peptides) disclosed in U.S. Patent Application Publication No. 20080250515 to Reed et al., which is hereby incorporated by reference in its entirety. Additionally, the compound of the present invention can contain an ER retention signal, such as the retention signal KEDL (SEQ ID NO: 2). Methods of modifying the compounds of the present invention to incorporate transport peptides for localization of the compounds to the ER can be carried out as described in U.S. Patent Application Publication No. 20080250515 to Reed et al., which is hereby incorporated by reference in its entirety.

For transport to the nucleus, the compounds of the present invention can include a nuclear localization transport signal. Suitable nuclear transport peptide sequences are known in the art, including the nuclear transport peptide PPKKKRKV (SEQ ID NO:3). Other nuclear localization transport signals include, for example, the nuclear localization sequence of acidic fibroblast growth factor and the nuclear localization sequence of the transcription factor NF-KB p50 as disclosed by U.S. Pat. No. 6,043,339 to Lin et al., which is hereby incorporated by reference in its entirety. Other nuclear localization peptide sequences known in the art are also suitable for use in the compounds of the present invention.

Suitable transport peptide sequences for targeting to the mitochondria include MLSLRQSIRFFKPATRTLCSSRYLL (SEQ ID NO: 4). Other suitable transport peptide sequences suitable for selectively targeting the compounds of the present invention to the mitochondria are disclosed in U.S. Patent Application Publication No. 20070161544 to Wipf, which is hereby incorporated by reference in its entirety.

In one embodiment of the present invention, the oligooxopiperazine has a formula of Formula IA:

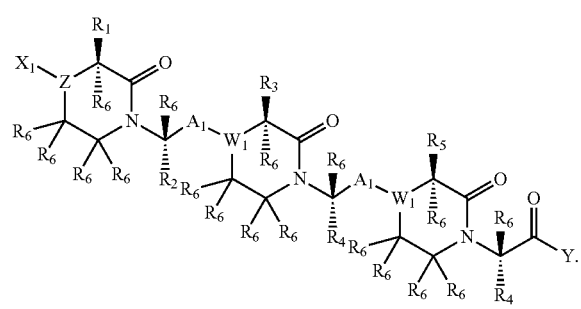

IA

In a preferred embodiment, $R_1$, $R_2$, and $R_5$ are each independently a side chain of an amino acid selected from the group consisting of Ala, Leu, Phe, Met, Trp, Ile, Val, Ser, Tyr, Tyr(O—R'), Nap, 2-halo-Phe, 3-halo-Phe, 4-halo-Phe, 2-R'-Phe, 3-R'-Phe, and 4-R'-Phe; $R_3$ and $R_7$ are each independently a side chain of an amino acid selected from the group consisting of Ala, Leu, Phe, Met, Trp, Ile, Val, Ser, Tyr, Asp, Glu, Asn, Gln, Cys, His, Thr, and Arg; $R_4$ is a side chain of an amino acid selected from the group consisting of Leu, Ile, Val, Ala, Ser, Met, and Nle; and Y is OH, OR', NHR', NR'$_2$, or NH$_2$.

In another embodiment of the present invention, the oligooxopiperazine has a formula of Formula IB:

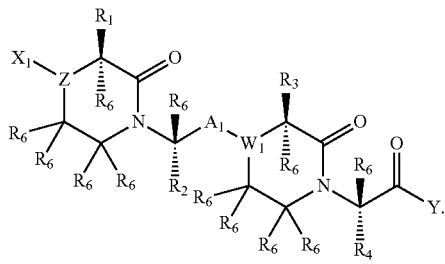

In a preferred embodiment, $R_1$, $R_2$, and $R_3$ are each independently a side chain of an amino acid selected from the group consisting of Ala, Leu, Phe, Met, Trp, Ile, Val, Ser, Tyr, Tyr(O—R'), Nap, 2-halo-Phe, 3-halo-Phe, 4-halo-Phe, 2-R'-Phe, 3-R'-Phe, and 4-R'-Phe; $R_4$ is a side chain of an amino acid selected from the group consisting of Leu, Ile, Val, Ala, Ser, Met, and Nle; and Y is OH, OR', NHR', NR'$_2$, or NH$_2$.

In another embodiment of the present invention, the oligooxopiperazine has a formula of Formula IC:

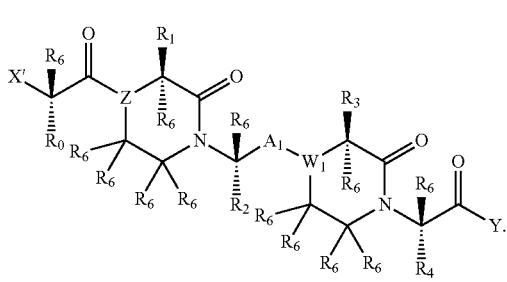

In a preferred embodiment, $R_0$, $R_2$, and $R_3$ are each independently a side chain of an amino acid selected from the group consisting of Ala, Leu, Phe, Met, Trp, Ile, Val, Ser, Tyr, Tyr(O—R'), Nap, 2-halo-Phe, 3-halo-Phe, 4-halo-Phe, 2-R'-Phe, 3-R'-Phe, and 4-R'-Phe; $R_1$ is a side chain of an amino acid selected from the group consisting of Ala, Leu, Phe, Met, Trp, Ile, Val, Ser, Tyr, Asp, Glu, Asn, Gln, Cys, His, Thr, and Arg; $R_4$ is a side chain of an amino acid selected from the group consisting of Leu, Ile, Val, Ala, Ser, Met, and Nle; and Y is OH, OR', NHR', NR'$_2$, or NH$_2$.

Oligooxopiperazines of the present invention may be made using methods known in the art. Suitable methods include those described in U.S. patent application Ser. No. 12/917,176, which is hereby incorporated by reference in its entirety.

Another aspect of the present invention relates to pharmaceutical formulations comprising any of the above described oligooxoperazines of the present invention and a pharmaceutically acceptable carrier. Acceptable pharmaceutical carriers include solutions, suspensions, emulsions, excipients, powders, or stabilizers. The carrier should be suitable for the desired mode of delivery.

In addition, the pharmaceutical formulations of the present invention may further comprise one or more pharmaceutically acceptable diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

Another aspect of the present invention relates to a method of inhibiting the interaction between p53 and Mdm2 in a cell. This method involves contacting the cell with an oligooxopiperazine of the present invention under conditions effective to inhibit the interaction between p53 and Mdm2.

Suitable examples of Mdm2 according to this and all aspects of the present invention, include, without limitation, UniProtKB Accession Numbers P23804 (mouse), Q00987 (human), P56950 (dog), P56273 (African clawed frog), O42354 (zebrafish), P56951 (horse), Q60524 (Golden hamster), Q7YRZ8 (cat), and homologs of each of these proteins.

Another aspect of the present invention relates to a method of treating or preventing in a subject a disorder mediated by interaction of Mdm2 with p53, the method comprising administering to the subject an oligooxopiperazine of the present invention under conditions effective to treat or prevent the disorder.

The present invention provides for both prophylactic and therapeutic methods of treating a subject at risk of (or susceptible to) a disorder or having a disorder associated with reduced p53 activity. This is because the oligooxopiperazines are expected to act as inhibitors of p53 binding to Mdm2 As used herein, the term "treatment" is defined as the application or administration of a therapeutic agent to a patient, or application or administration of a therapeutic agent to an isolated tissue or cell line from a patient, who has a disease, a symptom of disease, or a predisposition toward a disease, with the purpose to cure, heal, alleviate, relieve, alter, remedy, ameliorate, improve, or affect the disease, the symptoms of disease, or the predisposition toward disease.

Disorders mediated by interaction of p53 and Mdm2 include, for example, cellular proliferative and/or differentiative disorders, hyperproliferative conditions, and neoplastic conditions. Exemplary disorders include cancers (e.g., carcinoma, sarcoma, or metastatic disorders), hematopoietic neoplastic disorders, and cellular proliferative and/or differentiative disorders of the breast. In a preferred embodiment, the disorder is cancer.

Cancers according to this aspect of the present invention include, without limitation, benign tumor of the skin (e.g., keratoacanthomas), bladder carcinoma, brain tumors, breast carcinoma (e.g., advanced breast cancer), cervical carcinoma, colon cancers (e.g., colorectal carcinomas, such as, for example, colon adenocarcinoma and colon adenoma), endometrial carcinoma, epidermal carcinoma, esophageal cancer, gastric carcinoma, gliomas, head and neck cancer, hematopoietic tumors of lymphoid lineage (e.g., T cell cancers and B cell cancers, acute lymphocytic leukemia, B-cell lymphoma, Burkitt's lymphoma, and non-Hodgkin's lymphoma), Hodgkin's disease, kidney carcinoma, lung cancer (e.g., adenocarcinoma and including non-small cell lung cancer), medulloblastoma, melanomas, mucoepidermoid carcinoma, myelodysplastic syndrome (MD S), myeloid leukemias (e.g., acute myelogenous leukemia (AML)), nasopharyngeal cancer, neuroblastomas, oral squamous carcinoma, osteosarcoma, ovary carcinoma, pancreatic cancers (e.g., pancreatic carcinoma such as, for example exocrine pancreatic carcinoma), prostate cancer including the advanced disease, retinoblastoma, teratocarcinomas, testicular cancers, thyroid follicular cancer, tongue carcinoma, and tumors of mesenchymal origin (e.g., fibrosarcomas and rhabdomyosarcomas)

Hematopoietic neoplastic disorders include diseases involving hyperplastic/neoplastic cells of hematopoietic origin, e.g., arising from myeloid, lymphoid, or erythroid lineages, or precursor cells thereof. Exemplary disorders include acute leukemias, e.g., erythroblastic leukemia and acute megakaryoblastic leukemia. Additional exemplary myeloid disorders include, but are not limited to, acute promyeloid leukemia (APML), acute myelogenous leukemia (AML), and chronic myelogenous leukemia (CML) (reviewed in Vaickus, *Crit. Rev. Oncol./Hemotol.* 11:267-97 (1991), which is hereby incorporated by reference in its entirety); lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), multiple mylenoma, hairy cell leukemia (HLL), and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease, and Reed-Sternberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, invasive papillary carcinoma, and miscellaneous malignant neoplasms. Disorders in the male breast include, but are not limited to, gynecomastia and carcinoma.

The subject according to this aspect of the present invention can be, for example, any vertebrate, e.g., mammals, fish, reptiles, birds, and amphibians. Suitable mammals include, for example, primates, felines, canines, rodents (e.g., mice and rats), and livestock (e.g., cattle, sheep, pigs, goats, and horses). In a preferred embodiment, the subject is a human subject.

The compounds of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Yet another aspect of the present invention relates to a method of inducing apoptosis of a cell, the method comprising contacting the cell with an oligooxopiperazine of the present invention under conditions effective to induce apoptosis of the cell.

Suitable cells according to this and all aspects of the present invention include, without limitation, any vertebrate cell, e.g., mammalian, ichthian, reptilian, avian, and amphibian cells. Suitable mammalian cells include, for example, those of primates, felines, canines, rodents (e.g., mice and rats), and livestock (e.g., cattle, sheep, pigs, goats, and horses). In a preferred embodiment, the cells are human cells. In at least one embodiment, the cells are cancerous or are contained in the endothelial vasculature of a tissue that contains cancerous cells. Suitable cancer cells include, e.g., B cells, bladder cells, bone cells, brain cells, breast cells, cervical cells, colon cells, colorectal cells, endometrial cells, epidermal cells, epithelial cells, erythroid cells, esophageal cells, gastric cells, gliomal cells, hematopoietic cells, kidney cells, lung cells, lymphoid cells, mesenchymal cells, mucoepidermoid cells, myeloid cells, nasopharyngeal cells, neural cells, oral squamous cells, ovarian cells, pancreatic cells, prostate cells, skin cells, stromal cells, T cells, testicular cells, thyroid cells, and tongue cells.

Another aspect of the present invention relates to a method of decreasing survival and/or proliferation of a cell, the method comprising contacting the cell with an oligooxopiperazine of the present invention under conditions effective to decrease survival and/or proliferation of the cell.

Suitable cells include those noted above.

Another aspect of the present invention relates to a method of increasing activation of p53 in a cell. This method involves contacting the cell with an oligooxopiperazine of the present invention under conditions effective to increase activation of p53 in the cell.

Suitable cells include those noted above.

In all aspects of the present invention directed to methods involving contacting a cell with one or more oligooxopiperazines, contacting can be carried out using methods that will be apparent to the skilled artisan, and can be done in vitro or in vivo.

One approach for delivering agents into cells involves the use of liposomes. Basically, this involves providing a liposome which includes agent(s) to be delivered, and then contacting the target cell, tissue, or organ with the liposomes under conditions effective for delivery of the agent into the cell, tissue, or organ.

This liposome delivery system can also be made to accumulate at a target organ, tissue, or cell via active targeting (e.g., by incorporating an antibody or hormone on the surface of the liposomal vehicle). This can be achieved according to known methods.

An alternative approach for delivery of protein- or polypeptide-containing agents (e.g., oligooxopiperazines of the present invention containing one or more protein or polypeptide side chains) involves the conjugation of the desired agent to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of agents involves preparation of chimeric agents according to U.S. Pat. No. 5,817,789 to Heartlein et al., which is hereby incorporated by reference in its entirety. The chimeric agent can include a ligand domain and the agent. The ligand domain is specific for receptors located on a target cell. Thus, when the chimeric agent is delivered intravenously or otherwise introduced into blood or lymph, the chimeric agent will adsorb to the targeted cell, and the targeted cell will internalize the chimeric agent.

Oligooxopiperazines of the present invention may be delivered directly to the targeted cell/tissue/organ.

Additionally and/or alternatively, the oligooxopiperazines may be administered to a non-targeted area along with one or more agents that facilitate migration of the oligooxopiperazines to (and/or uptake by) a targeted tissue, organ, or cell. As will be apparent to one of ordinary skill in the art, the oligooxopiperazine itself can be modified to facilitate its transport to a target tissue, organ, or cell, including its transport across the blood-brain barrier; and/or to facilitate its uptake by a target cell (e.g., its transport across cell membranes).

In vivo administration can be accomplished either via systemic administration to the subject or via targeted administration to affected tissues, organs, and/or cells, as described above. Typically, the therapeutic agent (i.e., an oligooxopiperazine of the present invention) will be administered to a patient in a vehicle that delivers the therapeutic agent(s) to the target cell, tissue, or organ. Typically, the therapeutic agent will be administered as a pharmaceutical formulation, such as those described above.

Exemplary routes of administration include, without limitation, orally, topically, transdermally, parenterally, subcutaneously, intravenously, intramuscularly, intraperitoneally, intraventricularly, and intralesionally; by intratracheal inoculation, aspiration, airway instillation, aerosolization, nebulization, intranasal instillation, oral or nasogastric instillation, intraperitoneal injection, intravascular injection, intravenous injection, intra-arterial injection (such as via the pulmonary artery), intramuscular injection, and intrapleural instillation; by application to mucous membranes (such as that of the nose, throat, bronchial tubes, genitals, and/or anus); and by implantation of a sustained release vehicle.

For use as aerosols, an oligooxopiperazine of the present invention in solution or suspension may be packaged in a pressurized aerosol container together with suitable propellants, for example, hydrocarbon propellants like propane, butane, or isobutane with conventional adjuvants. The oligooxopiperazines of the present invention also may be administered in a non-pressurized form.

Exemplary delivery devices include, without limitation, nebulizers, atomizers, liposomes (including both active and passive drug delivery techniques) (Wang & Huang, *Proc. Nat'l Acad. Sci. USA* 84:7851-5 (1987); Bangham et al., *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; U.S. Pat. No. 5,059,421 to Loughrey et al.; Wolff et al., *Biochim. Biophys. Acta* 802:259-73 (1984), each of which is hereby incorporated by reference in its entirety), transdermal patches, implants, implantable or injectable protein depot compositions, and syringes. Other delivery systems which are known to those of skill in the art can also be employed to achieve the desired delivery of the oligooxopiperazine to the desired organ, tissue, or cells in vivo.

Contacting (including in vivo administration) can be carried out as frequently as required and for a duration that is suitable to provide the desired effect. For example, contacting can be carried out once or multiple times, and in vivo administration can be carried out with a single sustained-release dosage formulation or with multiple (e.g., daily) doses.

The amount to be administered will, of course, vary depending upon the particular conditions and treatment regimen. The amount/dose required to obtain the desired effect may vary depending on the agent, formulation, cell type, culture conditions (for ex vivo embodiments), the duration for which treatment is desired, and, for in vivo embodiments, the individual to whom the agent is administered.

Effective amounts can be determined empirically by those of skill in the art. For example, this may involve assays in which varying amounts of the oligooxopiperazine of the invention are administered to cells in culture and the concentration effective for obtaining the desired result is calculated. Determination of effective amounts for in vivo administration may also involve in vitro assays in which varying doses of agent are administered to cells in culture and the concentration of agent effective for achieving the desired result is determined in order to calculate the concentration required in vivo. Effective amounts may also be based on in vivo animal studies.

The present invention may be further illustrated by reference to the following examples.

EXAMPLES

Example 1—Materials and Methods: General Materials and Methods

Commercial-grade reagents and solvents were used without further purification except as indicated. All reactions were stirred magnetically or mechanically shaken; moisture-sensitive reactions were performed under nitrogen atmosphere. Reverse-phase HPLC experiments were conducted with 0.1% aqueous trifluoroacetic acid and 0.1% trifluoroacetic acid in acetonitrile buffers as eluents on $C_{18}$ reversed-phase columns using a Beckman Coulter HPLC equipped with a System Gold 168 Diode array detector. ESIMS data was obtained on an Agilent 1100 series LC/MSD (XCT) electrospray trap. The microwave reactions were performed in the CEM Discover single-mode reactor with controlled power, temperature, and time settings. The NMR spectra of oxopiperazine compounds were recorded on a Bruker AVANCE 400, 500, or 600 MHz spectrometer.

Example 2—Materials and Methods: Synthesis and Characterization of Oxopiperazine Dimers and Trimers Oxopiperazine dimers were synthesized as shown in Scheme 1 below.

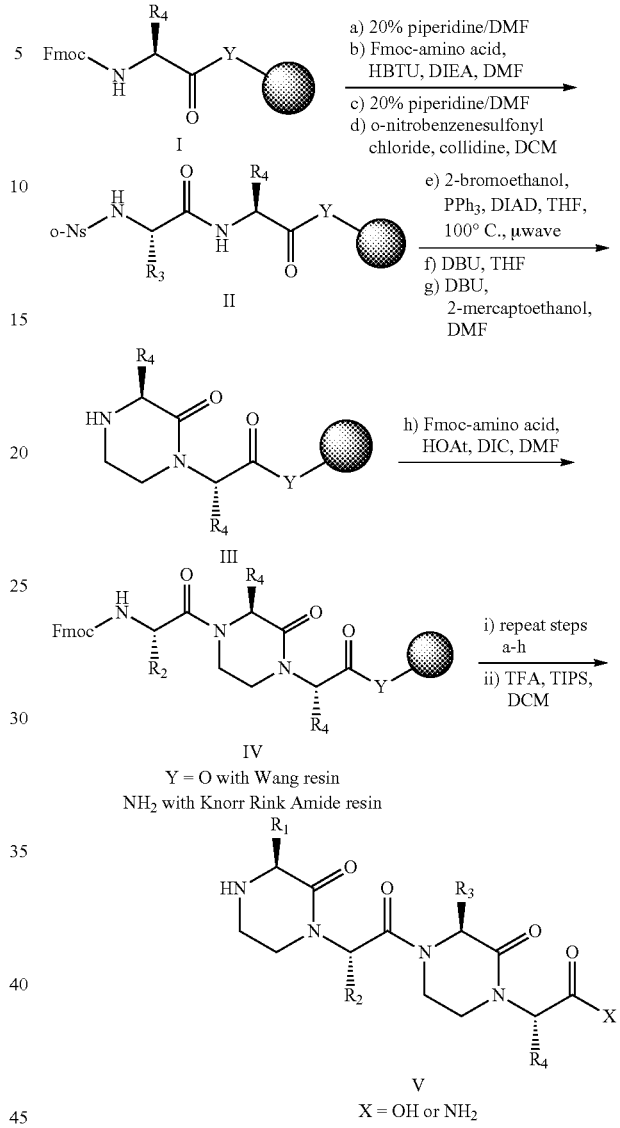

Scheme 1

An Fmoc amino acid linked to Wang or Knorr Rink Amide resin (I) was extended to a dipeptide using standard Fmoc solid phase peptide synthesis methods in a solid phase reaction vessel (Coin et al., Nat. Protoc. 2:3247 (2007), which is hereby incorporated by reference in its entirety). The resultant dipeptide was deprotected with 20% piperidine/dimethylformamide (DMF) and the resin was washed sequentially with DMF, dichloromethane (DCM), methanol (MeOH), and diethyl ether and dried under vacuum. o-Nitrobenzenesulfonyl chloride (Ns-Cl, 10 eq) and collidine (10 eq) were dissolved in dry DCM and added to the reaction vessel. The mixture was shaken for 2 hours at 23° C. to obtain compound II.

The resin was washed sequentially with DMF, DCM, MeOH, and diethyl ether and dried for 12 hours under vacuum. The resin was transferred to a glass microwave tube (CEM). Triphenylphosphine ($PPh_3$, 10 eq) was added and the tube was flushed with nitrogen gas for 30 minutes. Tetrahydrofuran (THF), diisopropyl azodicarboxylate (DIAD, 10 eq), and 2-bromoethanol (10 eq) were added and the reaction mixture was subjected to microwave irradiation (200 watts, 250 psi) for 10 minutes at 100° C. The resin was washed sequentially with THF, DMF, and DCM. The resin was transferred to a solid phase vessel and treated with 1,8-diazabicyclo[5.4.0]undec-7-ene (DBU) in THF for 2 hours. The resin was washed with THF, DMF, DCM, and diethyl ether and allowed to dry for 30 minutes followed by treatment with DBU and 2-mercaptoethanol in DMF for 2 hours to obtain compound III.

Compound III was then washed with DMF, DCM, MeOH, and diethyl either and dried. The desired pre-activated Fmoc-amino acid was added to the resin and the mixture was shaken at 23° C. for 12 hours affording compound IV.

Nosyl protection and the ring formation steps were repeated to obtain oxopiperazine dimer V after cleavage from the resin with 95% trifluoroacetic acid (TFA), 2.5% water, and 2.5% triisopropylsilane (TIPS).

Figure 3A:
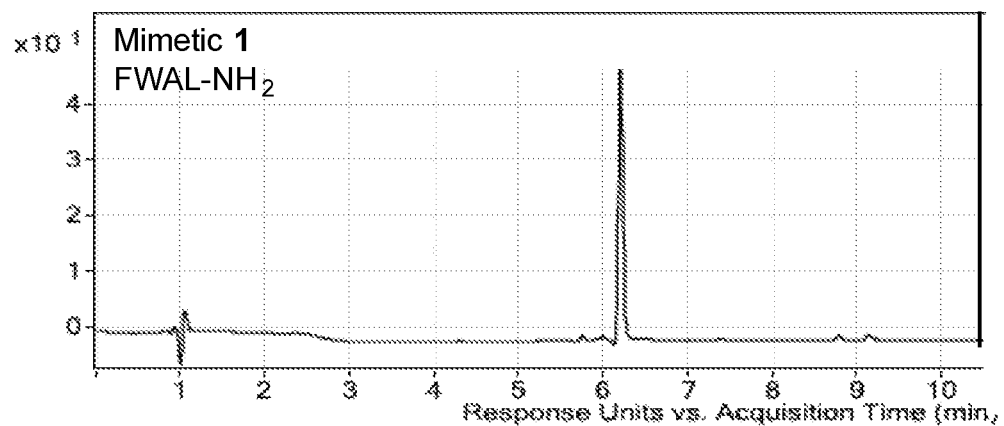
FIGS. 3A-T are analytical HPLC traces of the indicated oxopiperazines and monomer-peptides. For compounds 1-3, 5, and 13-20, HPLC was performed in 5% to 95% acetonitrile in water (0.1% formic acid) for 10 minutes. The UV trace is at 280 nm. For compounds 4, 7, and 9-12, HPLC was performed in 5% to 95% acetonitrile in water (0.1% trifluoroacetic acid) for 30 minutes. The UV trace is at 280 nm. For compound 6, HPLC was performed in 5% to 95% acetonitrile in water (0.1% trifluoroacetic acid) for 10 minutes. The UV trace is at 280 nm. For compound 8, HPLC was performed in 5% to 95% acetonitrile in water (0.1% formic acid) for 10 minutes. The UV trace is at 220 nm.
Figure 3B:
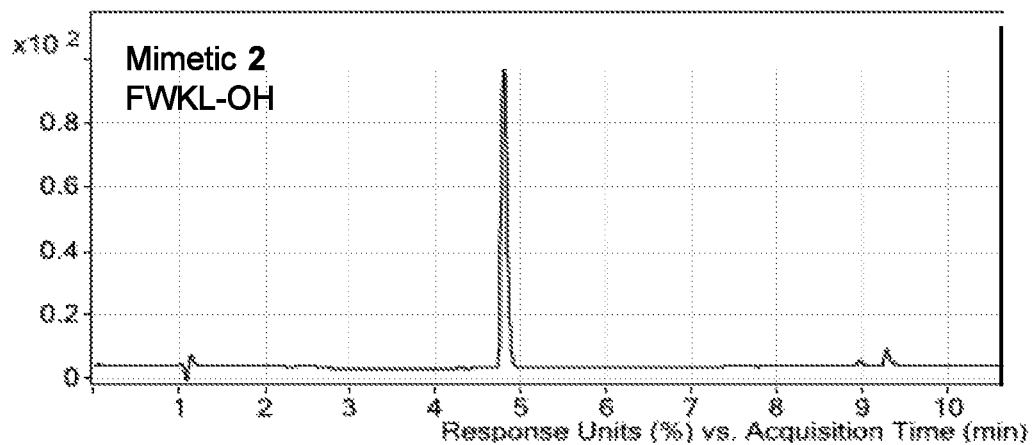
Figure 3C:
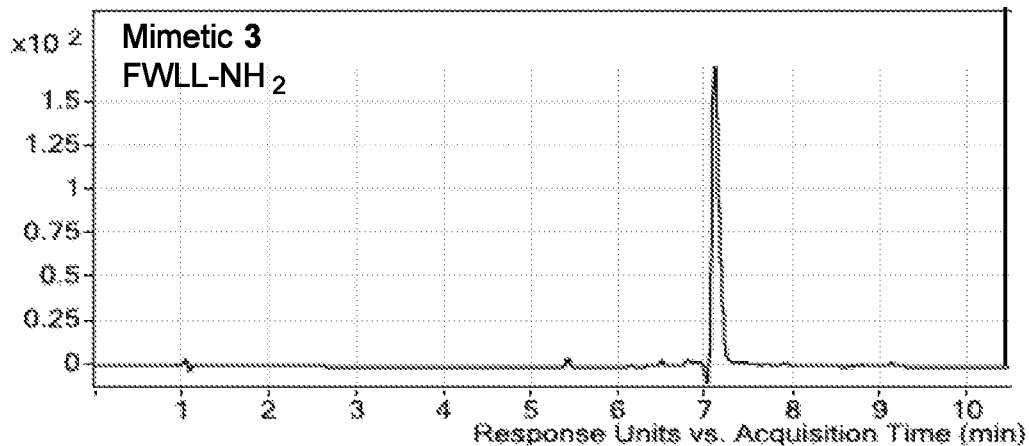
Figure 3D:
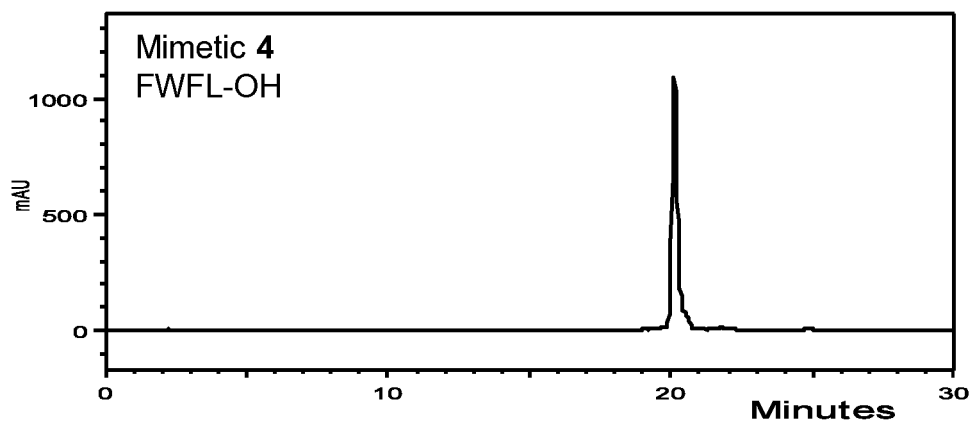
Figure 3E:
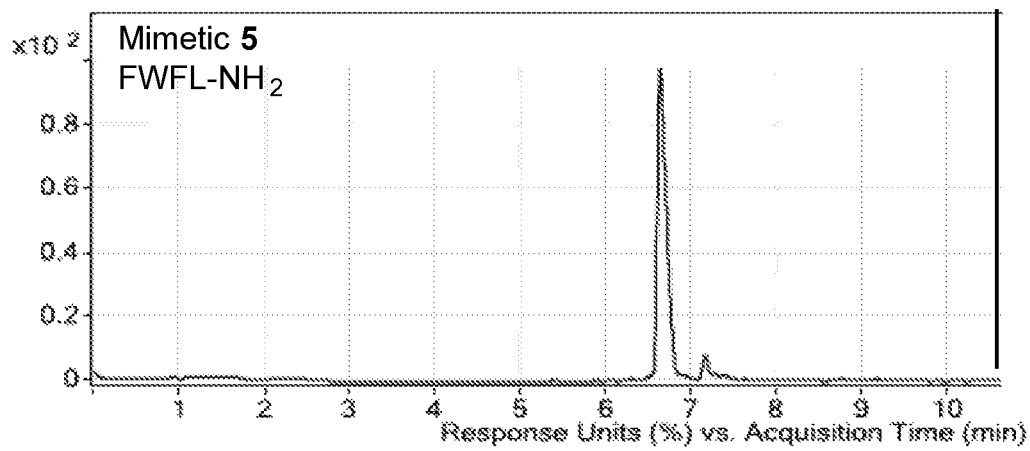
Figure 3F:
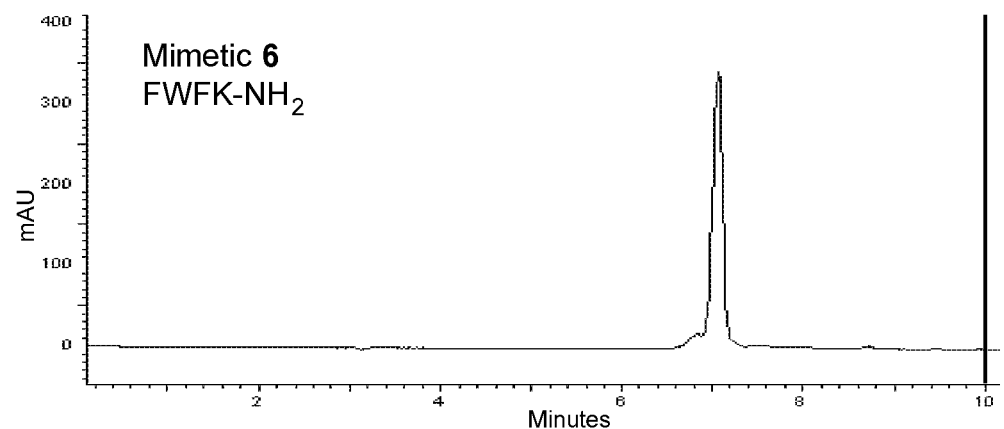
Figure 3G:
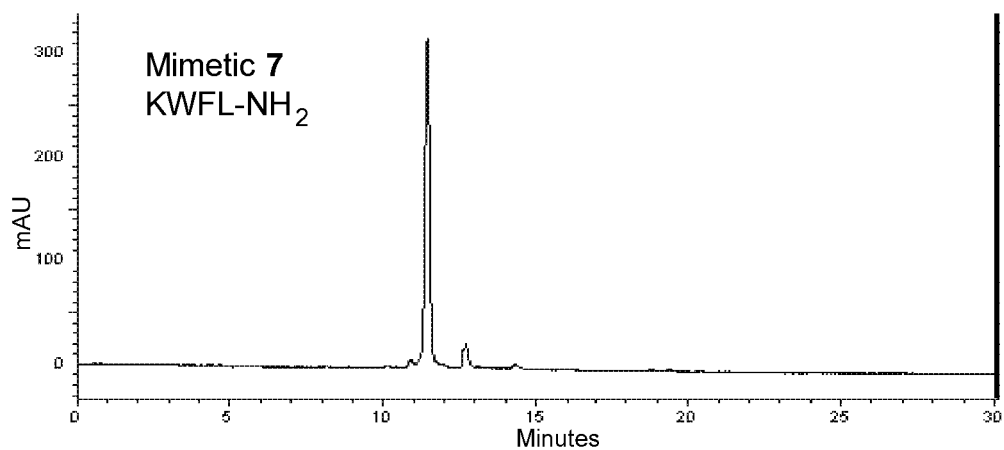
Figure 3H:
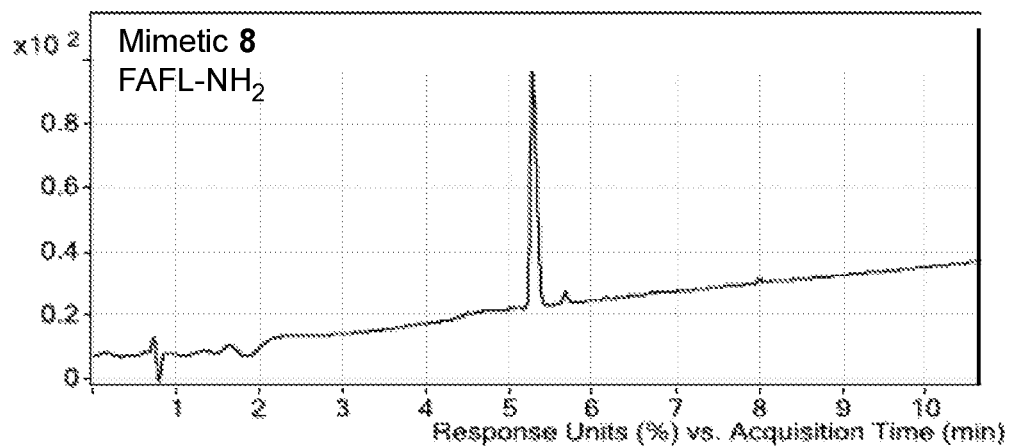
Figure 3I:
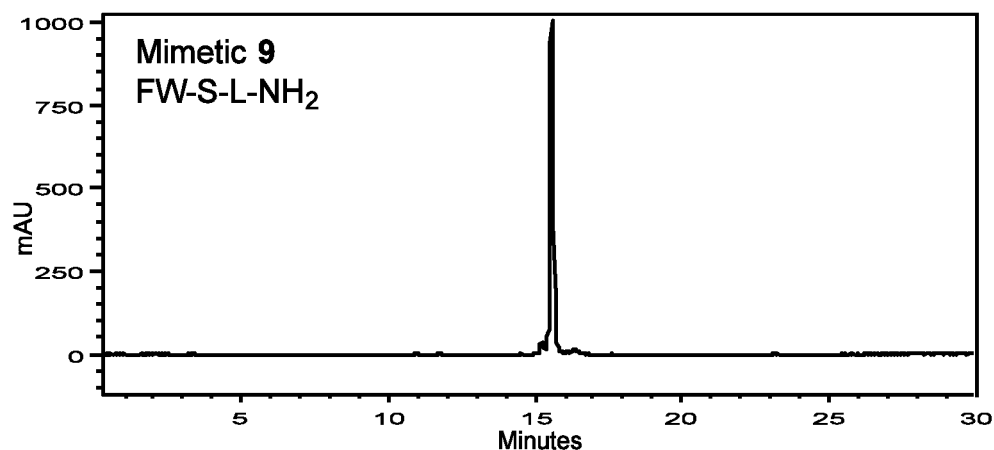
Figure 3J:
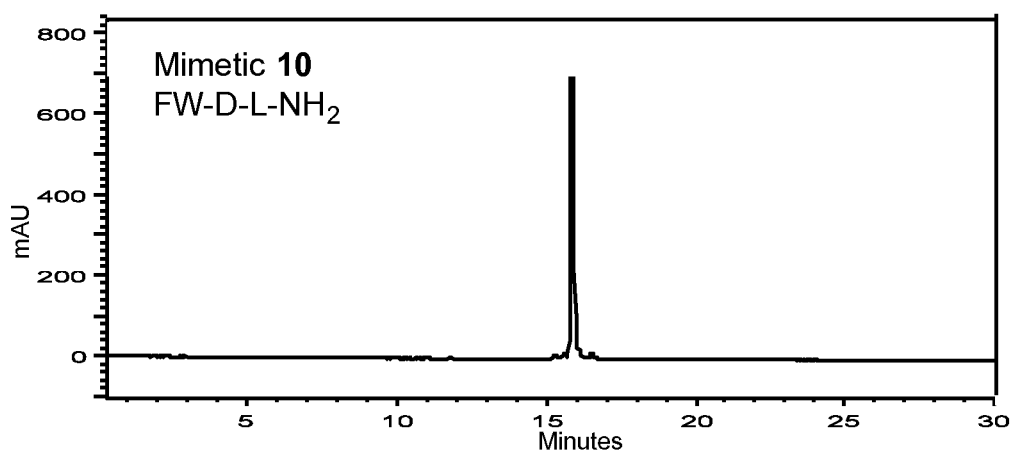
Figure 3K:
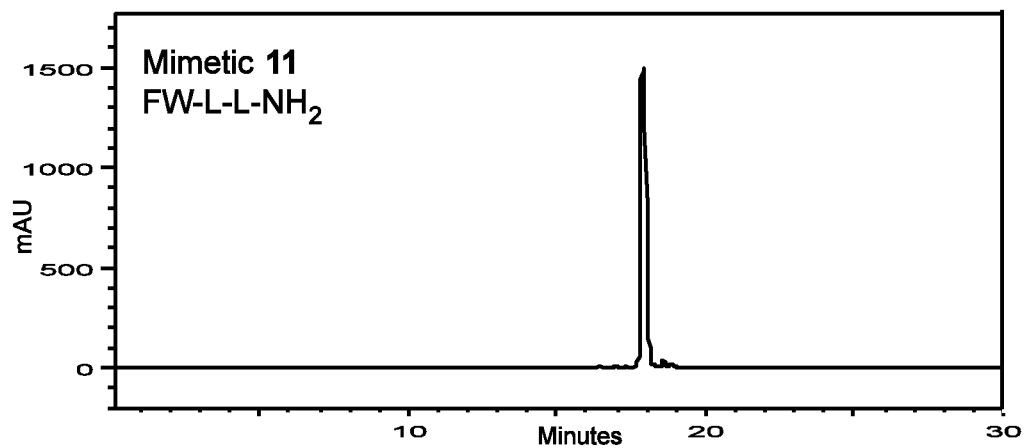
Figure 3L:
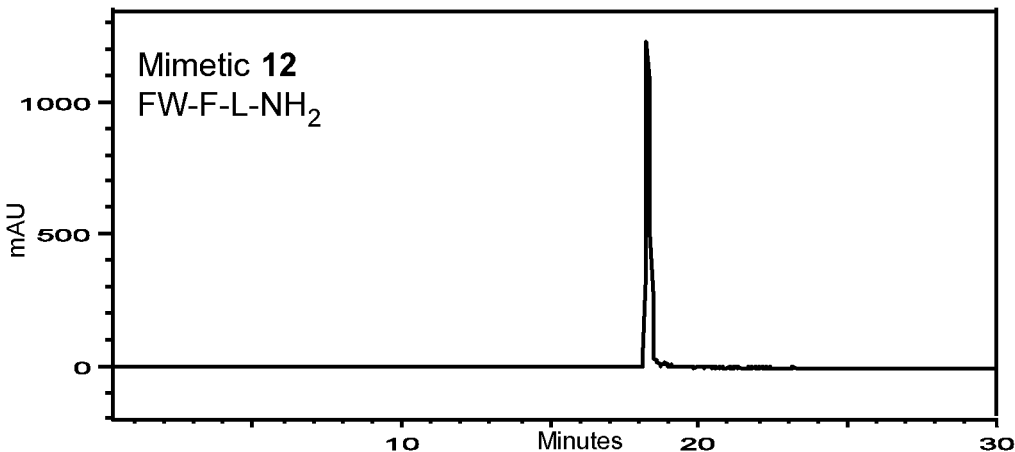
Figure 3M:
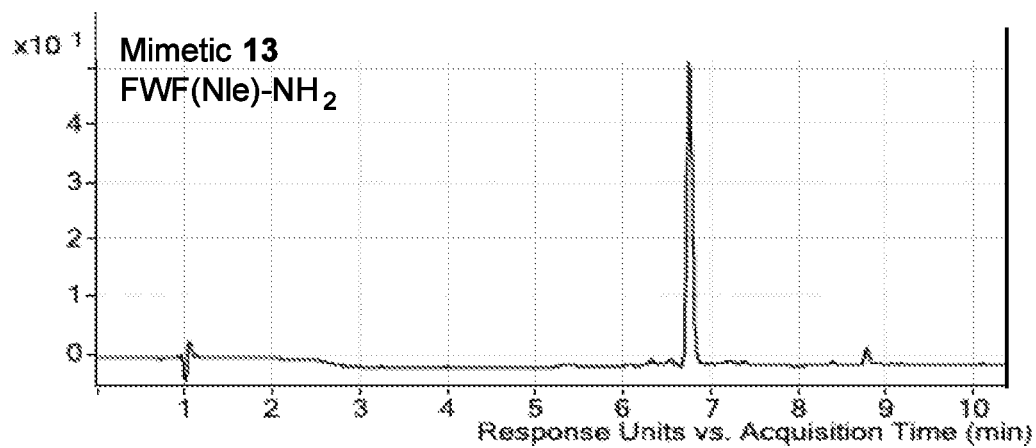
Figure 3N:
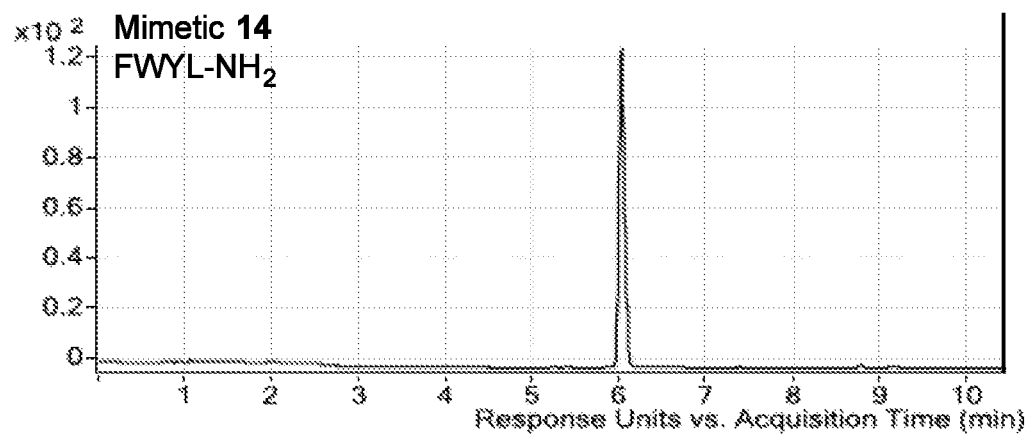
Figure 3O:
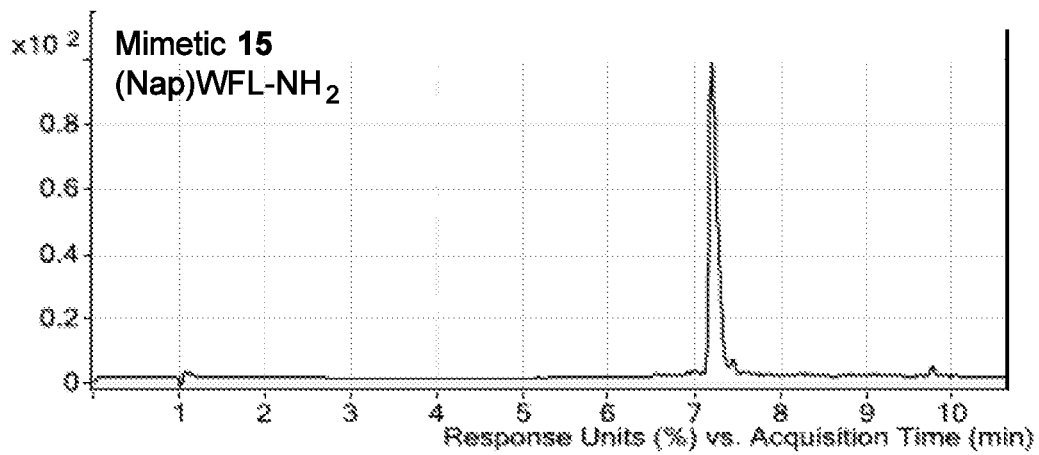
Figure 3P:
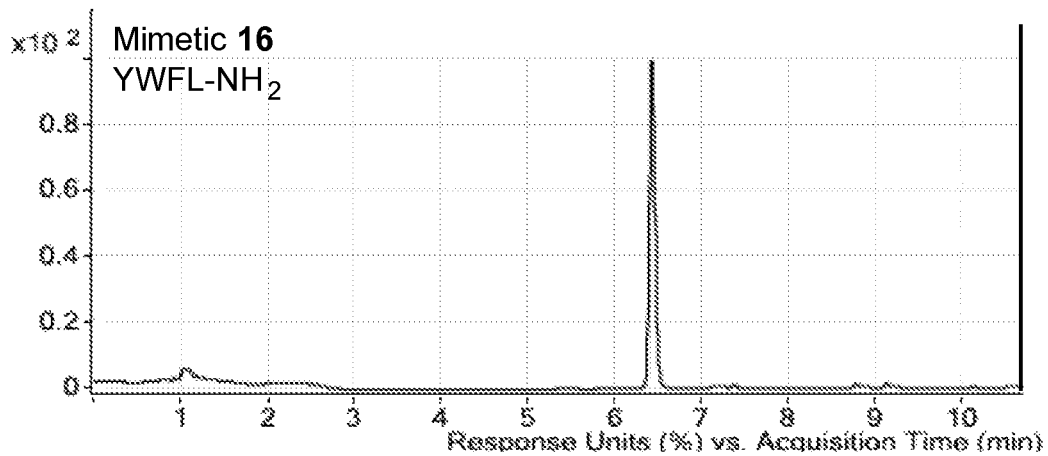
Figure 3Q:
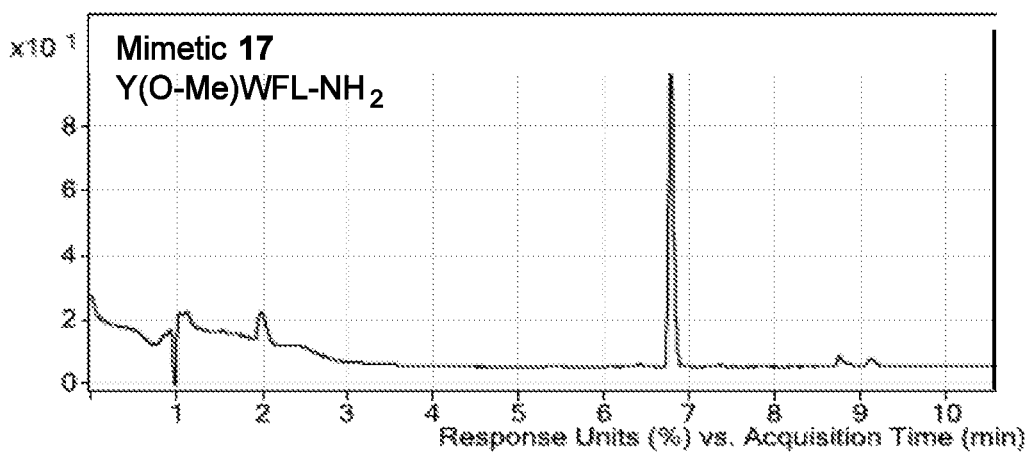
Figure 3R:
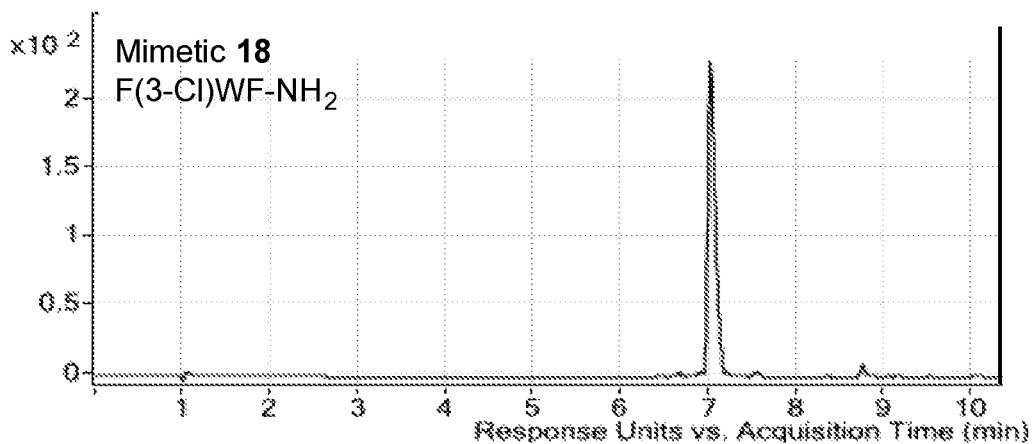
Figure 3S:
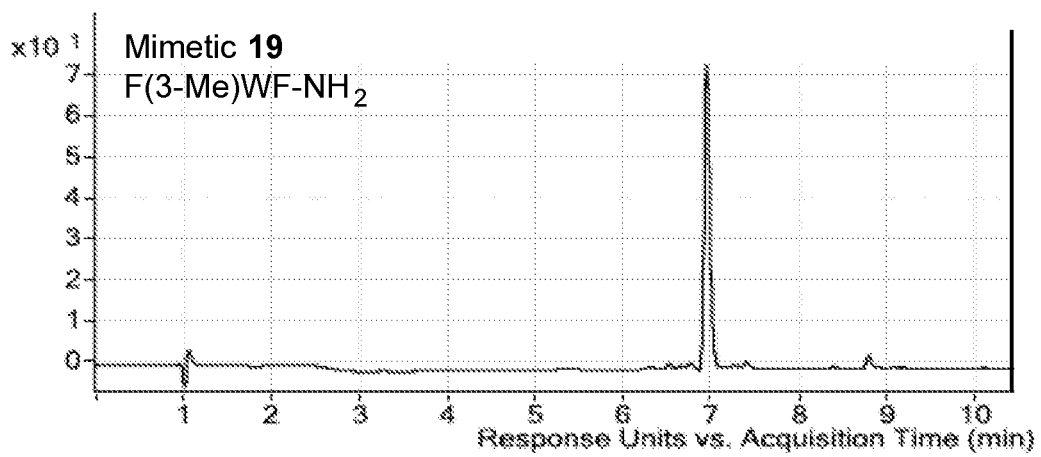
Figure 3T:
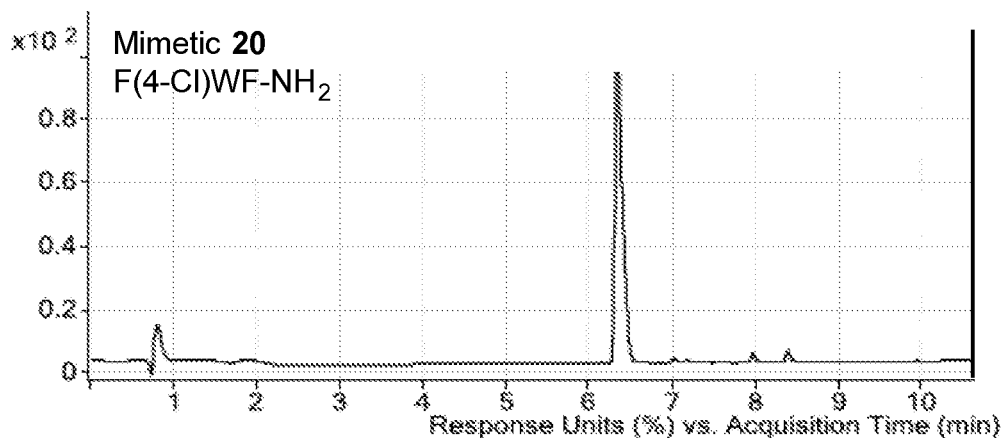

Oligooxopeparizes 1-20 were synthesized and characterized by HPLC and $^1$H-NMR. Their structure and $^1$H-NMR characterization values are shown in Table 1 below. HPLC traces are shown in FIGS. 3A-T.

TABLE 1

Compound Characterization

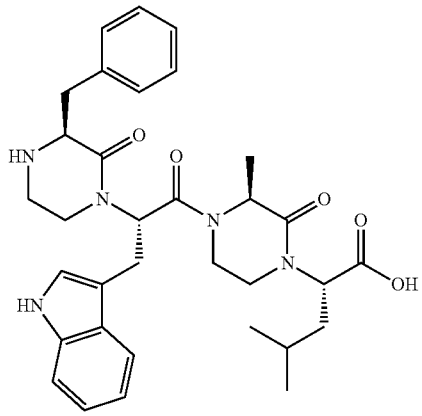 [SMILES: CC(C)C[C@@H](C(=O)O)N1CCN(C(=O)[C@H](Cc2c[nH]c3ccccc23)N2CCN[C@@H](Cc3ccccc3)C2=O)[C@@H](C)C1=O]

Oligooxopiperazine 1: FWAL-OH
$^1$H-NMR (600 MHz, d$_6$-DMSO) δ 10.93 (s, 0.3H), 10.89 (s, 0.7H), 9.35 (br, 1.0H), 8.23 (br, 1.0H), 7.64 (d, J = 7.86, 0.8H), 7.60 (d, J = 7.92, 0.2H), 7.37-7.14 (m, 5.0H), 7.13-6.97 (m, 3.0H), 5.72 (dd, J = 8.58, 6.48, 0.8H), 5.59 (app. t, J = 7.62, 0.2H), 4.97 (dd, J = 11.46, 7.02, 0.8H), 4.95-4.92 (m, 0.2H), 4.63 (q, J = 6.86, 1.0H), 4.15 (br, 1.0H), 3.80 (dt, J = 13.60, 3.60, 1.0H), 3.59 (br, 1.0H), 3.51-3.44 (m, 1.0H), 3.27-3.15 (m, 3.0H), 3.14-3.07 (m, 1.0H), 3.05-2.95 (m, 1.0H), 2.58-2.53 (m, 4.0H), 1.80-1.68 (m, 1.0H), 1.66-1.52 (m, 1.0H), 1.42-1.32 (m, 1.0H), 1.29 (d, J = 7.02, 2.0H), 1.01 (d, J = 6.55, 0.6H), 0.92 (d, J = 6.55, 0.4H), 0.89 (d, J = 6.55, 2.1H), 0.87 (d, J = 6.55, 0.9H), 0.83 (d, J = 6.55, 2.1H), 0.81 (d, J = 6.55, 0.9H). HRMS (ESI) C$_{33}$H$_{41}$N$_5$O$_5$ [M + H]$^+$ calc'd = 588.3108; found = 588.3311.
See FIG. 3A.

TABLE 1-continued

Compound Characterization

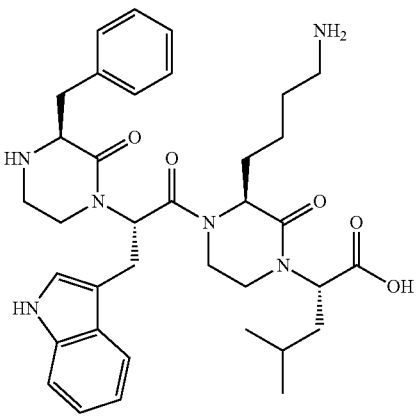 [SMILES: CC(C)C[C@@H](C(=O)O)N1CCN(C(=O)[C@H](Cc2c[nH]c3ccccc23)N2CCN[C@@H](Cc3ccccc3)C2=O)[C@@H](CCCCN)C1=O]

Oligooxopiperazine 2: FWKL-OH
$^1$H-NMR (400 MHz, MeOD) (data for the major rotamer) δ 7.70 (d, J = 8.90, 1.0H), 7.60 (d, J = 7.8, 0.5H), 7.50 (d, J = 7.4, 0.5H), 7.40-7.20 (m, 4.0H), 7.20-6.90 (m, 4.0H), 5.80-5.67 (m, 2.0H), 5.12-5.00 (m, 2.0H), 4.49-4.40 (m, 1.6H), 4.34 (app d, J = 11.90, 1.4H), 4.24-4.08 (m, 2.5H), 3.82-3.51 (m, 5.5H), 2.98-2.75 (m, 5.0H), 2.71-2.58 (m, 2.0H), 2.26 (t, J = 7.90, 1.7H), 1.80-1.56 (m, 4.3H), 1.50-1.31 (m, 2.8H), 1.29-1.17 (m, 2.3H), 1.15 (s, 0.6H), 0.88 (d, J = 6.70, 3.0H), 0.82 (d, J = 6.10, 3.0H).
HR-MS (ESI) C$_{36}$H$_{48}$N$_6$O$_5$ [M + H]$^+$ calc'd = 645.3686; found = 645.4044.
See FIG. 3B.

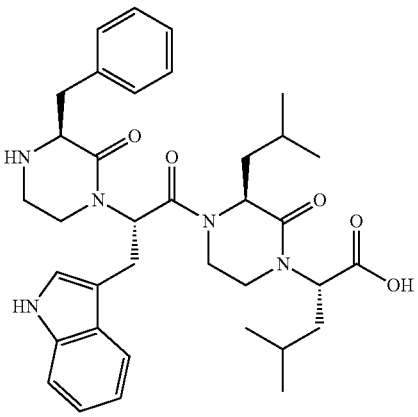 [SMILES: CC(C)C[C@@H](C(=O)O)N1CCN(C(=O)[C@H](Cc2c[nH]c3ccccc23)N2CCN[C@@H](Cc3ccccc3)C2=O)[C@@H](CC(C)C)C1=O]

Oligooxopiperazine 3: FWLL
$^1$H-NMR (600 MHz, d$_6$-DMSO) δ 10.89 (br s, 1.0H), 9.34 (br d, 1.0H), 7.62 (d, J = 7.84, 1.4H), 7.60 (d, J = 7.84, 0.6H), 7.34 (d J = 7.84, 2.0H), 7.30 (br s, 1.0H), 7.22-7.11 (m, 2.0H), 7.11-7.06 (m, 1.0H), 7.01 (q, J = 7.53, 1.5H), 6.53 (s, 0.5H), 5.73 (t, J = 7.40, 0.6H), 5.60-5.51 (m, 0.6H), 4.96 (dd, J = 11.85, 7.50, 0.4H), 4.90 (dd, J = 11.74, 7.08, 0.6H), 4.77 (t, J = 6.69, 0.6H), 4.52 (br, 0.4H), 3.84 (br, 1.0H), 3.56 (br, 1.5H), 3.23-3.17 (m, 3.5H), 3.09 (br, 1.0H), 3.02 (br, 1.0H), 2.87 (br, 1.0H), 1.78-1.69 (m, 1.5H), 1.66-1.61 (m, 0.5H), 1.60-1.50 (m, 4.0H), 1.36-1.25 (m, 1.0H), 1.23 (s, 0.5H), 1.12 (br, 0.5H), 0.92-0.86 (m, 9.0H), 0.80 (d, J = 6.48, 1.0H) 0.78 (d, J = 6.48, 1.0H), 0.64 (d, J = 6.48, 1.0H), 0.56 (br, 0.7H). HRMS (ESI) C$_{36}$H$_{47}$N$_5$O$_5$ [M + H]$^+$ calc'd = 630.3577; found = 630.4002.
See FIG. 3C.

TABLE 1-continued

Compound Characterization

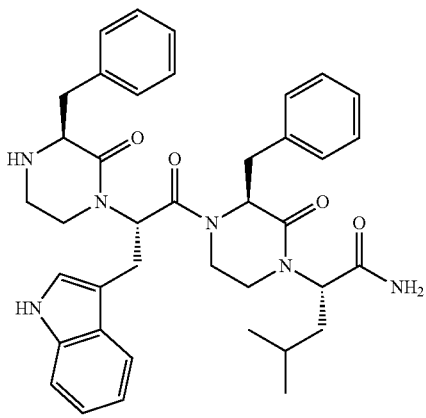 [SMILES: CC(C)C[C@@H](C(N)=O)N1CCN(C(=O)[C@H](Cc2c[nH]c3ccccc23)N2CCN[C@@H](Cc3ccccc3)C2=O)[C@@H](Cc2ccccc2)C1=O]

Oligooxopiperazine 4: FWFL-OH
$^1$H-NMR (400 MHz, MeOD) δ 7.51 (d, J = 7.88, 0.4H), 7.40 (d, J = 7.88, 0.6H), 7.34-7.20 (m, 5.0H), 7.16-6.97 (m, 8.4H), 6.79 (s, 0.6H), 5.85 (app. t, J = 7.90, 0.4H), 5.23 (t, J = 7.56, 0.6H), 5.20 (dd, J = 11.20, 6.08, 0.6H), 4.97 (t, J = 5.67, 0.4H), 4.93-4.87 (m, 1.0H), 4.42 (br, 0.6H), 4.21 (dd, J = 9.36, 4.84, 0.4H), 4.09 (dd, J = 9.88, 5.88, 0.6H), 3.78 (dt, J = 13.49, 3.63, 0.4H), 3.67-3.55 (m, 1.0H), 3.46 (app. t, J = 5.05, 1.3H), 3.44-3.39 (m, 0.5H), 3.35-3.30 (m, 0.5H), 3.29 (app. t, J = 3.72, 0.7H), 3.20-3.04 (m, 4.0H), 3.00-2.93 (m, 1.5H), 2.85 (m, J = 14.9, 9.38, 0.4H), 2.69-2.62 (m, 1.0H), 2.50 (dd, J = 14.89, 9.79, 0.6H), 2.46-2.38 (m, 0.5H), 1.80-1.64 (m, 1.5H), 1.60-1.36 (m, 2.0H), 1.28-1.07 (m, 1.5H), 0.91 (d, J = 6.96, 2.0H), 0.89 (d, J = 6.76, 2.0H), 0.84 (d, J = 6.40, 1.0H), 0.80 (d, J = 6.64, 1.0H). LRMS $C_{39}H_{45}N_5O_5$ [M + H]$^+$ calc'd = 664.3; found = 664.2.
See FIG. 3D.

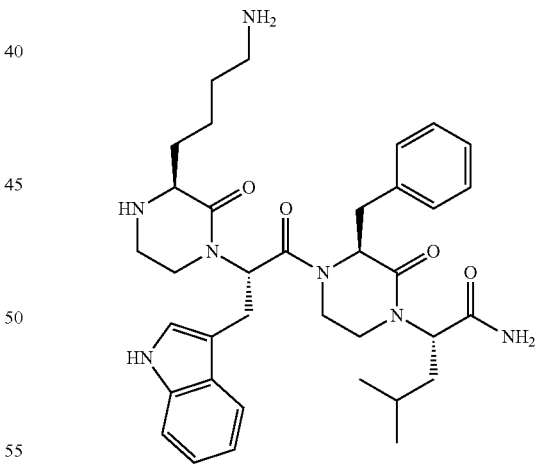

Oligooxopiperazine 5: FWFL-NH$_2$
$^1$H-NMR (400 MHz, d$_6$-DMSO) δ 10.89 (app. d, J = 1.74, 0.6H), 10.88 (s, 0.4H), 9.26 (br d, 2.0H), 7.57 (d, J = 7.76, 0.7H), 7.45 (d, J = 4.95, 0.7H), 7.42 (d, J = 4.06, 1.0H) 7.38-7.25 (m, 4.0H), 7.24-7.18 (m, 3.2H), 7.13-7.07 (m, 2.0H), 7.05-6.94 (m, 2.0H), 6.94-6.88 (m, 1.0H), 5.68 (dd, J = 8.72, 6.36, 0.6H), 5.32 (t, J = 7.44, 0.4H), 4.99 (dd, J = 10.17, 5.85, 4.32, 1.0H), 4.93 (t, J = 6.30, 0.6H), 4.78-4.72 (m, 0.4H), 4.20 (br, 0.5H), 4.17 (br, 0.5H), 3.75 (br, 0.5H), 3.71 (br, 0.5H), 3.26-3.04 (m, 7.0), 3.00-2.88 (m, 3.0H), 2.85 (br, 0.3H), 2.84 (br, 0.2H), 2.81-2.73 (m, 1.8H), 1.67-1.58 (m, 1.0H), 1.56-1.47 (m, 2.0H), 1.32 (br, 1.0H), 1.24 (br, 0.5H), 1.16 (br, 1.5H), 0.95-0.86 (m, 4.0H), 0.84 (d, J = 6.55, 2.0H). HRMS (ESI) $C_{39}H_{46}N_6O_4$ TABLE 1-continued Compound Characterization

[M + H]$^+$ calc'd = 663.3581; found = 663.3917.
See FIG. 3E.

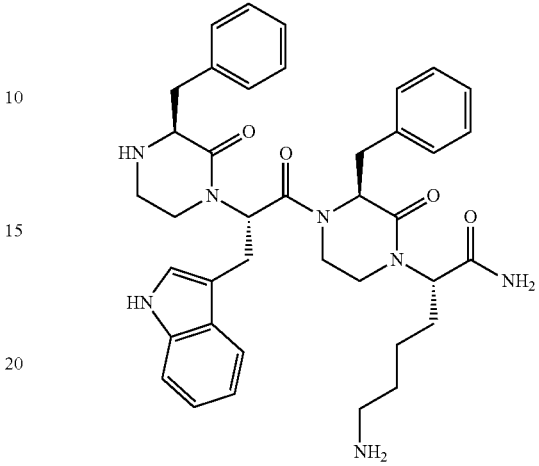

Oligooxopiperazine 6: FWFK-NH$_2$
$^1$H-NMR (600 MHz, d$_6$-DMSO) δ 10.88 (br, 1.0H), 8.46 (br, 0.7H), 9.30 (br d, 2.0H), 7.65 (br, 2.0H), 7.55 (d, J = 8.10, 0.3H), 7.52 (br, 0.3H), 7.49 (br, 0.3H), 7.40 (br, 1.0H), 7.39-7.25 (m, 4.0H), 7.24-7.06 (m, 6.0H), 7.04-6.98 (m, 1.0H), 6.92 (br, 0.7H), 6.76 (br, 0.3H), 6.53 (br, 2.0H), 5.88 (br, 0.4H), 5.69 (dd, J = 9.00, 6.42, 0.6H), 5.30 (br, 0.5H), 4.99 (br, 1.0H), 4.94-4.85 (m, 1.0H), 4.76 (br, 0.5H), 4.25 (br, 0.5H), 3.21-3.05 (m, 4.0H), 3.04-2.88 (m, 3.0H), 2.82-2.72 (m, 3.0H), 2.09 (s, 0.2H), 1.88-1.74 (m, 1.0H), 1.69-1.60 (m, 1.0H), 1.59-1.43 (m, 3.0H), 1.28-1.0 (m, 3.0H). HRMS (ESI) $C_{39}H_{47}N_7O_4$ [M + H]$^+$ cal'd = 678.3846; found = 678.3861.
See FIG. 3F.

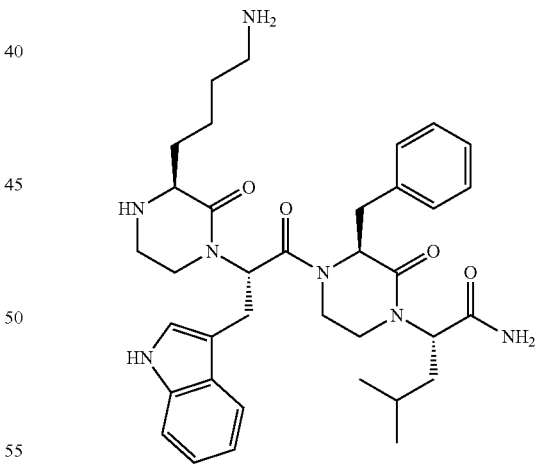

Oligooxopiperazine 7: KWFL-NH$_2$
$^1$H-NMR (400 MHz, CDCl$_3$) δ 9.78 (br, 1.0H), 7.99 (br, 2.0H), 7.75 (br, 1.0H), 7.42 (t, J = 6.63, 2.0H), 7.38-7.27 (m, 3.0H), 7.20 (d, J = 7.40, 1.5H), 7.08 (t, J = 7.17, 1.0H), 7.04-6.97 (m, 1.5H), 6.76 (s, 1.0H), 5.18-5.08 (m, 1.0H), 4.94-4.82 (m, 2.0H), 4.82-4.74 (m, 1.0H), 3.55-3.44 (m, 1.5H), 3.43-3.14 (m, 5.0H), 2.97 (t, J = 12.06, 1.0H), 2.87 (br, 1.0H), 2.69 (br, 1.5H), 2.19-2.14 (m, 1.0H), 1.74-1.62 (m, 3.0H), 1.50 (m, 2.0H), 1.34-1.22 (m, 4.0H), 0.99 (d, J = 5.55, 6.0H), 0.92-0.77 (m, 4.0H), 0.72 (br, 1.5H), 0.56 (br, 0.5H). HRMS (ESI)

TABLE 1-continued

Compound Characterization $C_{36}H_{49}N_7O_4$ [M + H]$^+$ calc'd = 644.3746; found = 644.4091.
See FIG. 3G.

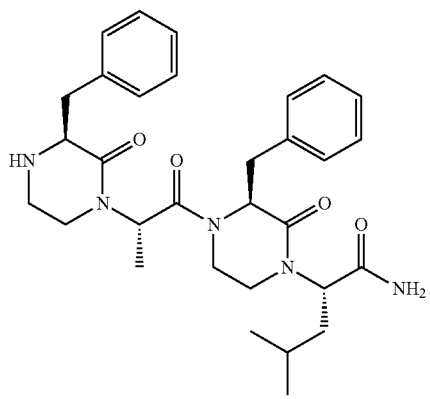 [SMILES: CC(C)C[C@@H](C(N)=O)N1CCN(C(=O)[C@H](C)N2CCN[C@@H](Cc3ccccc3)C2=O)[C@@H](Cc2ccccc2)C1=O]

Oligooxopiperazine 8: FAFL-NH$_2$
$^1$H-NMR (600 MHz, d$_6$-DMSO) δ 9.40 (br, 2.0H), 7.46 (s, 0.5H), 7.40-7.27 (m, 5.0H), 7.26-7.19 (m, 2.5H), 7.14-7.11 (m, 1.0H), 7.10-7.04 (m, 1.0H), 6.56 (br, 1.0H), 5.36 (dd, J = 13.89, 6.99, 0.6H), 5.06 (q, J = 5.32, 0.6H), 5.02 (q, J = 5.55, 0.4H), 4.92 (t, J = 5.40, 0.6H), 4.79-4.74 (m, 0.4H), 4.73 (t, J = 6.74, 0.4H), 4.37 (br, 0.5H), 4.25 (br, 0.3H), 4.10 (br, 0.5H), 3.72 (dt, J = 13.75, 3.63, 0.7H), 3.52 (br, 1.0H), 3.47-3.42 (m, 1.0H), 3.41-3.36 (m, 1.5H), 3.30-3.23 (m, 1.5H), 3.20-3.13 (m, 2.4H), 3.06-2.97 (m, 2.6H), 2.87-2.82 (m, 1.0H), 1.72-1.65 (m, 1.0H), 1.60-1.49 (m, 2.3H), 1.42 (br, 0.7H), 1.23 (d, J = 6.9, 2.0H), 1.18 (br, 1.0H), 0.94-0.89 (m, 3.0H), 0.86 (d, J = 6.55, 2.0H), 0.66 (d, J = 6.55, 1.0H). HRMS (APCI) $C_{31}H_{41}N_5O_4$ [M + H]$^+$ calc'd = 548.3159; found = 548.3493.
See FIG. 3H.

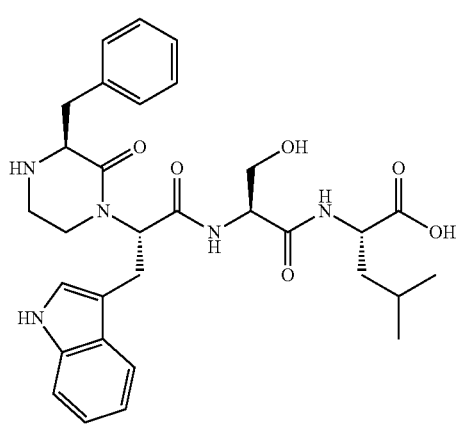 [SMILES: CC(C)C[C@H](NC(=O)[C@H](CO)NC(=O)[C@H](Cc1c[nH]c2ccccc12)N1CCN[C@@H](Cc2ccccc2)C1=O)C(=O)O]

Monomer peptide 9: FWSL-OH
$^1$H-NMR (400 MHz, d$_6$-MeOD) δ 8.08 (q, J = 7.74, 0.6H), 7.58 (d, J = 7.84, 1.0H), 7.30 (d, J = 8.08, 1.0H), 7.26-7.17 (m, 3.0H), 7.12-7.03 (m, 3.4H), 7.01-6.96 (m, 1.0H), 5.36 (dd, J = 10.5, 5.98, 1.0H), 4.48-4.36 (m, 2.0H), 4.12 (dd, J = 9.75, 5.28, 1.0H), 3.81 (d, J = 4.92, 0.3H), 3.79 (d, J = 4.92, 0.7H), 3.77 (d, J = 6.30, 0.3H), 3.74 (d, J = 6.30, 0.7H), 3.52 (dd, J = 7.20, 3.80, 2.0H) 3.44-3.28 (m, 3.0H), 3.14 (dt, 13.04, 3.68, 1.0H), 3.05-2.96 (m, 1.0H), 2.68 (dd, J = 11.96, 9.64, 1.0H), 1.73-1.63 (m, 1.0H), 1.62-1.57 (m, 2.0H), 0.90 (d, J = 6.50, 3.0H), 0.87 (d, J = 6.50, 3.0H). LRMS $C_{31}H_{39}N_5O_6$ [M + H]$^+$ calc'd = 578.3; found = 578.2.
See FIG. 3I.

TABLE 1-continued

Compound Characterization

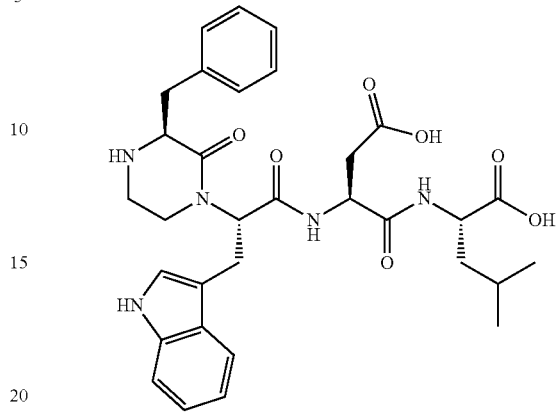

Monomer peptide 10: FWDL-OH
$^1$H-NMR (400 MHz, d$_6$-MeOD) δ 8.07 (d, J = 8.04, 0.3H), 7.64 (d, J = 7.84, 0.7H), 7.38 (d, J = 8.04, 1.0H), 7.34-7.25 (m, 3.0H), 7.22-7.11 (m, 4.0H), 7.06 (t, J = 7.40, 1.0H), 5.30 (dd, J = 9.26, 6.62, 1.0H), 4.49-4.41 (m, 1.0H), 4.14 (dd, J = 9.56, 5.36, 1.0H), 3.65-3.54 (m, 1.0H), 3.53-3.36 (m, 4.0H), 3.21 (dt, J = 6.24, 3.36, 1.0H), 3.05-2.96 (m, 1.0H), 2.95 (d, J = 4.69, 0.4H), 2.91 (d, J = 4.6, 0.6H), 2.84-2.74 (m, 2.0H), 1.82-1.73 (m, 1.0H), 1.72-1.63 (m, 2.0H), 0.98 (d, J = 6.44, 3.0H), 0.94 (d, J = 6.44, 3.0H). LRMS $C_{32}H_{39}N_5O_7$ [M + H]$^+$ calc'd = 606.3; found = 606.2.
See FIG. 3J.

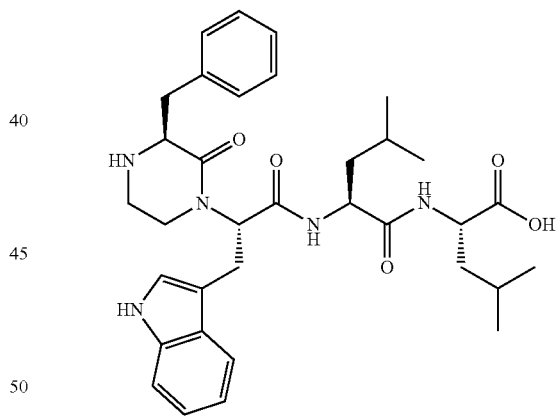

Monomer peptide 11: FWLL-OH
$^1$H-NMR (400 MHz, d$_6$-MeOD) δ 8.30 (d, J = 7.56, 0.6H), 8.22 (d, J = 7.88, 0.5H), 7.68 (d, J = 7.88, 0.9H), 7.39 (d, J = 8.08, 1.0H), 7.33-7.26 (m, 2.7H), 7.19-7.14 (m, 3.3H), 7.07 (t, J = 7.30, 1.0H), 5.50 (dd, J = 10.11, 5.37, 1.0H), 4.52-4.43 (m, 2.0H), 4.21 (dd, J = 9.54, 5.20, 1.0H), 3.76 (br, 1.0H), 3.63-3.55 (m, 1.0H), 3.49-3.36 (m, 3.0H), 3.22 (dt, J = 12.96, 3.80, 1.0H), 3.19-3.11 (m, 1.0H), 2.78 (dd, J = 14.92, 9.56, 1.0H), 1.82-1.71 (m, 1.0H), 1.70-1.59 (m, 5.0H), 1.02-0.91 (m, 12.0H). LRMS $C_{34}H_{45}N_5O_5$ [M + H]$^+$ calc'd = 604.3; found = 604.2.
See FIG. 3K.

TABLE 1-continued

Compound Characterization

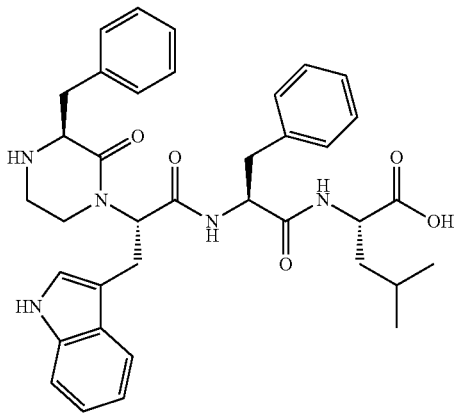 [SMILES: CC(C)C[C@H](NC(=O)[C@H](Cc1ccccc1)NC(=O)[C@H](Cc1c[nH]c2ccccc12)N1CCN[C@@H](Cc2ccccc2)C1=O)C(=O)O]

Monomer peptide 12: FW-F-L-OH
$^1$H-NMR (400 MHz, d$_6$-MeOD) δ 8.30 (d, J = 8.0, 0.4H), 8.13 (d, J = 7.92, 0.6H), 7.64 (d, J = 7.88, 1.0H), 7.40 (d, J = 8.12, 1.0H), 7.35-7.13 (m, 11.0H), 7.08 (t, J = 7.42, 1.0H), 5.41 (dd, J = 10.08, 6.00, 1.0H), 4.80-4.74 (m, 1.0H), 4.52-4.45 (m, 1.0H), 4.08 (dd, J = 9.48, 5.24, 1.0H), 3.56-3.44 (m, 2.0H), 3.43-3.40 (m, 1.0H), 3.39-3.36 (m, 1.0H), 3.29 (d, J = 4.84, 1.0H), 3.26 (d, J = 4.36, 1.0H), 3.18 (dt, 13.04, 3.56, 1.0H), 2.97-2.87 (m, 2.0H), 2.76 (dd, J = 14.86, 9.54, 1.0H), 1.81-1.72 (m, 1.0H), 1.72-1.65 (m, 2.0H), 0.99 (d, J = 6.35, 3.0H), 0.96 (d, J = 6.35, 3.0H). LRMS C$_{37}$H$_{43}$N$_5$O$_5$ [M + H]$^+$ calc'd = 638.3; found = 638.2.
See FIG. 3L.

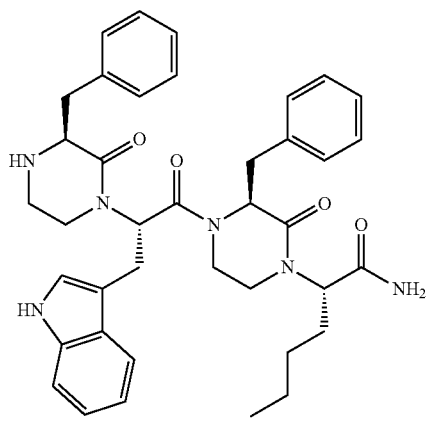 [SMILES: CCCC[C@@H](C(N)=O)N1CCN(C(=O)[C@H](Cc2c[nH]c3ccccc23)N2CCN[C@@H](Cc3ccccc3)C2=O)[C@@H](Cc2ccccc2)C1=O]

Oligooxopiperazine 13: FWF(Nle)-NH$_2$
$^1$H-NMR (600 MHz, d$_6$-DMSO) δ 10.82 (s, 0.6H), 10.76 (s, 0.4H), 7.56 (d, J = 7.58, 0.5H), 7.41 (d, J = 8.80, 1.0H), 7.32 (t, J = 8.20, 1.0H), 7.29-7.01 (m, 10.0H), 7.08-6.97 (m, 3.0H), 6.53 (br, 1.0H), 5.69 (dd, J = 8.55, 6.37, 0.6H), 5.19 (br, 0.4H), 4.98 (br, 0.6H), 4.88 (dd, J = 10.62, 5.46, 0.6H), 4.86 (dd, J = 10.62, 5.46, 0.4H), 4.72 (dd, J = 8.10, 4.14, 0.4H), 4.26 (br, 0.4H), 3.97 (t, J = 6.69, 0.2H), 3.82 (br, 0.6H), 3.29-3.25 (m, 1.0H), 3.22 (d, J = 3.96, 0.3H), 3.20-3.16 (m, 2.0H), 3.14 (t, J = 3.06, 0.4H), 3.10 (br, 0.3H), 3.09-3.05 (m, 1.7H), 3.02 (br, 0.5H), 2.98 (dt, J = 12.90, 3.57, 1.7H), 2.87 (br, 2.0H) 1.80-1.70 (m, 1.4H), 1.63-1.57 (m, 0.6H), 1.56-1.47 (m, 1.0H), 1.32-1.25 (m, 3.0H), 1.23 (s, 2.0H), 1.16-1.10 (m, 1.0H) 1.08-1.02 (m, 0.8H), 1.0-0.93 (m, 0.6H), 0.88 (app q, J = 7.38, 3.0H). HRMS (ESI) C$_{39}$H$_{46}$N$_6$O$_4$ [M + H]$^+$ calc'd = 663.3581; found = 663.3908.
See FIG. 3M.

TABLE 1-continued

Compound Characterization

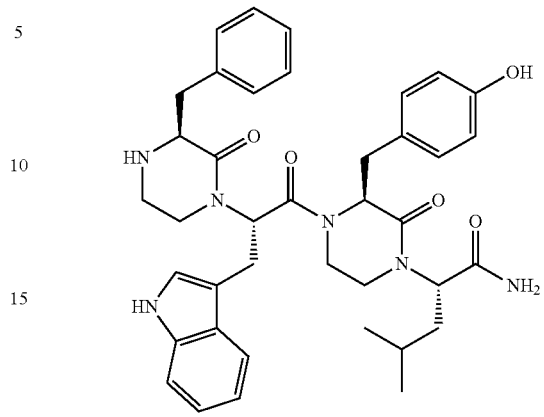

Oligooxopiperazine 14: FWYL-NH$_2$
$^1$H-NMR (600 MHz, d$_6$-DMSO) δ 10.92 (d, J = 1.62, 0.4H), 10.90 (d, J = 1.85, 0.6H), 9.27 (br, 3.0H), 7.58 (d, J = 7.94, 0.6H), 7.47 (d, J = 7.48, 0.4H), 7.44 (s, 0.4H), 7.41 (s, 0.6H), 7.33-7.23 (m, 4.0H), 7.23-7.16 (m, 2.0), 7.10-6.99 (m, 3.0H), 6.88 (d, J = 8.42, 1.0H), 6.63-6.60 (m, 2.0H), 6.56 (d, J = 8.46, 1.0H), 5.67 (dd, J = 8.96, 6.03, 0.6H), 5.41 (app. t, J = 7.77, 0.4H), 5.02-4.97 (m, 1.0H), 4.85 (t, J = 5.47, 0.6H), 4.70 (t, J = 6.03, 0.4H), 4.30 (br, 0.6H), 4.15 (dt, J = 13.27, 3.79, 0.4H), 4.09 (br, 0.4H), 3.70 (dt, J = 13.27, 3.70, 0.6H), 3.63-3.57 (m, 1.0H), 3.33 (br, 1.0H), 3.25-3.07 (m, 6.0H), 3.04-2.85 (m, 3.0H), 2.76-2.67 (m, 1.5H), 2.58 (dd, J = 13.85, 5.12, 0.5H), 1.62-1.55 (m, 0.4H), 1.55-1.45 (m, 1.6H), 1.33-1.25 (m, 0.5H), 1.24-1.10 (m, 0.5H), 0.88 (d, J = 6.55, 2.0H), 0.87 (d, J = 6.55, 2.0H), 0.84 (d, J = 6.55, 2.0H). HRMS (ESI) C$_{39}$H$_{46}$N$_6$O$_5$ [M + H]$^+$ calc'd = 679.3530; found = 679.3810.
See FIG. 3N.

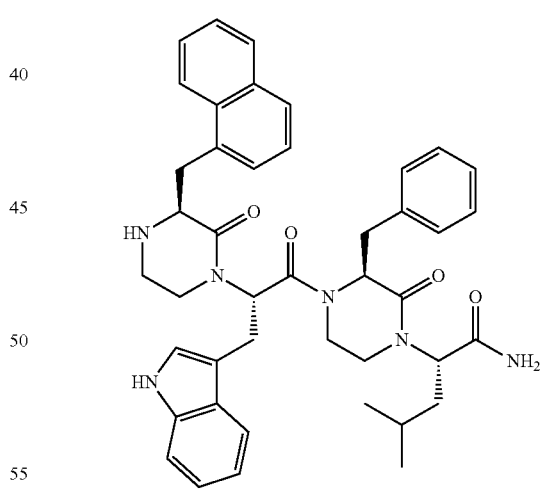

Oligooxopiperazine 15: (Nap)WFL-NH$_2$
$^1$H-NMR (600 MHz, d$_6$-DMSO) δ 10.92 (br. s, 1.0H), 9.20 (br, 2.0H), 8.03-7.97 (m, 1.3H), 7.90 (br, 0.7H), 7.66-7.53 (m, 2.0H), 7.49-7.38 (m, 2.0H), 7.35 (t, J = 7.8, 1.0H), 7.26 (s, 1.0H), 7.15-7.0 (m, 5.0H), 6.99-6.90 (m, 1.5H), 6.52 (s, 0.5H), 5.72 (br, 0.7H), 5.39 (br, 0.3H), 5.01 (dd, J = 11.40, 6.00, 1.0H), 4.96 (br, 0.7H), 4.78 (br, 0.3H), 4.33 (br, 0.5H), 4.17 (br, 0.5H), 3.82 (br, 0.3H), 3.76 (br, 1.0H), 3.64 (br, 0.7H), 3.24-3.04 (m, 7.0H), 3.04-2.96 (m, 2.5H), 2.95-2.87 (m, 1.5H), 2.86-2.74 (m, 2.0H), 1.66-1.59 (m, 0.7H), 1.57-1.47 (m, TABLE 1-continued Compound Characterization 2.0H), 1.35 (br, 0.3H), 1.24 (br, 0.5H), 1.18 (br, 0.5H), 0.89 (d, J = 6.55, 3.5H), 0.85 (d, J = 6.55, 2.5H). HRMS (ESI) C$_{43}$H$_{48}$N$_6$O$_4$ [M + H]$^+$ calc'd = 713.3737; found = 713.4041.
See FIG. 3O.

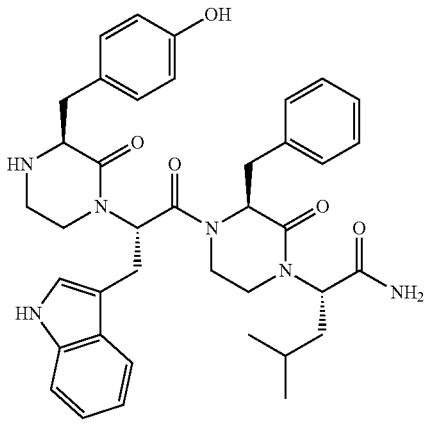 [SMILES: CC(C)C[C@@H](C(N)=O)N1CCN(C(=O)[C@H](Cc2c[nH]c3ccccc23)N2CCN[C@@H](Cc3ccc(O)cc3)C2=O)[C@@H](Cc2ccccc2)C1=O]

Oligooxopiperazine 16: YWFL-NH$_2$
$^1$H-NMR (600 MHz, d$_6$-DMSO) δ 10.88 (br, 0.6H), 10.86 (br, 0.4H), 9.37 (br, 1.0H), 9.17 (br, 1.0H), 8.97 (br, 1.0H), 7.57 (d, J = 8.00, 0.6H), 7.46-7.39 (m, 1.4H), 7.33 (t, J = 7.74, 1.0H), 7.24-7.20 (m, 2.0H), 7.18 (br, 0.5H), 7.12-7.06 (m, 3.5H), 7.05-6.97 (m, 4.0H), 6.89 (br, 1.0H), 6.71 (d, J = 7.92, 1.8H), 6.53 (br, 0.2H), 5.67 (dd, J = 8.10, 6.30, 0.6H), 5.31 (br, 0.4H), 4.99 (dd, J = 10.38, 5.34, 1.0H), 4.93, (t, J = 5.82, 0.6H), 4.74 (br, 0.4H), 4.18 (br, 1.0H), 3.99 (br, 0.4H), 3.73 (br, 0.6H), 3.55 (br, 1.0H), 3.25-3.14 (m, 3.5H), 3.13-3.03 (m, 4.0H), 3.00-2.73 (m, 3.0H), 2.79-2.74 (m, 0.5H), 1.65-1.60 (m, 0.5H), 1.56-1.47 (m, 1.5H), 1.33-1.26 (m, 0.5H), 1.22-1.10 (m, 0.5H), 0.89 (d, J = 6.55, 2.0H), 0.87 (app. t, J = 3.10, 2.0H), 0.84 (d, J = 6.55, 2.0H). HRMS (ESI) C$_{39}$H$_{45}$N$_5$O$_6$ [M + H]$^+$ calc'd = 679.3530; found = 679.3755.
See FIG. 3P.

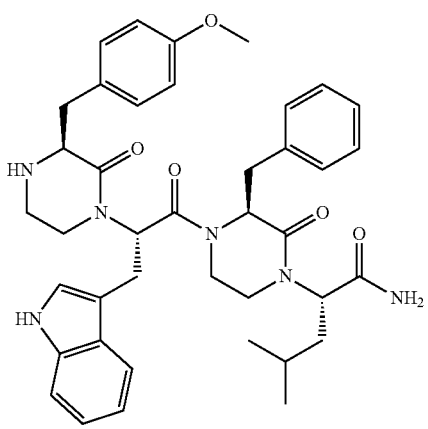 [SMILES: COc1ccc(C[C@@H]2NCCN([C@@H](Cc3c[nH]c4ccccc34)C(=O)N3CCN([C@@H](CC(C)C)C(N)=O)C(=O)[C@@H]3Cc3ccccc3)C2=O)cc1]

Oligooxopiperazine 17: Y(O—Me)WFL-NH$_2$
$^1$H-NMR (600 MHz, d$_6$-DMSO) δ 10.89 (br, 0.6H), 10.87 (br, 0.4H), 9.20 (br, 2.0H), 7.57 (d, J = 8.00, 0.3H), 7.8-7.39 (m, 1.0H), 7.34 (t, J = 8.13, 0.7H), 7.23-7.17 (m, 2.0H), 7.12-7.06 (m, 4.0H), 7.04-6.98 (m, 1.5H), 6.91 (br, 1.0H), 6.90 (d, J = 1.5H), 6.54 (br, 1.0H), 5.70 (dd, J = 8.79, 6.03, 0.6H), 5.31 (t, J = 6.40, 0.4H), 4.99 (dd, J = 10.74, 5.52, 1.0H), 4.94 (t, J = 5.73, 0.6H), 4.74 (dd, J = 7.47, 5.16, 0.4H), 4.24-4.16 (m, 0.4H), 3.73 (app. d, J = 2.40, 3.0H), 3.54 (br, 0.6H), 3.28-3.03 (m, 9.0H), 3.02-2.84 (m, 3.0H), 2.83-2.75 (m, 1.0H), 2.68 (br, 1.0H), 1.66-1.60 (m, 0.5H), 1.56-1.45 (m, 2.0H), 1.37-1.31 (m, 0.5H), 1.24-1.12 (m, 1.0H) 0.90-0.86 (m, 4.0H), 0.84 (d, J = 6.60, 2.0H). HRMS (ESI) C$_{40}$H$_{47}$N$_5$O$_6$ [M + H]$^+$ calc'd = 693.3686; found = 693.3944.
See FIG. 3Q.

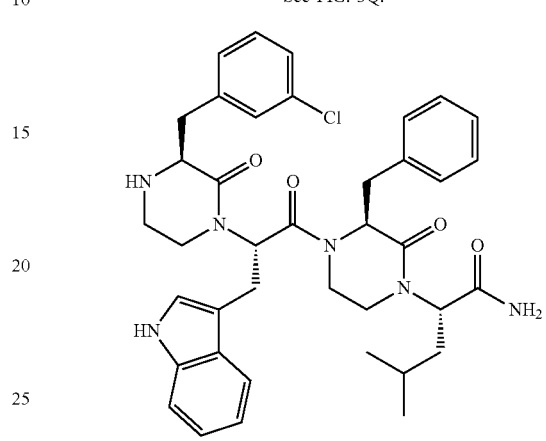

Oligooxopiperazine 18: F(3-Cl)WFL-NH$_2$
$^1$H-NMR (600 MHz, d$_6$-DMSO) δ 10.88 (s, 0.7H), 10.87 (s, 0.3H), 9.40 (br d, 2.0H), 7.57 (d, J = 7.90, 0.6H), 7.48-7.40 (m, 1.4H), 7.38-7.29 (m, 3.5H), 7.25-7.17 (m, 2.5H), 7.16-6.98 (m, 5.0H), 6.95-6.86 (m, 0.8H), 6.54 (br, 0.2H), 5.66 (dd, J = 8.77, 6.37, 0.6H), 5.30 (t, J = 7.32, 0.4H), 5.02-4.97 (m, 1.0H), 4.94 (t, J = 5.85, 0.6H), 4.70 (dd, J = 7.83, 5.33, 0.4H), 4.29 (br, 0.6H), 4.19 (dt, J = 13.17, 3.76, 0.4H), 4.07 (br, 0.4H), 3.70 (dt, J = 13.17, 3.76, 0.6H), 3.62-3.49 (m, 2.0H), 3.30-3.22 (m, 1.0H), 3.23-3.02 (m, 6.0H), 3.16-2.86 (m, 3.0H), 2.76-2.72 (m, 1.0H), 1.66-1.59 (m, 0.4H), 1.56-1.45 (m, 1.6H), 1.36-1.28 (m, 0.5H), 1.26-1.11 (m, 1.5H), 0.89-0.86 (m, 4.0H), 0.84 (d, J = 6.57, 2.0H). HRMS (ESI) C$_{39}$H$_{44}$ClN$_5$O$_5$ [M + H]$^+$ calc'd = 697.3191; found = 697.3568.
See FIG. 3R.

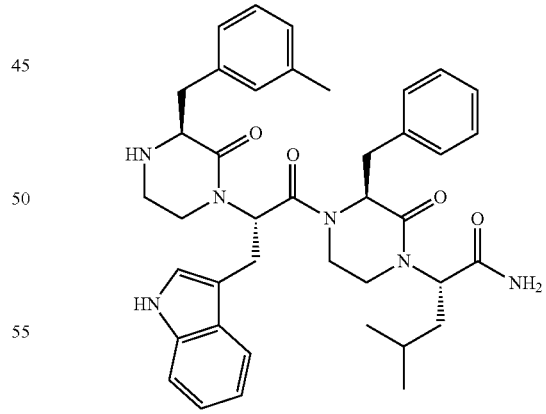

Oligooxopiperazine 19: F(3-Me)WFL-NH$_2$
$^1$H-NMR (400 MHz, d$_6$-DMSO) δ 10.88 (br, 0.6H), 10.87 (br, 0.4H), 9.18 (br d, 2.0H), 7.57 (d, J = 7.65, 0.7H), 7.47-7.39 (m, 1.3H), 7.37-7.32 (m, 1.0H), 7.25-7.18 (m, 3.0H), 7.15-7.07 (m, 3.5H), 7.06-6.97 (m, 3.5H), 6.93-6.88 (m, 1.0H), 5.67 (dd, J = 8.82, 6.07, 0.6H), 5.32 (t, J = 7.34, 0.4H) 5.02-4.97 (m, 1.0H), 4.93 (t, J = 5.68, 0.6H), 4.77-4.71 (dd, J = 7.87, 5.65, 0.4H), 4.28 (br, 0.5H),

TABLE 1-continued

Compound Characterization 4.21-4.15 (m, 0.5H), 4.08 (br, 0.5H), 3.75-3.68 (m, 1.5H), 3.39-3.04 (m, 9.0H), 3.02-2.83 (m, 2.5H), 2.79-2.73 (m, 0.5H), 2.29 (s, 3.0H), 1.69-1.59 (m, 0.5H), 1.56-1.47 (m, 2.0H), 1.39-1.27 (m, 0.5H), 1.27-1.06 (m, 2.0H), 0.90-0.86 (m, 4.0H), 0.84 (d, J = 6.54, 2.0H). HRMS (ESI) $C_{40}H_{48}N_6O_4$ $[M + H]^+$ calc'd = 677.3737; found = 677.4042.
See FIG. 3S.

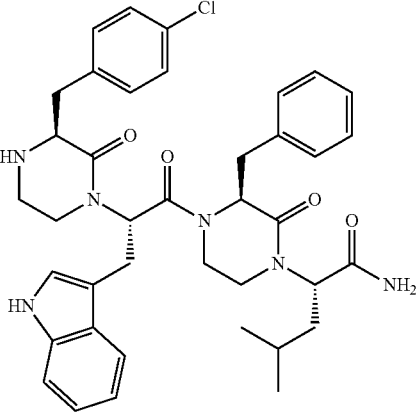 [SMILES: CC(C)C[C@@H](C(N)=O)N1CCN(C(=O)[C@H](Cc2c[nH]c3ccccc23)N2CCN[C@@H](Cc3ccc(Cl)cc3)C2=O)[C@@H](Cc2ccccc2)C1=O]

Oligooxopiperazine 20: F(4-Cl)WFL-NH$_2$
$^1$H-NMR (600 MHz, d$_6$-DMSO) δ 10.88 (s, 0.7H), 10.87 (s, 0.3H), 9.38 (br d, 2.0H), 7.57 (d, J = 7.84, 0.5H), 7.45 (s, 0.5H), 7.42 (d, J = 8.45, 1.0H), 7.34 (t, J = 7.63, 2.5H), 7.24-7.20 (m, 3.0H), 7.16-7.06 (m, 4.0H), 7.05-6.98 (m, 1.5H), 6.90 (br, 0.9H), 6.55 (br, 0.1H), 5.66 (dd, J = 8.99, 6.25, 0.6H), 5.30 (t, J = 7.32, 0.4H), 5.01-4.97 (m, 1.0H), 4.94 (t, J = 5.85, 0.6H), 4.70 (dd, J = 8.11, 5.10, 0.4H), 4.25 (br, 0.5H), 4.19 (dt, J = 13.52, 3.83, 0.4H), 4.04 (br, 0.5H), 3.72 (dt, J = 13.52, 3.83, 0.6H), 3.57 (br, 1.0H), 3.28-3.25 (m, 1.0H), 3.23-3.13 (m, 3.5H), 3.10-3.03 (m, 3.0H), 3.01-2.86 (m, 2.5H), 2.85-2.70 (m, 2.0H), 1.66-1.59 (m, 0.5H), 1.57-1.45 (m, 1.8H), 1.37-1.29 (m, 0.5H), 1.24 (br, 0.2H), 1.21-1.10 (m, 1.0H), 0.90-0.86 (m, 4.0H), 0.84 (d, J = 6.56, 2.0H). HRMS (APCI) $C_{39}H_{44}ClN_5O_5$ $[M + H]^+$ calc'd = 697.3191; found = 697.3587.
See FIG. 3T.

The following trimers were synthesized in a similar manner.

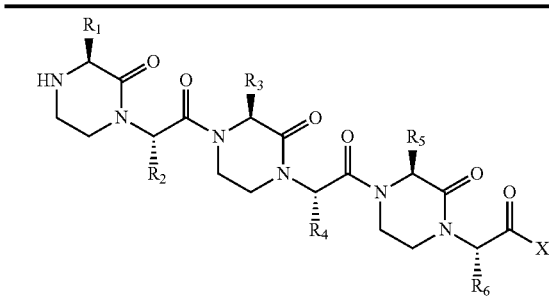

| | R$_1$ | R$_2$ | R$_3$ | R$_4$ | R$_5$ | R$_6$ | X | K$_{d2}$ (μM) | calculated mass (g/mol) | observed mass (g/mol) |
|---|---|---|---|---|---|---|---|---|---|---|
| 1 | Phe | Trp | Phe | Leu | Leu | Ala | OH | 3.1 ± 2.4 | 874.08 | 874.5 |
| 2 | Phe | Trp | Lys | Leu | Leu | Ala | OH | 244 ± 168 | 855.08 | 855.9 |

Example 3—Materials and Methods: Expression and Purification of Mdm2

Competent BL21 DE3 pLySS E. coli cells were transformed by heat shocking the bacteria at 42° C. for 1 minute in media containing a pET-14B vector containing a His6-tagged Mdm2$_{25-117}$ fusion protein. Cells were grown on ampicillin-containing agar plates (50 mg/mL), and a single culture was used to inoculate a 100 mL overnight culture of LB media containing ampicillin (50 mg/mL). 500 mL of terrific broth (4 L flask) was seeded with 25 mL of overnight culture and incubated at 30° C. for 1.5 hours before induction of protein expression with 0.4 mM IPTG. The flask was incubated at 30° C. for an additional 4.5 hours. The cells were harvest by centrifugation at 6,000 g for 20 minutes and the supernatant was discarded. The cells were resuspended in 50 mL binding buffer (0.5 M NaCl, 20 mM Tris-HCl, 5 mM imidazole, pH 7.9) and lysed by sonication in ice (10×10 seconds pulses over 2 minutes). The cells were again centrifuged at 15,000 g for 20 minutes and the resulting supernatant containing the desired Mdm2 fusion protein was purified using a His-Bind® column affinity purification kit (Novagen). The resulting protein was dialyzed in 10 mM PBS with 5 mM EDTA and 0.5 mM DTT, and characterized by SDS-PAGE analysis.

Example 4—Materials and Methods: Protein Binding Studies

The relative affinities of peptides for N-terminal His$_6$-tagged Mdm2$_{25-117}$ were determined using fluorescence polarization based competitive binding assay with fluorescein labeled p53 peptide, Flu-p53. The polarization experiments were performed with a DTX 880 Multimode Detector (Beckman) at 25° C., with excitation and emission wavelengths at 485 nm and 535 nm, respectively. All samples were prepared in 96 well plates in 0.1% pluronic F-68 (Sigma).

Figure 4:
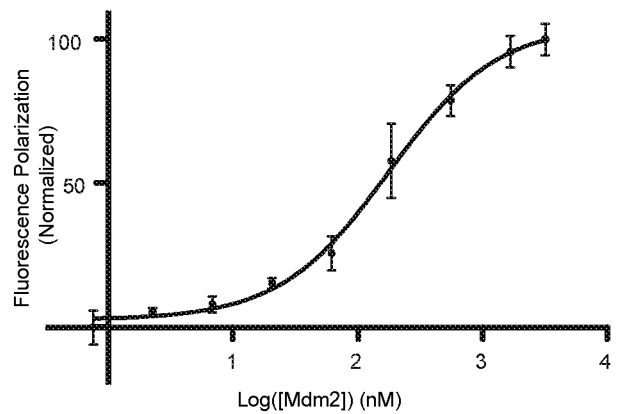
FIG. 4 is a graph of the binding of Flu-p53 to $His_6$-tagged Mdm2, determined by a fluorescence-polarization assay. Direct binding of Flu-p53 to Mdm2 is shown.
Figure 5:
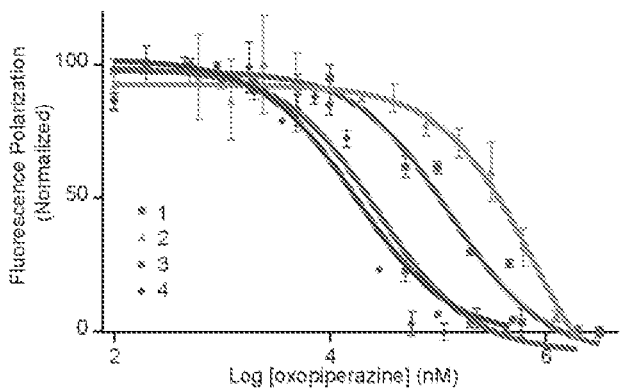
FIG. 5 is a graph relating to the determination of oxopiperazine analog binding to $His_6$-tagged Mdm2 by a fluorescence-polarization assay. Binding curves for compounds 1, 2, 3, and 4 are shown (see Table 3, infra).
Figure 6:
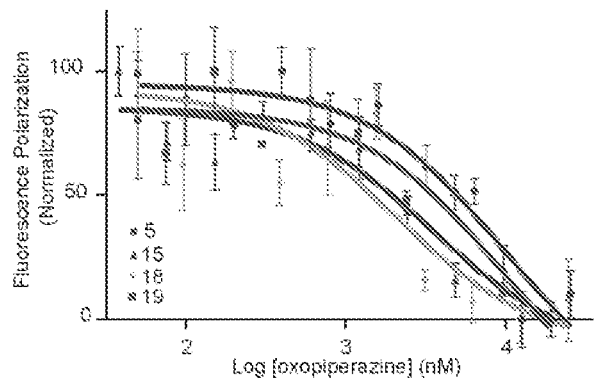
FIG. 6 is a graph relating to the determination of computationally optimized oxopiperazine analog binding to $His_6$-tagged Mdm2 by a fluorescence-polarization assay. The binding curves for compounds 5, 15, 18, and 19 are shown (see Table 6, infra).

Prior to the competition experiments, the affinity of Flu-p53 for Mdm2 was determined by monitoring polarization of the fluorescent probe upon binding Mdm2 (FIG. 4). Addition of an increasing concentration (0 nm to 3.5 μM) of Mdm2 protein to a 15 nM solution of Flu-p53 in 10 mM PBS pH 7.4, 5 mM EDTA, and 0.5 mM DTT afforded the IC$_{50}$ value, which was fit into equation (1) to calculate the dissociation constant (K$_D$) for the Mdm2/p53 complex (Roehrl et al., *Biochemistry* 43:16056 (2004), which is hereby incorporated by reference in its entirety). The K$_D$ of Flu-p53 was determined to be 169±7 nM.

$$K_D = (R_T \times (1 - F_{SB}) + L_{ST} \times F_{SB}^2)/F_{SB} - L_{ST} \quad (1)$$

where:
R$_T$=Total concentration of Mdm2
L$_{ST}$=Total concentration of fluorescent peptide
F$_{SB}$=Fraction of bound fluorescent peptide For competition binding experiments, a solution of 250 nM Mdm2 and 15 nM Flu-p53 in buffer (10 mM PBS pH 7.4, 5 mM EDTA, 0.5 mM DTT, 0.1% pluronic F-68) was incubated at 25° C. in a 96 well plate. After 30 minutes, appropriate concentrations of the oxopiperazine (1 nM-100 μM) were added to the Mdm2-Flu-p53 mixture and the resulting mixtures were incubated at 25° C. for 1 hour before measuring the degree of dissociation of Flu-p53 by polarization. The EC$_{50}$ was fit into equation (2) to calculate the K$_i$ value of the oxopiperazine. The inhibition curves are shown in FIG. 5 and FIG. 6.

$$K_i = K_{D1} * F_{SB} * ((L_T/(L_{ST} * F_{SB2} - (K_{D1} + L_{ST} + R_T) * F_{SB} + R_T)) - 1(1 - F_{SB})) \quad (2)$$

where:
$K_D = K_D$ of fluorescent probe Flu-p53
$R_T$=Total concentration of Mdm2 protein
$L_{ST}$=total concentration of p53 fluorescent peptide
$F_{SB}$=Fraction of bound oxopiperazine (at $EC_{50}$)
$L_T$=total concentration of oxopiperazine ($EC_{50}$)

The binding affinity ($K_D$) values reported for each peptide are the averages of 3-5 individual experiments, and were determined by fitting the experimental data to a sigmoidal dose-response nonlinear regression model on GraphPad Prism 5.0 (Roehrl et al., *Biochemistry* 43:16056 (2004), which is hereby incorporated by reference in its entirety).

Example 5—Materials and Methods: Docking and Design Protocol in Rosetta

The oxopiperazine dimer scaffold was initially docked by aligning Cβ atoms on the scaffold positions corresponding to hotspot residues on p53 ($R_1$: Phe19, $R_2$: Trp23, $R_3$: Leu26) using the PDB structure: 1YCR. The Rosetta relax w/constraints application was run on this initial structure to relieve any clashes that may hinder score analysis. The relaxed complex was then modeled and designed using a protocol developed specifically for oxopiperazine inhibitors. The protocol iterates between 1) a perturbation phase (conformational optimization), attempting to find the lowest energy conformation of bound ligand and Mdm2 given the current residue identities; and 2) a design phase, which attempts to find residue substitutions including noncanonical analogues that lower the energy given the current conformation. The perturbation phase consists of a) rigid body rotation and translation moves, b) small angle moves of phi and psi, and c) pucker moves of the oxopiperazine rings. Perturbations were only allowed to the scaffold, leaving the target's backbone fixed. All residues at the interface on both target and ligand were allowed to sample side-chain rotamer space. The design phase consisted of residue identity substitutions at positions along the scaffold and rotamer repacking. Substitutions were defined in the Rosetta resfile. Finally, minimization of all degrees of freedom in the complex was performed.

For modeling analysis, the same design protocol was used, except residues were fixed to the identities of interest in the Rosetta residue input file (i.e., resfile). Fixing residue identities only allows side chain optimization during the "design" phase. 5000 independent runs included noncanonical amino acids that were derivative of the original hotspot residue (e.g., $R_1$ phenylalanine was designed with 3-methyl-phenylalanine, etc.) The NCAA_library list is shown in Table 2 below.

TABLE 2

Noncanonical Amino Acid Design Library for Rosetta
Rosetta code: noncanonical amino acid name Position $R_1$ NC A12: 2.4-dimethyl-phenylalanine
NC A31: 2-amino-5-phenyl-pentanoic_acid
NC A34: 2-aminomethyl-phenylalanine
NC A43: 2-hydroxy-phenylalanine
NC A48: 2-methyl-phenylalanine
NC A68: 3-aminomethyl-phenylalanine
NC A69: 3-amino-tyrosine
NC A78: 3-hydroxy-phenylalanine
NC A80: 3-hydroxy-tyrosine

TABLE 2-continued

Noncanonical Amino Acid Design Library for Rosetta
Rosetta code: noncanonical amino acid name NC A84: 3-methyl-phenylalanine
NC A94: 4-aminomethyl-phenylalanine
NC APA: 4-amino-phenylalanine
NC B12: 4-carboxy-phenylalanine
NC B27: 4-methyl-phenylalanine
NC B30: 4-phenyl-phenylalanine
NC B31: 4-tert-butyl-phenylalanine
NC B96: beta.beta-diphenyl-alanine
NC C43: phenyl-serine
NC B67: beta-(1-naphthyl)-alanine
NC B92: beta-beta-dicyclohexyl-alanine__boat__boat
NC B93: beta-beta-dicyclohexyl-alanine__boat__chair
NC B94: beta-beta-dicyclohexyl-alanine__chair__boat
NC B95: beta-beta-dicyclohexyl-alanine__chair__chair
NC B99: beta-cyclohexyl-alanine__boat
NC C00: beta-cyclohexyl-alanine__chair
NC C01: beta-cyclopentyl-alanine
NC C02: beta-cyclopentyl-alanine__puck
NC C11: cyclohexyl-glycine__boat
NC C12: cyclohexyl-glycine__chair
NC B21: 4-hydroxy-phenylglycine
NC B44: 9-anthryl-alanine
NC B67: beta-(1-naphthyl)-alanine
NC B74: beta-(2-naphthyl)-alanine
NC C15: diphenylglycine
NC C42: phenylglycine
NC C95: 3-chloro-phenylalanine Position $R_4$ NC A30: 2-amino-4-bromo-4-pentenoic__acid
NC A91: 4.5-dehydro-leucine
NC B47: allo-isoleucine
NC C91: fluoro-leucine__ent1
NC C92: fluoro-leucine__ent2
NC C93: hexafluoro-leucine
NC C61: trifluoro-leucine
NC C94: trifluoro-leucine__ent2
NC HLU: homoleucine
NC A20: 2-allyl-glycine
NC ABA: amino-butyric acid
NC NLU: norleucine
NC NVL: norvaline For each position on the scaffold, greater than 10,000 decoys were run, allowing the single position to vary while leaving the other positions fixed. This was repeated for each position on the oxopiperazine scaffold. The SVN Revision: 52345 version of Rosetta used was for these studies. Detailed protocols including command lines have been previously described (Drew et al., *PLoS One* 8:DOI: 10.1371/journal.pone.0067051 (2013), which is hereby incorporated by reference in its entirety).

Top designs were selected based on filtering the lowest 5% of total energy decoys and sorting by Rosetta binding energy score. The Rosetta binding energy score was calculated using equation (3).

$$\text{Binding\_energy\_score} = \text{total\_score} - \text{unbound\_score} \quad (3)$$

The unbound score was calculated by separating the scaffold from the target Mdm2 structure, then repacking the side chains and finally calculating the total Rosetta energy of the unbound complex.

Example 6—Materials and Methods: Rosetta Binding Discrimination Analysis

A random set of designs targeting Mdm2 were generated from a set of over 13,000 Rosetta design runs where all four positions of an oxopiperazine dimer were allowed to vary to any canonical amino acid excluding Cys, Gly, and Pro. The top 5% of models by total Rosetta score made up the total random set. This random set is shown as a grey histogram (violin plot) in FIG. 7.

The top binding energy score for designs with experimental binding affinities were determined from a set of 5,000 decoy structures. As described above, the top 5% of decoys by total score was then sorted by Rosetta binding energy score and the lowest Rosetta binding energy score was used.

Example 7—Materials and Methods: Quantum Mechanics Calculations

Quantum mechanics calculations were done using the Gaussian 09 (EM64L-G09RevC.01, version date: 2011-09-23) software package (Gaussian 09, Revision C.01, Frisch et al. (Gaussian, Inc. 2009), which is hereby incorporated by reference in its entirety). An initial optimization using "HF 6-31G(d) Opt SCRF=PCM SCF=Tight" parameters was done for each model structure. The resulting optimized structure was then used for further energy calculations with parameters "B3LYP 6-31G(d) Geom=Check SCRF=PCM SCF=Tight" and "MP2(full) 6-31G(d) Geom=Check SCRF=PCM SCF=Tight".

Example 8—Materials and Methods: Expression and Purification of $^{15}$N-Mdm2

The pET-14B vector containing a His6-tagged Mdm2$_{25-117}$ fusion protein was transformed into BL21 (DE3) competent *E. coli* (Novagen) in M9 minimal media with $^{15}$NH$_4$Cl as the main nitrogen source. Protein production was induced with 0.4 mM IPTG at O.D.600 and incubated for 16 hours at 15° C. Bacteria were harvested and resuspended in the lysis buffer with 20 mM Phosphate buffer (Research Products International, Corp.), 100 µM DTT (Fisher), 1 mM EDTA (Sigma), 0.5% TritonX 100 (Sigma), 1 mg/mL Pepstatin A (Research Products International, Corp.), 10 mg/mL Leupeptin A (Research Products International, Corp.), 500 µM PMSF (sigma), and 0.5% glycerol at pH 8.0. Pellets were lysed by sonication and centrifuged at 4° C. at 20,000 rpm for 20 minutes. Fusion protein was collected from the bacterial supernatant and the resulting supernatant containing the desired Mdm2 fusion protein was purified using a His-Bind® column affinity purification kit (Novagen). The resulting protein was dialyzed in 10 mM PBS with 5 mM EDTA and 0.5 mM DTT, and characterized by SDS-PAGE analysis.

Example 9—Materials and Methods: $^1$H-$^{15}$N HSQC NMR Spectroscopy

Uniformly $^{15}$N-labeled N-terminal His$_6$-tagged Mdm2$_{25-117}$ was concentrated to 50 µM in NMR buffer (10 mM PBS pH 7.4, 5 mM EDTA, 0.5 mM DTT) using a 3 kDa MWCO Amicon Ultra centrifugal filter (Millipore) and supplemented with 5% D$_2$O. For HSQC titration experiments, data were collected on a 600 MHz Bruker four-channel NMR system at 25° C. and analyzed with the TopSpin software (Bruker).

For the HSQC titration experiments, 0.2 and 0.5 molar equivalents of compound 18 (F(3-Cl)WFL) in DMSO were added to $^{15}$N-labelled Mdm2, and the data were collected as described above. Mean chemical shift differences ($\Delta\delta_{NH}$) observed for $^1$H and $^{15}$N nuclei of various resonances were calculated as described in Williamson, *Prog. Nucl. Magnetic Res. Spectr.* 73:1 (2013), where α is the range of H ppm shifts divided by the range of NH ppm shifts (α=⅕).

$$d = \sqrt{\frac{1}{2}[\delta_H^2 + (\alpha \cdot \delta_N^2)]}$$

Example 10—Results and Discussion: Helix Mimetic Design and Synthesis

Oxopiperazine dimers that mimic the p53 activation domain were designed to develop ligands for Mdm2 The design and Mdm2 binding properties of oxopiperazine dimer mimetics 1-8 are shown in Table 3 below.

TABLE 3

Design and Mdm2 Binding Properties of Preliminary Oxopiperazine-Derived Helix Mimetics

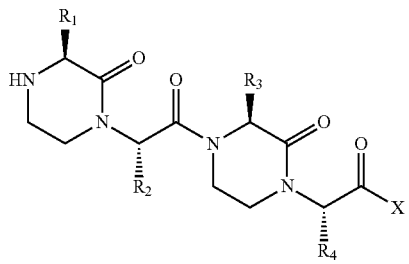

| Mimetic | R$_1$ | R$_2$ | R$_3$ | R$_4$ | X | K$_d$ (µM)$^a$ |
|---|---|---|---|---|---|---|
| 1 | Phe | Trp | Ala | Leu | OH | 65.4 ± 0.28 |
| 2 | Phe | Trp | Lys | Leu | OH | ≥200 |
| 3 | Phe | Trp | Leu | Leu | OH | 7.90 ± 0.5 |
| 4 | Phe | Trp | Phe | Leu | OH | 6.90 ± 1.3 |
| 5 | Phe | Trp | Phe | Leu | NH$_2$ | 2.88 ± 0.12 |
| 6 | Phe | Trp | Phe | Lys | NH$_2$ | ≥200 |
| 7 | Lys | Trp | Phe | Leu | NH$_2$ | ≥200 |
| 8 | Phe | Ala | Phe | Leu | NH$_2$ | 63.9 ± 6.8 |

$^a$Binding affinity for Mdm2 as determined by a competitive fluorescence polarization assay.

Oxopiperazine-dipeptide analogs were also designed. The design and Mdm2 binding properties of oxopiperazine-dipeptide analogs 9-12 are shown in Table 4 below.

TABLE 4

Design and Mdm2 Binding Properties of Oxopiperazine-Dipeptide Analogs

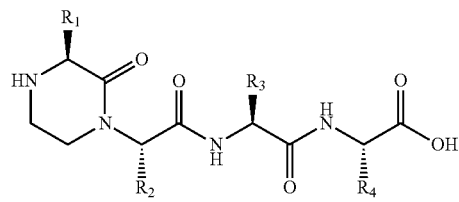

| Mimetic | R$_1$ | R$_2$ | R$_3$ | R$_4$ | K$_d$ (µm)$^a$ |
|---|---|---|---|---|---|
| 9 | Phe | Trp | Ser | Leu | >400 |
| 10 | Phe | Trp | Asp | Leu | 125 ± 73 |
| 11 | Phe | Trp | Leu | Leu | 93.7 ± 16.4 |
| 12 | Phe | Trp | Phe | Leu | 49.4 ± 10.4 |

$^a$Binding affinity for Mdm2 as determined by a competitive fluorescence polarization assay.

The p53-Mdm2 interaction is an attractive target for cancer therapeutics (Vazquez et al., *Nat. Rev. Drug Discov.* 7:979 (2008); Shangary & Wang, *Clin. Cancer Res.* 14:5318 (2008), each of which is hereby incorporated by reference in its entirety), as well as a model system for evaluating rational design strategies for inhibitor discovery. The activation domain of p53 adopts an α-helical conformation when bound to Mdm2 (Kussie et al., *Science* 274:948 (1996), which is hereby incorporated by reference in its entirety), and several classes of stabilized helices and helix mimetics have been shown to target this interaction (Plante et al., *Chem. Commun.* 5091 (2009); Shaginian et al., *J. Am. Chem. Soc.* 131:5564 (2009); Lee et al., *J. Am. Chem. Soc.* 133:676 (2011); Yin et al., *Angew. Chem. Int. Ed.* 44:2704 (2005); Bernal et al., *J. Am. Chem. Soc.* 129:2456 (2007); Fasan et al., *Angew. Chem. Int. Ed. Engl.* 43:2109 (2004); Kritzer et al., *J. Am. Chem. Soc.* 126:9468 (2004); Murray & Gellman, *Biopolymers* 88:657 (2007); Sakurai et al., *J. Am. Chem. Soc.* 128:11000 (2006), each of which is hereby incorporated by reference in its entirety). In addition, several potent small molecule inhibitors of this interaction are known and are being evaluated for their in vivo efficacy in advanced preclinical models (Yu et al., *J. Med. Chem.* 52:7970 (2009); Vassilev et al., *Science* 303:844 (2004); Reed et al., *J. Biol. Chem.* 285:10786 (2010), each of which is hereby incorporated by reference in its entirety). Lastly, a wealth of structural data on the p53-Mdm2 interaction makes it well-suited for development of computational strategies (Reynes et al., *PLoS Comput. Biol.* 6:e1000695 (2010), which is hereby incorporated by reference in its entirety) for ligand optimization (Kussie et al., *Science* 274:948 (1996); Joerger & Fersht, *Annu. Rev. Biochem.* 77:557 (2008); Popowicz et al., *Angew. Chem. Int. Ed.* 50:2680 (2011); Michelsen et al., *J. Am. Chem. Soc.* 134:17059 (2012), each of which is hereby incorporated by reference in its entirety).

Figure 8:
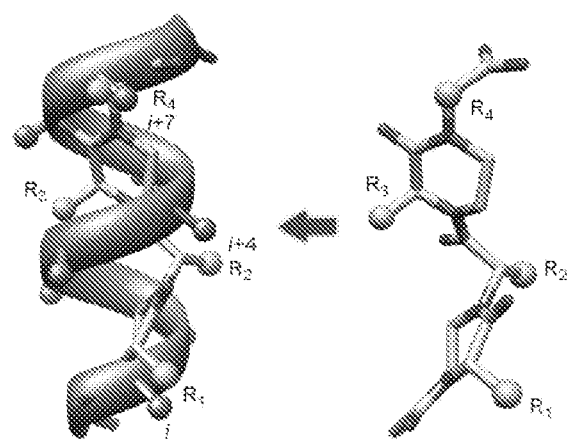
FIG. 8 shows an overlay of an 8-mer canonical α-helix and an oxopiperazine dimer (left) and the predicted low energy structure of an oxopiperazine dimer (right). Side chain groups are depicted as spheres.

The p53 activation domain targets Mdm2 with three hydrophobic residues, Phe19, Trp23, and Leu26, forming key contacts. These residues were grafted onto the oxopiperazine scaffold, as shown in FIG. 8. An oxopiperazine dimer displays four amino acid side chains.

Modeling studies suggest that the first, second, and fourth side chains, labeled $R_1$, $R_2$, and $R_4$, respectively, in FIG. 8, overlay well on the i, i+4, and i+7 side chains of the α-helix. This leaves $R_3$ potentially available for placement of solubilizing groups or small non-interacting side chains, as a preliminary analysis predicted that this residue does not directly contact the receptor. Accordingly, mimetic 1 (with the sequence FWAL) and mimetic 2 (FWKL), which feature the wild-type residues at the equivalent positions on the nonpeptidic scaffold but alanine or lysine residues at the $R_3$ position (see Table 3, supra), were designed and synthesized.

A solid phase synthesis method was developed to prepare compounds 1 and 2. A solution-based synthesis for oligooxopiperazines, which requires fourteen individual steps for the synthesis of a dimer, was previously reported (Tošovská & Arora, *Org. Lett.* 12:1588 (2010), which is hereby incorporated by reference in its entirety). Complete evaluation of the oxopiperazine scaffold as a helix mimic necessitated a solid-phase methodology. The optimized approach is shown in Scheme 1, supra, and utilizes standard Fmoc amino acids and coupling agents. Ring closure to obtain III is achieved by a Fukuyama-Mitsunobu strategy, which involves N-alkylation of amino acid residues with o-nitrobenzoyl sulfonyl chloride followed by alkylation with 2-bromoethanol Typical syntheses are performed at 0.250 mmol scale on standard chlorotrityl, Wang, or Rink amide resin to obtain dimer V as a C-terminal carboxylic acid or amide, as desired. Overall yields of the HPLC purified dimer products range from 10-20%.

A previously-described fluorescence polarization competition assay with a fluorescein-labeled p53 peptide was utilized to probe the binding affinity of the mimetics (Henchey et al., *ChemBiochem* 11:2104 (2010); Knight et al., *Anal. Biochem.* 300:230 (2002), each of which is hereby incorporated by reference in its entirety). Competitive displacement of the p53 peptides provides a strong indication that the designed nonpeptidic ligands are occupying the p53 binding pocket on Mdm2 In this assay, mimetic 1 bound Mdm2 with a dissociation constant, $K_d$, of 65 µM, while 2 displayed an appreciably lower affinity (see Table 3, supra, and FIG. 5). To examine the effect of the $R_3$ position on the binding properties, a series of compounds was designed in which this position was changed to hydrophobic, anionic, or cationic residues. These studies were performed in the context of the dimers (1-4) as well as oxopiperazine monomers linked to uncyclized dipeptides (see Table 4, supra). Together these preliminary studies showed that a hydrophobic group such as Leu or Phe at position $R_3$ is preferred. Importantly, comparisons of dimers 3 (FWLL) and 4 (FWFL) with the monomer-dipeptide sequences 11 and 12 support the hypothesis that cyclization of dipeptides in oxopiperazine rings provides a significant boost to the ability of these helix mimetics to target protein pockets Ramachandran Plots (Ramachandran & Sasisekharan, *Adv. Protein Chem.* 23:283 (1968), which is hereby incorporated by reference in its entirety) obtained from quantum mechanical calculations further illustrate the flexibility of the uncyclized derivative (FIGS. 9C-D) as compared to the cyclic dimer (FIGS. 9A-B).

In these preliminary investigations, the effect of modulating the C-terminal functional group from a carboxylic acid to a carboxamide was also studied. Comparison of 4 and 5 illustrates that C-terminal functionalities do not significantly alter the binding profile of the molecules. Mimetic 5 binds Mdm2 with a dissociation constant of roughly 3 µM. Importantly, substitution of the Trp, Phe, and Leu residues at positions $R_1$, $R_2$, and $R_4$, respectively, with alanine or lysine lead to substantial decrease in the binding affinities (5 versus 6-8); these results suggest that the residues in these positions on the dimer are making substantial contacts with the target interface and probably mimicking placement of p53 Phe19, Trp23, and Leu26 residues within the Mdm2 pocket (FIG. 10).

It was expected that the low micromolar dissociation constants obtained for this new class of helix mimetic scaffold can be further optimized, in keeping with previous studies with p53 mimics, which showed that minor changes to contact residues can provide a significant improvement in binding (Garcia-Echeverria et al., *J. Med. Chem.* 43:3205 (2000), which is hereby incorporated by reference in its entirety). However, there was a concern that cis-trans amide bond isomerization may be contributing to lower affinity. The amide bond linking the $R_2$ residue to the $R_3$ oxopiperazine ring may adopt a trans or a cis conformation. Computational studies suggest that the trans conformation is preferred over the cis conformation by roughly 1.0 kcal/mol or more depending on the identity of the $R_2$ and $R_3$ residues (Tošovská & Arora, *Org. Lett.* 12:1588 (2010), which is hereby incorporated by reference in its entirety), similar to the energy difference observed with proline. The fact that a hydrophobic group is favored over charged residues at the $R_3$ position suggests that this residue may be occupying the Leu26 binding site in Mdm2 as opposed to the $R_4$ residue.

This alternative-binding mode would be possible if the cis-amide conformation was accessed in the complex. Mimetic 6 explicitly tests this possibility. If the $R_4$ group is solvent accessible and $R_3$ binds in the Mdm2 hydrophobic pocket, 6 would be expected to bind Mdm2 with a similar affinity as 5, instead of being a rather poor binder as observed (see Table 3, supra). However, the possibility that both cis and trans conformations contribute to the overall binding affinity cannot be ruled out.

Example 11—Results and Discussion: Peptidomimetic Design with Rosetta

In order to design more potent analogs, a computational approach that combines success in computational protein design (Butterfoss & Kuhlman, Ann. Rev. Biophys. Biomolec. Struct. 35:49 (2006); Kuhlman et al., Science 302:1364 (2003); Jiang et al., Science 319:1387 (2008), each of which is hereby incorporated by reference in its entirety) with peptidomimetic scaffolds was investigated. Protein design is the process of predicting an amino acid sequence that will fold into a desired structure or carry out a desired function (Butterfoss & Kuhlman, Ann. Rev. Biophys. Biomolec. Struct. 35:49 (2006), which is hereby incorporated by reference in its entirety). Computational protein design techniques have made significant strides in recent years. A short list of successful applications includes an experimentally validated protein fold not seen in nature (Kuhlman et al., Science 302:1364 (2003), which is hereby incorporated by reference in its entirety), redesign of protein-protein and protein-DNA interfaces (Kortemme et al., Nat. Struct. Mol. Biol. 11:371 (2004), which is hereby incorporated by reference in its entirety), hyper stabilization of proteins (Korkegian et al., Science 308:857 (2005), which is hereby incorporated by reference in its entirety), and design of enzymatic and ligand binding activities (Jiang et al., Science 319:1387 (2008); Ashworth et al., Nature 441:656 (2006); Dahiyat & Mayo, Science 278:82 (1997); Harbury et al., Science 282:1462 (1998); Joachimiak et al., J. Mol. Biol. 361:195 (2006); Looger et al., Nature 423:185 (2003); Rothlisberger et al., Nature 453:190 (2008); Shifman & Mayo, Proc. Nat'l Acad. Sci. U.S.A. 100:13274 (2003), each of which is hereby incorporated by reference in its entirety). It was sought to use protein design principles to optimize the affinity of oxopiperazine mimetics using Rosetta (rosettacommons.org) (Leaver-Fay et al., Methods Enzymol. 487:545 (2011), which is hereby incorporated by reference in its entirety).

There were several significant challenges involved in modifying Rosetta to enable modeling and design of oxopiperazine scaffolds. Specifically, Rosetta's protein centric score function was modified to account for the oligooxopiperazine backbone, recent methods were employed to incorporate non-canonical amino acids in designs, core descriptions of oxopiperazine molecules were built in Rosetta's internal molecular representation, and lastly methods for conformational sampling that efficiently sample oxopiperazine conformations were built. Two key recent developments in the broader Rosetta developers community aided in this endeavor. A new molecular mechanics-based score function was recently added to Rosetta that does not rely on the protein centric knowledge-based score terms (Drew et al., PLoS One 8:DOI:10.1371/journal.pone.0067051 (2013), which is hereby incorporated by reference in its entirety). Additionally, a redevelopment of the Rosetta software suite (Leaver-Fay et al., Methods Enzymol. 487:545 (2011), which is hereby incorporated by reference in its entirety) has provided key flexibility in the data-structures that were necessary to enable modeling diverse sets of molecules other than proteins and nucleic acids. Finally, new functionality was added into Rosetta that efficiently samples various oxopiperazine conformations, including a puckering of the oxopiperazine ring (Drew et al., PLoS One 8:DOI:10.1371/journal.pone.0067051 (2013), which is hereby incorporated by reference in its entirety). This work was supported by quantum-mechanical exploration of the backbone conformations to validate backbone energy terms (Drew et al., PLoS One 8:DOI:10.1371/journal.pone.0067051 (2013), which is hereby incorporated by reference in its entirety).

The objective of computational molecular design is to reduce the total number of possible designs to a manageable number that can be efficiently synthesized and experimentally tested. An oxopiperazine dimer has four variable positions and assuming a standard library of 17 amino acids (20 canonical amino acids without Cys, Gly, and Pro), the total number of possible designs would be >83,500. This calculation does not account for noncanonical amino acids, whose inclusion significantly raises the number of potential designs. Experimentally synthesizing and testing this many designs would be prohibitive for academic labs. Rosetta computational design reduces the number of total designs one must synthesize to obtain potent ligands and streamlines the process of finding a high affinity binder.

Figure 2:
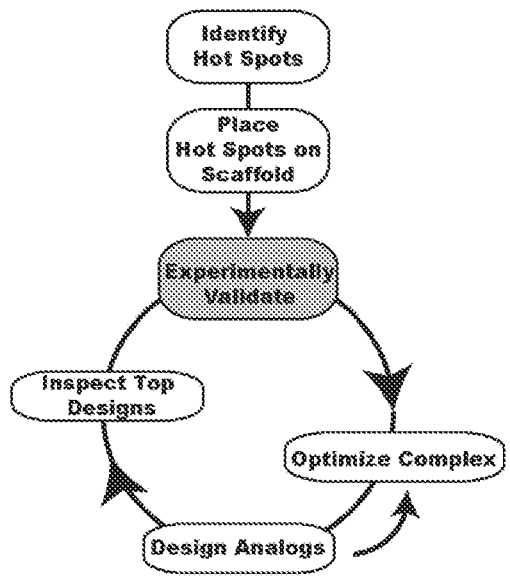
FIG. 2 illustrates the key steps in the inhibitor design protocol. The protocol is initiated with identification of hotspot residues at the native interface by computational alanine scans. Positions on the scaffold are identified to mimic hotspot residues, and the scaffold featuring the hotspot mimics is experimentally validated. Computational steps including optimization of the ligand-protein complex conformation and design of hotspot analogs are performed using Rosetta. Top designs are inspected for proper binding of the target interface and proper designs are experimentally validated.

The basic design protocol in Rosetta uses a fixed backbone template, with the goal of identifying the set of residues and side chain conformations with the lowest energy (FIG. 2). To reduce the computational complexity required to model side chain degrees of freedom, the side chains are represented as "rotamers"—discrete side chain conformations located at the centroids of chi angle clusters, as determined by analyzing experimental protein structures. Recent extensions of the Rosetta framework enable modeling and design of noncanonical backbones on nonnatural scaffolds such as peptoids (Drew et al., PLoS One 8:DOI:10.1371/journal.pone.0067051 (2013); Butterfoss et al., J. Am. Chem. Soc. 131:16798 (2009), each of which is hereby incorporated by reference in its entirety). Implementation of oxopiperazine design in Rosetta has been recently described and the protocols are available on the web (http://rosie.rosettacommons.org) (Lyskov et al., PLoS One 8:e63906 (2013), which is hereby incorporated by reference in its entirety). Here, the previous webserver implementation was expanded on by allowing larger rigid body sampling and designs, which include noncanonical amino acids.

Figure 11:
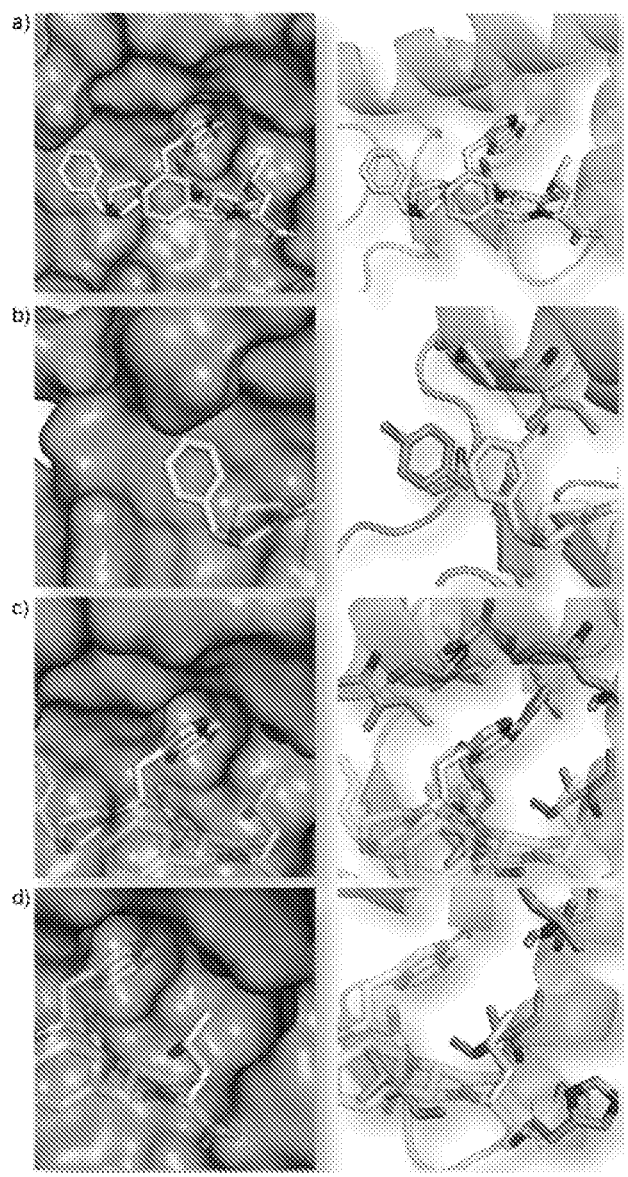
FIGS. 11A-D relate to the predicted conformation of mimetic 5 in the Mdm2 pocket.

The computational design protocol in Rosetta was begun by building a model of compound 5 and by analyzing the experimental structure activity relationships shown in Table 3. Compound 5 was docked to align with the p53 hotspot residues, and an oxopiperazine docking protocol was used to optimize the rigid body conformations of the ligand and the protein based on Rosetta's molecular mechanics energy function. FIG. 11A shows that 5 makes several energetically favorable contacts with the Mdm2 interface, suggesting proper mimicry of the p53 hotspot residues. The $R_1$ residue, Phe, of 5 (FIG. 11B) is involved in good packing interactions with the Mdm2 interface (residues Ile61, Met62, and Tyr67), including a potential stacking interaction with Tyr67. The $R_2$ residue, Trp (FIG. 11C), is well packed in the same pocket as the p53 hotspot Trp23, contacting Mdm2 residues Leu54, Leu57, Gly58, Ile61, Phe86, Phe91, Val93, Ile99, and Ile103. Lastly, the $R_4$ residue, Leu (FIG. 11D), also properly mimics the p53 hotspot residue (Leu26), packing well into a pocket formed by several Mdm2 hydrophobic interface residues including Leu54, Val93, His96, Ile99, and Ile103.

Next, an algorithm was developed to predict high affinity oxopiperazine dimers for Mdm2 using Rosetta and a library of noncanonical amino acids (see Table 2, supra). The starting conformation of the ligand-Mdm2 complex (developed as in the modeling of compound 5, FIG. 11A) was used as input for Rosetta calculations, and a two-step iterative protocol consisting of conformation and sequence optimization steps was designed.

The conformation optimization step attempts to find a low energy conformation between the scaffold and the target protein. During this step, the protocol performs a Monte Carlo search of conformational space making random changes to the rigid body orientation, oxopiperazine backbone (including ring puckering), and side chain repacking to both the scaffold and target interface. In the sequence optimization step, side chain substitutions from a library of both natural and noncanonical amino acids were made to find the lowest energy oxopiperazine sequence.

This two-step protocol was repeated for a large number of substitutions and lowest energy oxopiperazine-sequences (designs) and their 3D models were saved. Low energy designs were sorted based on calculated binding energy (FIG. 7 and Table 5 below) and the top designs were selected for manual inspection.

TABLE 5

Rosetta Predicted Binding Energy vs. Experimental $K_d$ (μM).

| $K_d$ (μM) | Binding Energy | Sequence |
|---|---|---|
| 0.33 | −8.7 | F(3-Cl)WFL |
| 2.46 | −8.4 | FWFNle |
| 65.4 | −7.91 | FWAL |
| 2.6 | −7.9 | F(3-Me)WFL |
| 0.4 | −7.3 | YWFL |
| 1.29 | −6.2 | F(4-Cl)WFL |
| 2.88 | −5.1 | FWFL |
| 0.85 | −5 | NapWFL |
| 63.9 | −4.5 | FAFL |
| 200 | −4.5 | KWFL |
| 200 | 5.48 | FWFK |

Manual inspection included verifying that 1) the oxopiperazine scaffold occupied the same pockets as the p53 helix hotspots to ensure inhibition, 2) the conformation entailed good packing amongst side chains from both sides of the interface, and 3) the designed noncanonical residues were commercially available.

Figure 7:
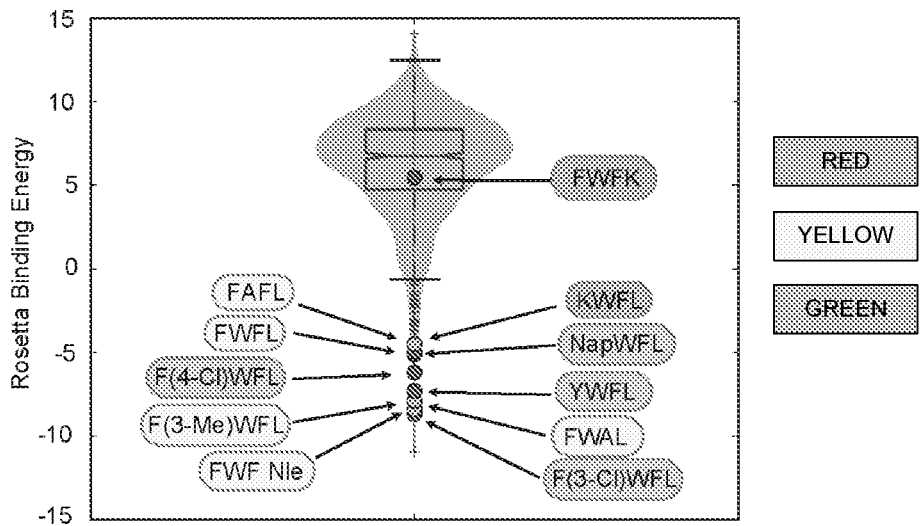
FIG. 7 is a violin plot showing the distribution of the predicted oxopiperazine analogs for their potential to target Mdm2 The binding affinity is expressed as Rosetta binding energy unit (REU). The plot shows the energy scores for a random set (grey violin) as well as experimentally tested designs (dots). The Rosetta score discriminates between good binders (green and yellow label) and weak binders (red label).

Rosetta predicts a large number of binders for Mdm2 and provides a filtered list of predicted high affinity binders composed of natural and noncanonical residues. FIG. 7 shows a violin plot in gray indicating the distribution of predicted oxopiperazine ligands spanning the Rosetta binding energy score spectrum. This spectrum provides a background on which to compare possible high affinity Rosetta designs. FIG. 12 correlates experimental binding affinity with Rosetta binding energy score. This data illustrates that Rosetta can accurately predict dissociation constants for oxopiperazines.

To show that the Rosetta binding energy protocol enriches for high affinity binders, selected designs were synthesized and evaluated using the fluorescence polarization competition assay described above. The Rosetta results suggest that the tryptophan residue at position $R_2$ is optimized for that position so we began by synthesizing the variants at each of the other three positions (Table 6 below; see FIG. 6). Mimetic 13 contains a norleucine residue at position $R_4$ in place of the leucine in 5, while compound 14 features a tyrosine group at $R_3$ in place of phenylalanine. Two derivatives, 15 and 16, containing napthylalanine and tyrosine residues, respectively, at position $R_1$ were synthesized. Binding studies indicate that substitutions at the $R_3$ and $R_4$ positions of dimers do not lead to higher affinity compounds. In contrast, substitutions at the $R_1$ position provided improvements predicted by Rosetta. The naphthyl analog, 15, binds Mdm2 with a three-fold higher affinity than 5, while substitution with tyrosine to obtain 16 provides a 400 nM ligand for Mdm2 Based on these results, two more derivatives of phenylalanine at the $R_1$ position were prepared and tested. Mimetic 17 contains a methylated tyrosine group while 18 features a 3-chloro-phenylalanine residue. Both of these analogs proved to be slightly better than 16. Overall, the designs involving changes at the $R_1$ position yielded a roughly 10-fold improvement over 5.

TABLE 6

Computationally-Predicted Oxopiperazine p53 Mimics and Their Potential to Target Mdm2

| Mimetic | $R_1$ | $R_2$ | $R_3$ | $R_4$ | X | $K_d$ (μM)$^a$ |
|---|---|---|---|---|---|---|
| 13 | Phe | Trp | Phe | Nle | $NH_2$ | 2.46 ± 0.520 |
| 14 | Phe | Trp | Tyr | Leu | $NH_2$ | 3.10 ± 0.200 |
| 15 | Nap | Trp | Phe | Leu | $NH_2$ | 0.850 ± 0.07 |
| 16 | Tyr | Trp | Phe | Leu | $NH_2$ | 0.400 ± 0.050 |
| 17 | Tyr(O—Me) | Trp | Phe | Leu | $NH_2$ | 0.320 ± 0.010 |
| 18 | Phe(3-Cl) | Trp | Phe | Leu | $NH_2$ | 0.330 ± 0.036 |
| 19 | Phe(3-Me) | Trp | Phe | Leu | $NH_2$ | 2.60 ± 0.04 |
| 20 | Phe(4-Cl) | Trp | Phe | Leu | $NH_2$ | 1.29 ± 0.060 |

$^a$Binding affinity for Mdm2 as determined by a competitive fluorescence polarization assay.

It is interesting to note that the poor binder, KWFL (7), scored better than expected by Rosetta. Examination of the Mdm2-bound structure of KWFL (see FIGS. 13A-B) reveals that the lysine residue does not occupy the p53 Phe19 hotspot pocket, violating the first rule of manual inspection described above. It is not surprising that this compound leads to poor inhibition since the Phe19 pocket offers an important contact for p53. This result underscores the importance of targeting the interaction interface when developing an inhibitor. The algorithm correctly predicted that mimetic 6, in which a lysine group resides in place of leucine, would be a poor binder. The Rosetta algorithm is unable to accurately differentiate between experimental binding affinities within one order of magnitude, but produced a pool dramatically enriched for high affinity binders. The divergence in experimental and computational results within a narrow window of affinities is not surprising in these preliminary studies that represent the first test of Rosetta on a novel backbone that includes noncanonical amino acids. It is predicted that a better correlation will be possible in future studies when a larger set of experimental data is available as a training set (Kellogg et al., Proteins 79:830 (2011), which is hereby incorporated by reference in its entirety). The full list of Rosetta scores and experimental binding affinities for the p53 mimics is shown in Table 5, supra.

Analyses of the minimized complexes show that the Phe residue at the $R_1$ position of 5 is wedged in a pocket formed by Ile61, Met62, Tyr67, and Gln72 of Mdm2 Tyr67 and Gln72 reside on a flexible loop allowing different sized analogs of Phe to be accommodated in the pocket (FIG. 14A). The predicted orientation of the $R_1$ residue for compounds 5, 15, 16, and 18 are shown in FIGS. 14B-E, respectively, and illustrate the plasticity of the pocket. Two control compounds, 19 and 20, were designed to investigate the specificity of the pocket for a 3-chloro-phenylalanine group. Mimetic 19 contains a bulkier methyl group in place of the chlorine atom, while 20 features the chlorine atom at the 4-position. Replacement of the chlorine atom with the methyl group was found to cause an 8-fold decrease in binding affinity and moving it to the para-position on the phenyl ring led to a 4-fold reduction. These results suggest that the 3-chlorophenyl group makes specific steric and electronic contacts within the pocket.

Figure 15:
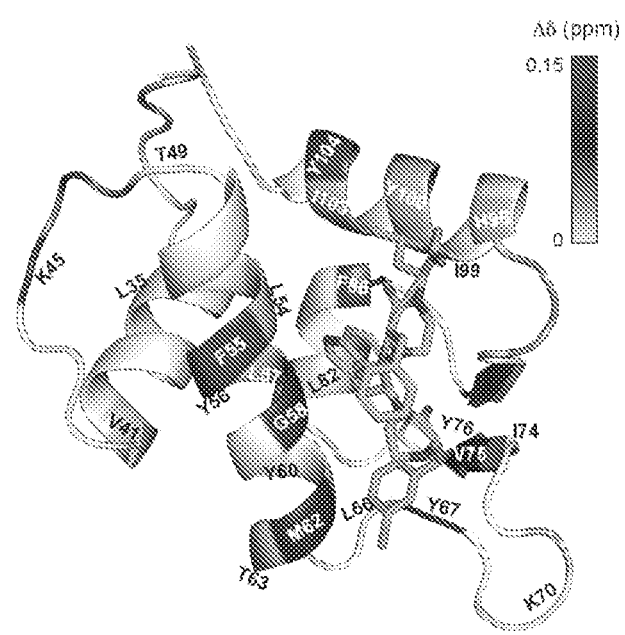
FIG. 15 is a model depicting the results of a $^1H$-$^{15}N$ HSQC NMR titration experiment. Mdm2 residues undergoing chemical shift perturbations upon addition of 18 are shown in colors that match the magnitude of the chemical shift change in the scale. The computationally predicted model of the complex is shown.
Figure 16A:
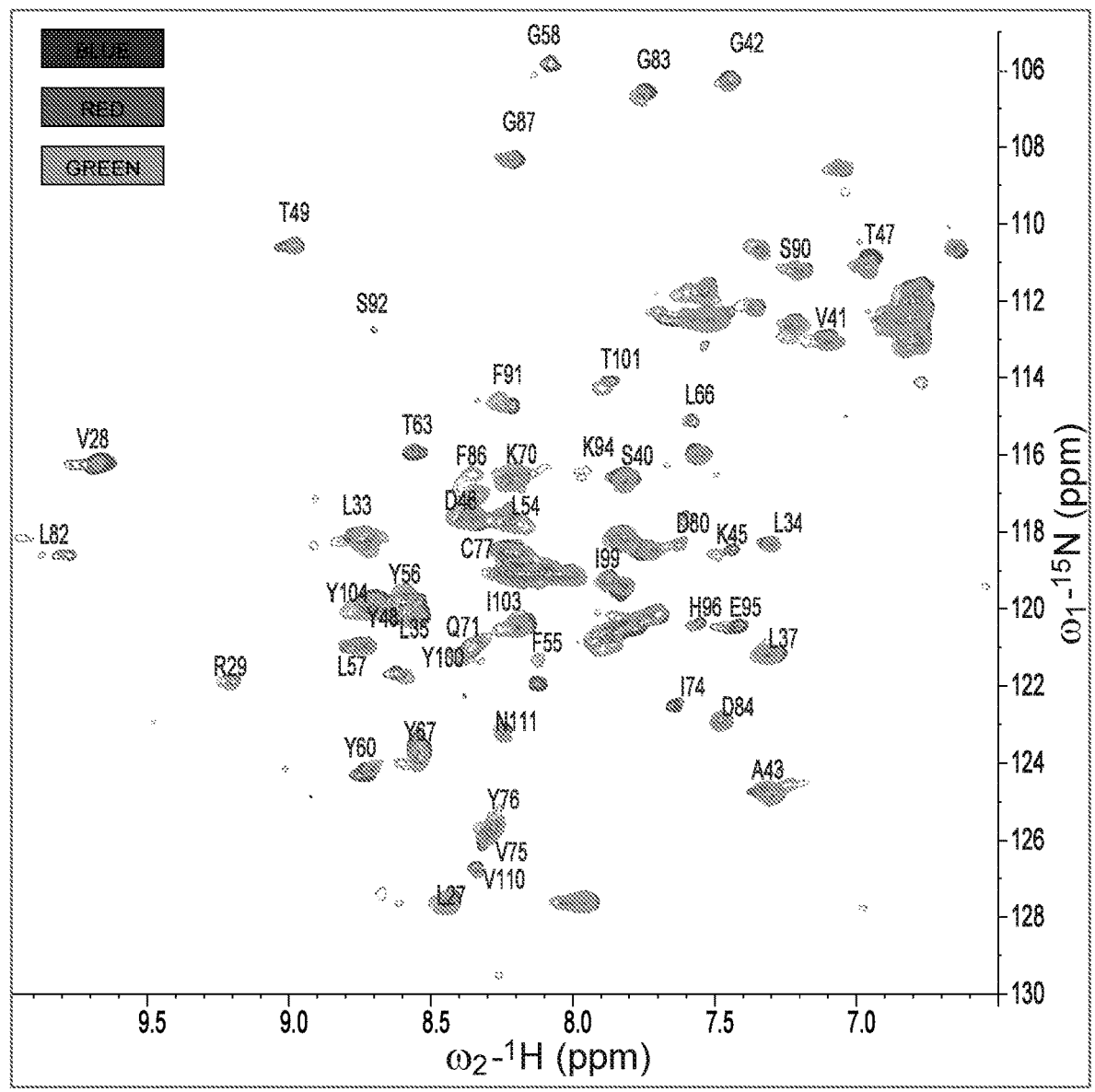
FIGS. 16A-B relate to $^1$H-$^{15}$N HSQC titration spectra.
Figure 16B:
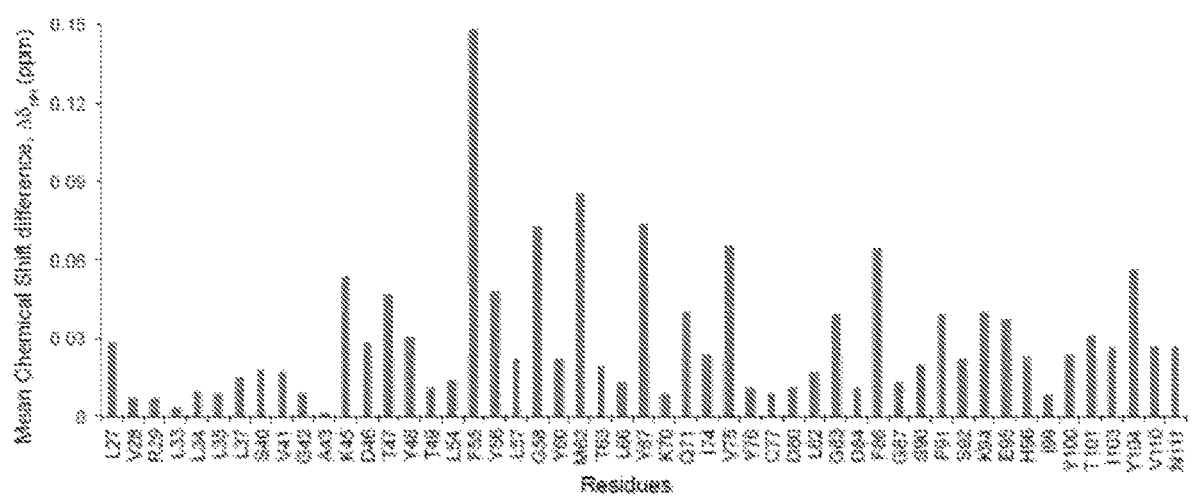

To confirm that 18 binds to Mdm2 in the p53 binding pocket, $^1$H-$^{15}$N HSQC NMR titration experiments were performed with 18 and uniformly $^{15}$N-labeled Mdm2 Addition of 18 to 50 µM Mdm2 in Mdm2:18 ratios of 1:0.2 and 1:0.5 provided a concentration-dependent shift in resonances of several Mdm2 residues (FIGS. 15 and 16A-B). Specifically, addition of 18 led to shifts in resonances of residues corresponding to the hydrophobic cleft into which the native p53 helix binds. Overall, the NMR results supported the Rosetta derived model of the complex.

Protein-protein interactions are attractive targets for drug design because of their fundamental role in human biology and disease progression. These large interfaces are often dismissed as "undruggable". However, the past decade has seen emerging methods to inhibit these complexes. A systematic examination of helical protein interfaces was undertaken to identify those that may be amenable to disruption by synthetic ligands (Jochim & Arora, *ACS Chem. Biol.* 5:919 (2010); Bullock et al., *J. Am. Chem. Soc.* 133:14220 (2011), each of which is hereby incorporated by reference in its entirety). The synthetic approach centers on the hypothesis that relative positioning and energetic contributions of "hot spot" residues determine the type of inhibitor most appropriate for the particular interface (Jochim & Arora, *ACS Chem. Biol.* 5:919 (2010), which is hereby incorporated by reference in its entirety). Described herein is a new class of helix mimetic derived from the oxopiperazine scaffold to target protein complexes where one face of the interfacial helix contributes significantly to binding. It was found that the affinity of the designed ligands can be enhanced 200-fold using a combination of computational design and experimental structure-activity relationship data. Central to the present efforts was a novel combination of rational design (i.e., hotspot mimicry) and a new set of Rosetta functionalities for computational design with non-canonical side chains and backbones. The tools and algorithms described herein will be applicable for targeting PPIs that remain intractable for synthetic inhibition. These efforts show that the principles of computational protein design can be transferred to nonnatural scaffolds featuring noncanonical amino acid residues.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. An oligooxopiperazine having a formula selected from the group consisting of:
(i) Formula IA:

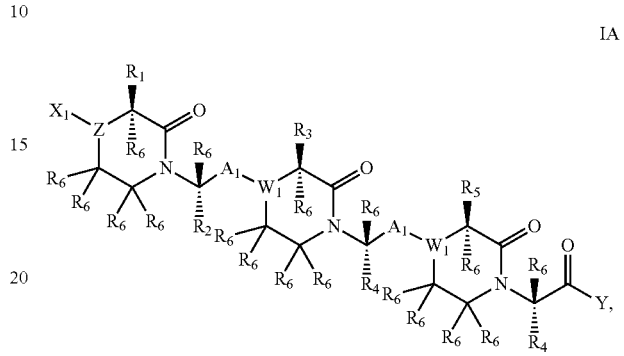

wherein:
$R_1$ is a side chain of a non-natural amino acid selected from the group consisting of Tyr(O—R'), —CH$_2$-naphthyl, 3-halo-Phe, 4-halo-Phe, 3-R'-Phe, and 4-R'-Phe, wherein R' is an alkyl, an aryl, an arylalkyl, a cycloalkyl, or a heteroaryl;

$R_2$ is an aromatic amino acid side chain or a side chain of an amino acid selected from the group consisting of Leu, Phe, Met, Trp, Ile, Val, Ser, Tyr, Tyr(O—R'), —CH$_2$-naphthyl, 2-halo-Phe, 3-halo-Phe, 4-halo-Phe, 2-R'-Phe, 3-R'-Phe, and 4-R'-Phe, wherein R' is an alkyl, an aryl, an arylalkyl, a cycloalkyl, or a heteroaryl;

$R_3$ is an alkyl, aryl, or a side chain of an amino acid selected from the group consisting of Ala, Leu, Phe, Met, Trp, Ile, Val, Ser, Tyr, Asp, Glu, Asn, Gln, Cys, His, Thr, and Arg;

$R_4$ is a solubilizing group, a hydrophobic amino acid side chain, H, N(R)$_2$, OR, halogen, an alkyl, an aryl, or a side chain of an amino acid selected from the group consisting of Leu, Ile, Val, Ala, Ser, Met, and Nle; wherein each R is independently H, an alkyl, or an aryl;

$R_5$ is an alkyl other than methyl or a side chain of an amino acid selected from the group consisting of Leu, Phe, Met, Trp, Ile, Val, Ser, Tyr, Tyr(O—R'), —CH$_2$-naphthyl, 2-halo-Phe, 3-halo-Phe, 4-halo-Phe, 2-R'-Phe, 3-R'-Phe, and 4-R'-Phe, wherein R' is an alkyl, an aryl, an arylalkyl, a cycloalkyl, or a heteroaryl;

each $R_6$ is independently H, halogen, an alkyl, or an aryl;

$R_7$ is a solubilizing group, a hydrophobic amino acid side chain, H, N(R)$_2$, OR, halogen, an alkyl, an aryl, or a side chain of an amino acid selected from the group consisting of Leu, Ile, Val, Ala, Ser, Met, and Nle; wherein each R is independently H, an alkyl, or an aryl;

$X_1$ is H, N(R)$_2$, OR, COR', CO$_2$R', an alkyl, an aryl, an arylalkyl, a cycloalkyl, a heteroaryl, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of an amine, a solubilizing group, a targeting moiety, or a tag; wherein each R is independently H, an alkyl, or an aryl; and wherein R' is H, an alkyl, an aryl, an arylalkyl, a cycloalkyl, a heteroaryl, a targeting moiety, or a tag; with the proviso that $X_1$ is absent when Z is O or S;

Z is N, O, or S;

each $A_1$-$W_1$ is independently:

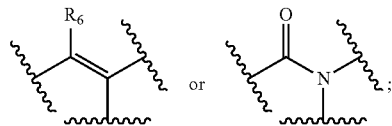

and

Y is OR', COR', N(R''')$_2$, an alkyl, an aryl, an arylalkyl, a cycloalkyl, a heteroaryl, an amino acid, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, CO$_2$R', an alkyl, an aryl, an arylalkyl, a cycloalkyl, a heteroaryl, a targeting moiety, or a tag;

(ii) Formula IB:

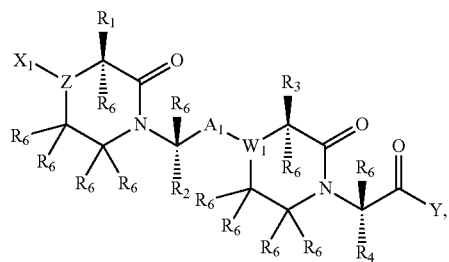

wherein:

$R_1$ is a side chain of a non-natural amino acid selected from the group consisting of Tyr(O—R'), —CH$_2$-naphthyl, 3-halo-Phe, 4-halo-Phe, 3-R'-Phe, and 4-R'-Phe, wherein R' is an alkyl, an aryl, an arylalkyl, a cycloalkyl, or a heteroaryl;

$R_2$ is an aromatic amino acid side chain or a side chain of an amino acid selected from the group consisting of Leu, Phe, Met, Trp, Ile, Val, Ser, Tyr, Tyr(O—R'), —CH$_2$-naphthyl, 2-halo-Phe, 3-halo-Phe, 4-halo-Phe, 2-R'-Phe, 3-R'-Phe, and 4-R'-Phe, wherein R' is an alkyl, an aryl, an arylalkyl, a cycloalkyl, or a heteroaryl;

$R_3$ is an alkyl, aryl, or a side chain of an amino acid selected from the group consisting of Ala, Leu, Phe, Met, Trp, Ile, Val, Ser, Tyr, Tyr(O—R'), —CH$_2$-naphthyl, 2-halo-Phe, 3-halo-Phe, 4-halo-Phe, 2-R'-Phe, 3-R'-Phe, and 4-R'-Phe, wherein R' is an alkyl, an aryl, an arylalkyl, a cycloalkyl, or a heteroaryl;

$R_4$ is an alkyl other than methyl or a side chain of an amino acid selected from the group consisting of Leu, Ile, Val, Ser, Met, and Nle;

each $R_6$ is independently H, halogen, an alkyl, or an aryl;

$X_1$ is H, N(R)$_2$, OR, COR', CO$_2$R', an alkyl, an aryl, an arylalkyl, a cycloalkyl, a heteroaryl, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of an amine, a solubilizing group, a targeting moiety, or a tag; wherein each R is independently H, an alkyl, or an aryl; and wherein R' is H, an alkyl, an aryl, an arylalkyl, a cycloalkyl, a heteroaryl, a targeting moiety, or a tag; with the proviso that $X_1$ is absent when Z is O or S;

Z is N, O, or S;

$A_1$-$W_1$ is:

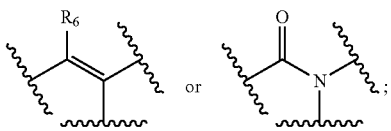

and

Y is OR', COR', N(R''')$_2$, an alkyl, an aryl, an arylalkyl, a cycloalkyl, a heteroaryl, an amino acid, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, CO$_2$R', an alkyl, an aryl, an arylalkyl, a cycloalkyl, a heteroaryl, a targeting moiety, or a tag;

(iii) Formula IC:

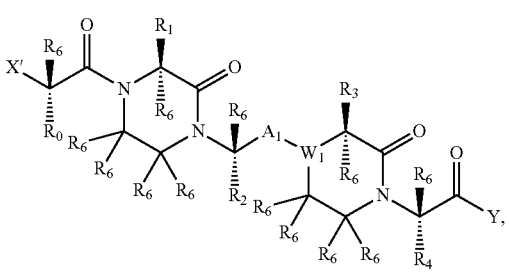

wherein:

$R_0$ is a side chain of a non-natural amino acid selected from the group consisting of Tyr(O—R'), —CH$_2$-naphthyl, 3-halo-Phe, 4-halo-Phe, 3-R'-Phe, and 4-R'-Phe, wherein R' is an alkyl, an aryl, an arylalkyl, a cycloalkyl, or a heteroaryl;

$R_3$ is an aromatic amino acid side chain or a side chain of an amino acid selected from the group consisting of Leu, Phe, Met, Trp, Ile, Val, Ser, Tyr, Tyr(O—R'), —CH$_2$-naphthyl, 2-halo-Phe, 3-halo-Phe, 4-halo-Phe, 2-R'-Phe, 3-R'-Phe, and 4-R'-Phe, wherein R' is an alkyl, an aryl, an arylalkyl, a cycloalkyl, or a heteroaryl;

$R_1$ is a solubilizing group, a hydrophobic amino acid side chain, H, $N(R)_2$, OR, halogen, an alkyl, an aryl, or a side chain of an amino acid selected from the group consisting of Ala, Leu, Phe, Met, Trp, Ile, Val, Ser, Tyr, Asp, Glu, Asn, Gln, Cys, His, Thr, and Arg; wherein each R is independently H, an alkyl, or an aryl;

$R_2$ is a solubilizing group, a hydrophobic amino acid side chain, H, $N(R)_2$, OR, halogen, an alkyl, an aryl, or a side chain of an amino acid selected from the group consisting of Ala, Leu, Phe, Met, Trp, Ile, Val, Ser, Tyr, Tyr(O—R'), —CH$_2$-naphthyl, 2-halo-Phe, 3-halo-Phe, 4-halo-Phe, 2-R'-Phe, 3-R'-Phe, and 4-R'-Phe; wherein each R is independently H, an alkyl, or an aryl and wherein R' is an alkyl, an aryl, an arylalkyl, a cycloalkyl, or a heteroaryl;

$R_4$ is an alkyl other than methyl or a side chain of an amino acid selected from the group consisting of Leu, Ile, Val, Ser, Met, and Nle;

each $R_6$ is independently H, halogen, an alkyl, or an aryl;

X' is H, COR', CO$_2$R', OR', N(R")$_2$, an alkyl, an aryl, an arylalkyl, a cycloalkyl, a heteroaryl, a solubilizing group, a targeting moiety, or a tag; wherein R' is H, an alkyl, an aryl, an arylalkyl, a cycloalkyl, a heteroaryl, an amino acid residue, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a targeting moiety, or a tag; and wherein each R" is independently H, CO$_2$R', an alkyl, an aryl, an arylalkyl, a cycloalkyl, a heteroaryl, a targeting moiety, or a tag;

$A_1$-$W_1$ is:

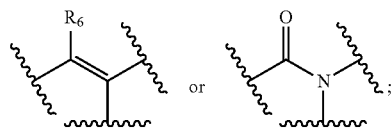

and

Y is OR', COR', N(R''')$_2$, an alkyl, an aryl, an arylalkyl, a cycloalkyl, a heteroaryl, an amino acid, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, CO$_2$R', an alkyl, an aryl, an arylalkyl, a cycloalkyl, a heteroaryl, a targeting moiety, or a tag.

2. The oligooxopiperazine according to claim 1, wherein the oligooxoperazine has a formula of Formula IA.

3. The oligooxopiperazine according to claim 2, wherein:
$R_2$ and $R_5$ are each independently a side chain of an amino acid selected from the group consisting of Leu, Phe, Met, Trp, Ile, Val, Ser, Tyr, Tyr(O—R'), —CH$_2$-naphthyl, 2-halo-Phe, 3-halo-Phe, 4-halo-Phe, 2-R'-Phe, 3-R'-Phe, and 4-R'-Phe;

$R_3$ is a side chain of an amino acid selected from the group consisting of Ala, Leu, Phe, Met, Trp, Ile, Val, Ser, Tyr, Asp, Glu, Asn, Gln, Cys, His, Thr, and Arg;

$R_4$ and $R_7$ are each independently a side chain of an amino acid selected from the group consisting of Leu, Ile, Val, Ala, Ser, Met, and Nle; and Y is OH, OR', N(R''')$_2$, or NH$_2$.

4. The oligooxopiperazine according to claim 1, wherein the oligooxoperazine has a formula of Formula IB.

5. The oligooxopiperazine according to claim 4, wherein:
$R_2$ is a side chain of an amino acid selected from the group consisting of Leu, Phe, Met, Trp, Ile, Val, Ser, Tyr, Tyr(O—R'), —CH$_2$-naphthyl, 2-halo-Phe, 3-halo-Phe, 4-halo-Phe, 2-R'-Phe, 3-R'-Phe, and 4-R'-Phe;

$R_3$ is a side chain of an amino acid selected from the group consisting of Ala, Leu, Phe, Met, Trp, Ile, Val, Ser, Tyr, Tyr(O—R'), —CH$_2$-naphthyl, 2-halo-Phe, 3-halo-Phe, 4-halo-Phe, 2-R'-Phe, 3-R'-Phe, and 4-R'-Phe;

$R_4$ is a side chain of an amino acid selected from the group consisting of Leu, Ile, Val, Ser, Met, and Nle; and Y is OH, OR', N(R''')$_2$, or NH$_2$.

6. The oligooxopiperazine according to claim 1, wherein the oligooxoperazine has a formula of Formula IC.

7. The oligooxopiperazine according to claim 6, wherein:
$R_3$ is a side chain of an amino acid selected from the group consisting of Leu, Phe, Met, Trp, Ile, Val, Ser, Tyr, Tyr(O—R'), —CH$_2$-naphthyl, 2-halo-Phe, 3-halo-Phe, 4-halo-Phe, 2-R'-Phe, 3-R'-Phe, and 4-R'-Phe;

$R_1$ is a side chain of an amino acid selected from the group consisting of Ala, Leu, Phe, Met, Trp, Ile, Val, Ser, Tyr, Asp, Glu, Asn, Gln, Cys, His, Thr, and Arg;

$R_2$ is a side chain of an amino acid selected from the group consisting of Ala, Leu, Phe, Met, Trp, Ile, Val, Ser, Tyr, Tyr(O—R'), —CH$_2$-naphthyl, 2-halo-Phe, 3-halo-Phe, 4-halo-Phe, 2-R'-Phe, 3-R'-Phe, and 4-R'-Phe;

$R_4$ is a side chain of an amino acid selected from the group consisting of Leu, Ile, Val, Ser, Met, and Nle; and Y is OH, OR', N(R''')$_2$, or NH$_2$.

8. The oligooxopiperazine according to claim 1, wherein:
(i) the oligooxoperazine has a formula of Formula IA, wherein $R_1$ is a side chain of an amino acid selected from the group consisting of Tyr(O-Me), —CH$_2$-naphthyl, 3-halo-Phe, 4-halo-Phe, 3-Me-Phe, and 4-Me-Phe;

(ii) the oligooxoperazine has a formula of Formula IB, wherein $R_1$ is a side chain of an amino acid selected from the group consisting of Tyr(O-Me), —CH$_2$-naphthyl, 3-halo-Phe, 4-halo-Phe, 3-Me-Phe, and 4-Me-Phe; or (iii) the oligooxoperazine has a formula of Formula IC, wherein $R_0$ is a side chain of an amino acid selected from the group consisting of Tyr(O-Me), —CH$_2$-naphthyl, 3-halo-Phe, 4-halo-Phe, 3-Me-Phe, and 4-Me-Phe.

9. The oligooxopiperazine according to claim 1, wherein the oligooxopiperazine is selected from the group consisting of Oligooxopiperazine 15, Oligooxopiperazine 17, Oligooxopiperazine 18, Oligooxopiperazine 19, and Oligooxopiperazine 20:

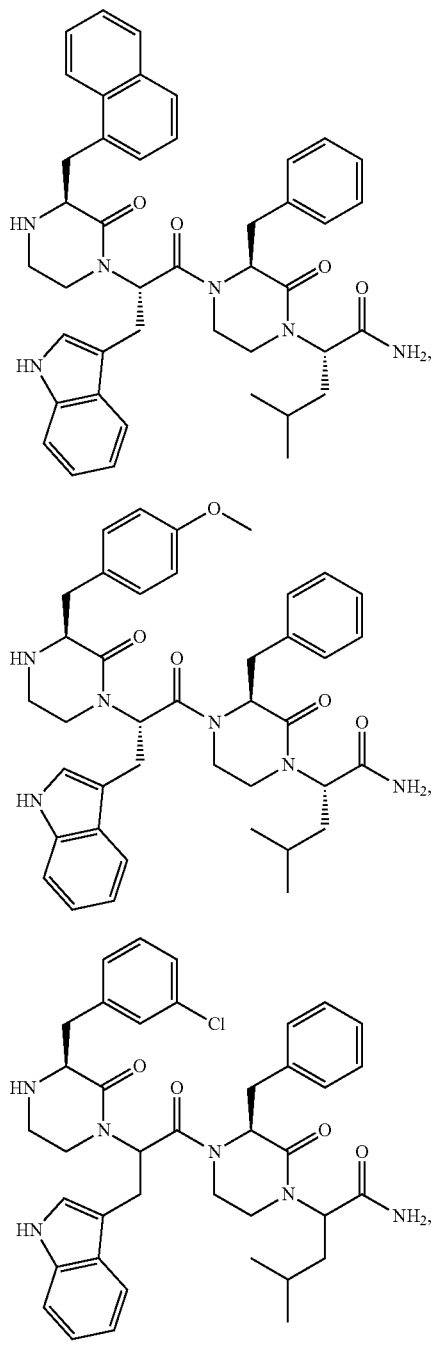
-continued
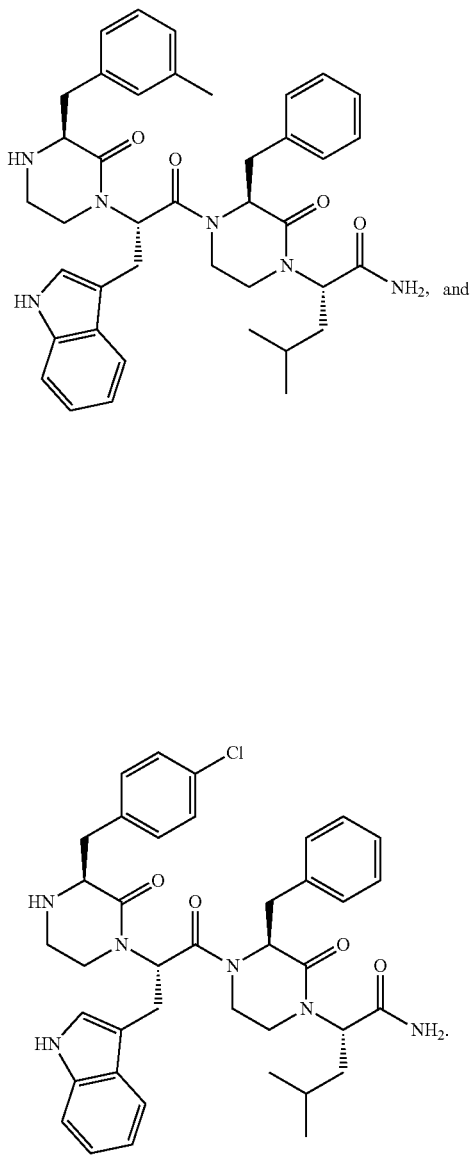
10. The oligooxopiperazine according to claim 9, wherein the oligooxopiperazine is selected from the group consisting of Oligooxopiperazine 15, Oligooxopiperazine 17, and Oligooxopiperazine 18.
* * * * *

UNITED STATES PATENT AND TRADEMARK OFFICE
CERTIFICATE OF CORRECTION

PATENT NO. : 11,180,481 B2  Page 1 of 2
APPLICATION NO. : 15/304490
DATED : November 23, 2021
INVENTOR(S) : Paramjit Arora et al.

It is certified that error appears in the above-identified patent and that said Letters Patent is hereby corrected as shown below:

In the Claims

At Claim 1, Column 48, Line 10-23, delete

" 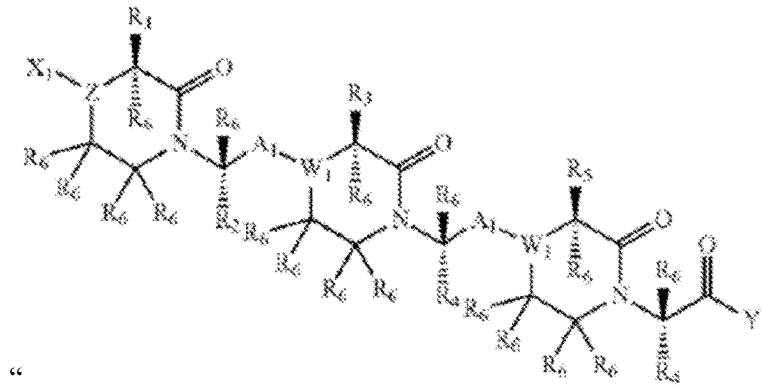 " and insert

-- 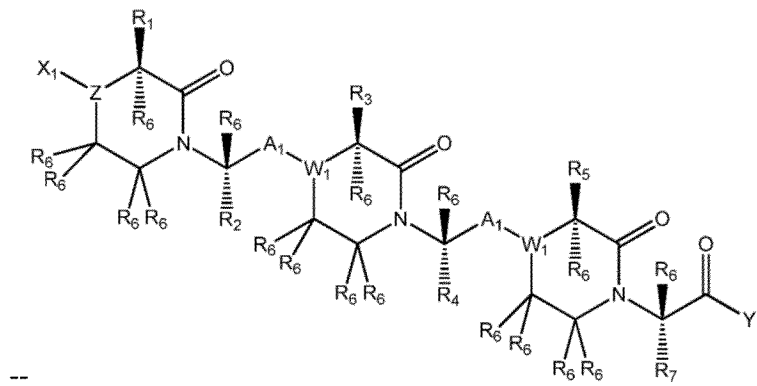 -- in its place.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,180,481 B2

At Claim 9, Column 53, Line 36-53, delete " 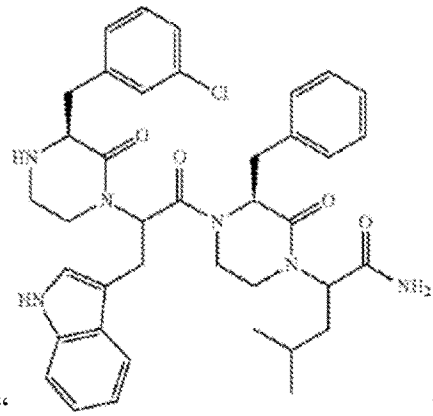 " and insert

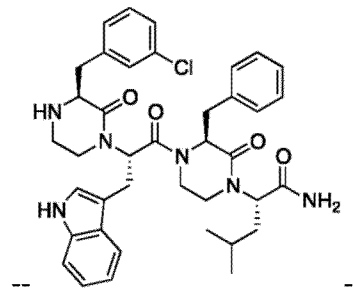 -- in its place.